US012766195B2

(12) United States Patent
Fox et al.

(10) Patent No.: US 12,766,195 B2
(45) Date of Patent: *Oct. 20, 2026

(54) # METHODS FOR TREATMENT USING ANTI-α4β7 ANTIBODY

(71) Applicant: Takeda Pharmaceutical Company Limited, Osaka (JP)

(72) Inventors: Irving H. Fox, Wellesley, MA (US); Catherine Scholz, Woburn, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/922,371

(22) Filed: Oct. 21, 2024

(65) Prior Publication Data

US 2025/0041424 A1 Feb. 6, 2025

Related U.S. Application Data

(63) Continuation of application No. 18/778,906, filed on Jul. 19, 2024, which is a continuation of application No. 16/743,813, filed on Jan. 15, 2020, now Pat. No. 12,053,526, which is a continuation of application No. 15/678,744, filed on Aug. 16, 2017, now abandoned, which is a continuation of application No. 14/114,832, filed as application No. PCT/US2012/036072 on May 2, 2012, now Pat. No. 9,764,033.

(60) Provisional application No. 61/585,859, filed on Jan. 12, 2012, provisional application No. 61/550,545, filed on Oct. 24, 2011, provisional application No. 61/481,533, filed on May 2, 2011.

(51) Int. Cl.

| | |
|---|---|
| ***A61K 39/00*** | (2006.01) |
| ***A61K 9/00*** | (2006.01) |
| ***A61K 9/19*** | (2006.01) |
| ***A61K 39/395*** | (2006.01) |
| ***A61K 47/18*** | (2017.01) |
| ***A61K 47/26*** | (2006.01) |
| ***C07K 16/28*** | (2006.01) |

(52) U.S. Cl.

CPC ............ *A61K 47/26* (2013.01); *A61K 9/0019* (2013.01); *A61K 9/19* (2013.01); *A61K 39/39591* (2013.01); *A61K 47/183* (2013.01); *C07K 16/2839* (2013.01); *A61K 2039/505* (2013.01); *A61K 2039/54* (2013.01); *A61K 2039/545* (2013.01); *C07K 2317/14* (2013.01); *C07K 2317/24* (2013.01); *C07K 2317/565* (2013.01); *C07K 2317/92* (2013.01); *C07K 2317/94* (2013.01)

(58) Field of Classification Search

None

See application file for complete search history.

(56) References Cited

U.S. PATENT DOCUMENTS

| | | | |
|---|---|---|---|
| 4,699,880 | A | 10/1987 | Goldstein |
| 4,816,397 | A | 3/1989 | Boss et al. |
| 4,816,567 | A | 3/1989 | Cabilly et al. |
| 5,223,392 | A | 6/1993 | Cohen |
| 5,225,538 | A | 7/1993 | Capon et al. |
| 5,225,539 | A | 7/1993 | Winter |
| 5,258,498 | A | 11/1993 | Huston et al. |
| 5,403,919 | A | 4/1995 | Butcher |
| 5,428,130 | A | 6/1995 | Capon et al. |
| 5,530,101 | A | 6/1996 | Queen et al. |
| 5,538,724 | A | 7/1996 | Butcher et al. |
| 5,558,864 | A | 9/1996 | Bendig et al. |
| 5,565,335 | A | 10/1996 | Capon et al. |
| 5,585,089 | A | 12/1996 | Queen et al. |
| 5,594,120 | A | 1/1997 | Brenner et al. |
| 5,599,676 | A | 2/1997 | Vonderheide et al. |
| 5,610,281 | A | 3/1997 | Brenner et al. |
| 5,624,321 | A | 4/1997 | Snyder |
| 5,624,821 | A | 4/1997 | Winter et al. |
| 5,648,260 | A | 7/1997 | Winter et al. |
| 5,665,595 | A | 9/1997 | Petell et al. |
| 5,688,916 | A | 11/1997 | Reid et al. |
| 5,693,761 | A | 12/1997 | Queen et al. |
| 5,693,762 | A | 12/1997 | Queen et al. |
| 5,714,147 | A | 2/1998 | Capon et al. |

(Continued)

FOREIGN PATENT DOCUMENTS

| | | | |
|---|---|---|---|
| EP | 0239400 | A2 | 9/1987 |
| EP | 0303463 | A2 | 2/1989 |
| GB | 2209757 | A | 5/1989 |
| JP | 06303990 | A | 11/1994 |
| WO | WO-1986001533 | A1 | 3/1986 |
| WO | WO-1988007089 | A1 | 9/1988 |
| WO | WO-1989007142 | A1 | 8/1989 |
| WO | WO-1990007321 | A2 | 7/1990 |
| WO | WO-1990007861 | A1 | 7/1990 |
| WO | WO-1991003252 | A1 | 3/1991 |
| WO | WO-1991009967 | A1 | 7/1991 |
| WO | WO-1992011018 | A1 | 7/1992 |

(Continued)

OTHER PUBLICATIONS

"Purified Rat Anti-Mouse MAdCAM-1" Technical Data Sheet (BD Pharmingen).

(Continued)

*Primary Examiner* — Maher M Haddad

(74) *Attorney, Agent, or Firm* — Womble Bond Dickinson (US) LLP

(57) ABSTRACT

Antibody formulations are described comprising a mixture of a non-reducing sugar, an anti-α4β7 antibody and at least one amino acid. The disclosed formulations have improved stability, reduced aggregate formation, and may retard degradation of the anti-α4β7 antibody therein or exhibit any combinations thereof. The present invention further provides a safe dosing regimen of these antibody formulations that is easy to follow, and which results in a therapeutically effective amount of the anti-α4β7 antibody in vivo.

30 Claims, 10 Drawing Sheets

Specification includes a Sequence Listing.

(56) References Cited

U.S. PATENT DOCUMENTS

| | | | | |
|---|---|---|---|---|
| 5,730,978 | A | 3/1998 | Wayner | |
| 5,821,337 | A | 10/1998 | Carter et al. | |
| 5,834,021 | A | 11/1998 | Speirs | |
| 5,840,299 | A | 11/1998 | Bendig et al. | |
| 5,859,205 | A | 1/1999 | Adair et al. | |
| 5,871,734 | A | 2/1999 | Lobb et al. | |
| 5,888,507 | A | 3/1999 | Burkly | |
| 5,932,214 | A | 8/1999 | Lobb et al. | |
| 6,015,662 | A | 1/2000 | Hackett, Jr. et al. | |
| 6,551,593 | B1 | 4/2003 | Ringler et al. | |
| 9,663,579 | B2 | 5/2017 | Fox et al. | |
| 9,764,033 | B2 | 9/2017 | Diluzio et al. | |
| 10,004,808 | B2 | 6/2018 | Fox et al. | |
| 10,143,752 | B2 | 12/2018 | Fox et al. | |
| 10,918,716 | B2 | 2/2021 | Lissoos et al. | |
| 11,596,688 | B2 | 3/2023 | Rosario et al. | |
| 11,884,731 | B2 * | 1/2024 | Lasch | A61P 37/00 |
| 12,053,526 | B2 | 8/2024 | Scholz et al. | |
| 12,053,744 | B2 | 8/2024 | Anquetil | |
| 12,171,832 | B2 | 12/2024 | Fox et al. | |
| 2002/0147314 | A1 | 10/2002 | Briskin et al. | |
| 2002/0172679 | A1 | 11/2002 | Ringler et al. | |
| 2004/0009169 | A1 | 1/2004 | Taylor et al. | |
| 2004/0023373 | A1 | 2/2004 | Briskin | |
| 2005/0095238 | A1 | 5/2005 | Brettman et al. | |
| 2005/0260193 | A1 | 11/2005 | Lieberburg | |
| 2007/0122404 | A1 | 5/2007 | O'Keefe | |
| 2012/0282249 | A1 | 11/2012 | Fox et al. | |
| 2014/0377251 | A1 | 12/2014 | Diluzio et al. | |
| 2018/0207279 | A1 | 7/2018 | Fox et al. | |
| 2018/0289811 | A1 | 10/2018 | Fox et al. | |
| 2019/0076532 | A1 | 3/2019 | Diluzio et al. | |
| 2019/0231878 | A1 | 8/2019 | Brown et al. | |
| 2020/0206353 | A1 | 7/2020 | Fox et al. | |
| 2021/0052733 | A1 | 2/2021 | Diluzio et al. | |
| 2021/0340261 | A1 | 11/2021 | Diluzio et al. | |
| 2022/0370617 | A1 | 11/2022 | Diluzio et al. | |
| 2025/0000981 | A1 | 1/2025 | Diluzio et al. | |

FOREIGN PATENT DOCUMENTS

| | | | |
|---|---|---|---|
| WO | WO-1993002191 | A1 | 2/1993 |
| WO | WO-1993015764 | A1 | 8/1993 |
| WO | WO-1993023526 | A1 | 11/1993 |
| WO | WO-1994012214 | A1 | 6/1994 |
| WO | WO-1994013312 | A1 | 6/1994 |
| WO | WO-1994016094 | A2 | 7/1994 |
| WO | WO-1994017828 | A2 | 8/1994 |
| WO | WO-1994029351 | A2 | 12/1994 |
| WO | WO-1995019790 | A1 | 7/1995 |
| WO | WO-1997018838 | A1 | 5/1997 |
| WO | WO-1997025351 | A2 | 7/1997 |
| WO | WO-1998006248 | A2 | 2/1998 |
| WO | WO-2001078779 | A2 | 10/2001 |
| WO | WO-03/009817 | A2 | 2/2003 |
| WO | WO-2006026759 | A2 | 3/2006 |
| WO | WO-2008071394 | A1 | 6/2008 |
| WO | WO-2009009407 | A1 | 1/2009 |
| WO | WO-2011/017070 | A1 | 2/2011 |
| WO | WO-2012135589 | A1 | 10/2012 |

OTHER PUBLICATIONS

555945, BD Biosciences Pharmingen Integrin b7 BD Biosciences Online Catalog [online], 2005 [retrieved on Apr. 4, 2005]. Retrieved from the Internet: <URL: http://www.bdbiosciences.com/ptProduct.jsp?backLink=ptProductList.jsp&bac-kName=Product%20List&Prold=15874>.

Adams et al., "Aberrant Homing of Mucosal T Cells and Extra-Intestinal Manifestations of Inflammatory Bowel Disease," Nature, 6:244-251 (2006).

Adams et al., "Complementary DNA Sequencing: Expressed Sequence Tags and Human Genome Project," Science, 252:1651-1656 (1991).

Adams et al., "Initial Assessment of Human Gene Diversity and Expression Patterns Based Upon 83 Million Nucleotides of cDNA Sequence," Nature (Supp), 377:3-174 (1995).

Adams et al., "Sequence Identification of 2,375 Human Brain Genes," Nature, 355:632-633 (1992).

Andrew et al., "Distinct but Overlapping Epitopes are Involved in .alpha.4.beta.7-Mediated Adhesion to Vascular Cell Adhesion Molecule-1, Mucosal Addressin-1, Fibronectin, and Lymphocyte Aggregation," J. of Immunology, 153:3847-3861 (1994).

Andrew et al., "TABS, A T Cell Activation Antigen that Induces LFA-1-Dependent Aggregation," The Journal of Immunology, 155:1671-1684 (1995).

Aruffo et al., "Molecular Cloning of a CD28 cDNA by a High-Efficiency COS Cell Expression System," Proc. Natl. Acad. Sci. USA, 84:8573-8577 (1987).

ATCC No. HB-293, FIB504.64, ATCC Cell Biology Catalog [online], 2005 [retrieved on May 27, 2005]. Retrieved from Internet: <URL: http://www.atcc.org/common/catalog/numSearch/numResults.cfm?atccNum=HB-29- 3>.

Bednarczyk et al., "Identification of a Combinatorial Epitope Expressed by the Integrin α4β7 Heterodimer Involved in the Regulation of Cell Adhesion," J. Biol. Chem., 289(11):8348-8354 (1994).

Bendig, "Humanization of Rodent Monoclonal Antibodies by CDR Grafting," Methods: A Companion to Methods in Enzymology, 8:83-93 (1995).

Berg et al., "L-Selectin-Mediated Lymphocyte Rolling on MAdCAM-1," Nature, 366:695-698 (1993).

Berlin et al. "α4β7 Integrin Mediates Lymphocyte Binding to the Muscosal Vascular Addressin MAdCAM-1," Cell, 74:185-195 (1993).

Berlin et al., "α4 Integrins Mediate Lymphocyte Attachment and Rolling under Physiological Flow," Cell, 80:413-422 (1995).

Bloom, et al., "Adhesion Molecule Expression in Primary Sclerosing Cholangitis and Primary Biliary Cirrhosis," Gut, 36:604-609 (1995).

Bozic C.R., et al., "The Murine Interleukin 8 Type B Receptor Homologue and Its Ligands," J. Biol. Chem., 269:29355-29358 (1994).

Briskin et al., "Structural Requirements for Mucosal Vascular Addressin Binding to its Lymphocyte Receptor .alpha.4.beta.7," J. Immunol., 156:719-726 (1996).

Briskin, M.J., et al., "MAdCAM-1 Has Homology to Immunoglobulin and Mucin-Like Adhesion Receptors and to IgA1." Nature. 363:451-453 (1993).

Brossay et al., "Mimicry of a Neutralizing Epitope of the Major Outer Membrane Protein of Chlamydia Trachomatis by Anti-Idiotypic Antibodies," Infection and Immunity, 62:341-347 (1994).

Brown, J., et al., "Critical Evaluation of ECV304 as a Human Endothelial Cell Model Defined by Genetic Analysis and Functional Responses: A Comparison with the Human Bladder Cancer Derived Epithelial Cell Line T24/83," Laboratory Investigation, 80:37-45 (2000).

Calvete et al., "Further Studies on the Topography of Human Platelet Glycoprotein IIb," Biochem, 273:767-775 (1991).

Carr et al., "Monocyte Chemoattractant Protein 1 Acts as a T-lymphocyte Chemoattractant," Proc. Natl. Acad. Sci. USA, 91:3652-3656 (1994).

Chenna et al., "Multiple Sequence Alignment with the Clustal Series of Programs," Nucleic Acids Research, 31:3497-3500 (2003).

Chensue et al., "Monocyte Chemotactic Protein Expression During Schistosome Egg Granuloma Formation," Am. J. of Pathology, 146(1):130-138 (1995).

Cleland et al., "A Specific Molar Ratio of Stabilizer to Protein is Required for Storage Stability of a Lyophilized Monoclonal Antibody," Journal of Pharmaceutical Sciences, 90:310-321 (2001).

Cooper et al., "Clinicopathologic Study of Dextran Sulfate Sodium Experimental Murine Colitis," Laboratory Investigations, 69(2):238-249 (1993).

Creyghton, W.M., et al., "Cytokine-Mediated Modulation of Integrin, ICAM-1 and CD44 Expression on Human Uveal Melanoma Cells in Vitro," Melanoma Research, 5:235-242 (1995).

Cunliffe et al., "Review Article: Monitoring for Drug Side-Effects in Inflammatory Bowel Disease," Aliment Pharmacol Ther., 16:647-662 (2002).

(56) References Cited

OTHER PUBLICATIONS

De Fougerolles et al. , "Intercellular Adhesion Molecule 3, a Third Adhesion Counter-Receptor for Lymphocyte Function-associated Molecule 1 on Resting Lymphocytes," J. Exp. Med., 175:185-190 (1992).
Declaration from Erik Fedyk.
Declaration from Michael Briskin.
Declaration from Vilmos Csizmedia.
Dirks, W.G., et al., Letter to the Editor, "ECV304 (Endothelial) Is Really T24 (Bladder Carcinoma): Cell Line Cross-Contamination at Source," In Vitro Cell Dev. Biol. Animal, 35:558-559 (1999).
Dowbenko, D., et al., "Cloning of a Rat Homologue of Mouse GlyCAM 1 Reveals Conservation of Structural Domains," J. Biol. Chem., 268: 14399-14403 (1993).
Dignass, A.U., "New Devlopments in the Management of Steroid-refractory Inflammatory Bowel Disease," Business Briefing: European Gastroenterology Review, 2005, pp. 1-5.
Duenas et al., "Clonal Selection and Amplification of Phage Displayed Antibodies by Linking Antigen Recognition and Phage Replication," Bio/Technology, 12:999-1002 (1994).
Erle et al., Expression and Function of the MAdCAM-1 Receptor, Integrin .alpha.4.beta.7, on Human Leukocytes,: J. of Immunology. 153:517-528 (1994).
Feagan BG, Leach T, Milch C, Parikh A, Fox IH, Emerging safety profile of vedolizumab: a novel, selective integrin inhibitor for the treatment of IBD. P-0025 poster (2009).
Feagan et al, "A randomized Controlled Trial of a Humanized .alpha.4.beta.7 Antibody in Ulcerative Colitis (UC)," Am J Gastroenterol, 98(9s):S248-S249. Abstract 749 (2003).
Feagan et al, "Efficacy and Safety of a Humanized .alpha.4.beta.7 Antibody in Active Crohn's Disease (CD). Gastroenterology," 124(4)(suppl 1):A25-A26. Abstract 178 (2003).
Feagan et al., "An Ascending Dose Trial of a Humanized A. sub 4B.sub.7 Antibody in Ulcerative Colitis(UC)," Gastroenterol. ,118(4):A874, (Abstract No. 4851), (2000).
Feagan et al., "Emerging Safety Profile of Vedolizumab: A Novel, Selective Integrin Inhibitor for Treatment of IBD," J Crohn's Colitis, 4(suppl 1) Abstract p.149 (2010).
Feagan et al., "Emerging Safety Profile of Vedolizumab: A Novel, Selective Integrin Inhibitor for Treatment of Ibd," p. 149 poster (2010).
Feagan et al., "Treatment of Active Crohn's Disease with MLN0002, a Humanized Antibody to the alpha4beta7 Integrin", Clin Gastroenterol Hepatol., Dec. 2008;6(12):1370-7 (Abstract only).
Feagan et al., "Treatment of Ulcerative Colitis with a Humanized Antibody to the .alpha.4.beta.7 Integrin," the New England Journal of Medicine, 352:2499:2507 (2005).
Feagan et al., "Vedolizumab as Induction and Maintenance Therapy for Ulcerative Colitis," The New England Journal of Medicine, 369(8):699-710 (2013).
Feagan, et al., "Emerging Safety Profile of Vedolizumab: A Novel, Selective Integrin Inhibitor for the Treatment of IBD," 15(S2): S12, Abstract p. 0025, 2009 IBD Abstracts (2009).
Federlin, "Immunological aspects of inflammatory bowel diseases," Immun. Infekt., 6:15-27 (1978) (abstract only).
Fedyk ER, Yang L, Csizmadia V, Yang H, Wyant T, Kadambi VJ, et al, Regional immunomodulation of the gastrointestinal tract without systemic immunosuppression in Cynomolgus macaques by vedolizumab. p. 0144 poster (2009).
Fedyk et al, "The Pharmacologic and Toxicologic Profile of the Gastrointestinal-Selective, Anti-Inflammatory Drug Vedolizumab in Cynomolgus Macaques," J Crohn's Colitis, 4(suppl 1) Abstract Oral 9 (2010).
Fedyk et al, "The Pharmacologic and Toxicologic Profile of the Gastrointestinal-Selective, Anti-Inflammatory Drug Vedolizumab in Cynomolgus Macaques," presentation (2010).
Fedyk et al., "Pharmacologic Profile of the Gasteointestinal-Selective Anti-Inflammatory Drug Vedolizumab in Cynomolgus Macaques," Gut, 59(suppl III):A74. Abstract OP339 (2010).
Fedyk et al., "Pharmacologic Profile of the Gastrointestinal-Selective Anti-Inflammatory Drug Vedolizumab in Cynomolgus Macaques," (2010) presentation.
Fedyk et al., "The Gastrointestinal-Selective Biologic Vedolizumab Does Not Impair Immune Surveillance of the Central Nervous System in Non-Human Primates," Inflamm Bowel Disease, 17(suppl S1):S4-S5. Abstract O-015 (2011).
Fedyk et al., "The Gastrointestinal-Selective Biologic Vedolizumab Does Not Impair Immune Surveillance of the Central Nervous System in Non-Human Primates," J Crohn's Colitis, 5(1):S13-S14. Abstract P002 (2011).
Fedyk et al., "The Gastrointestinal-Selective Biologic Vedolizumab Does Not Impair Immune Surveillance of the Central Nervous System in Non-Human Primates," P002 poster (2011).
Fedyk et al., "The Gastrointestinal-Selective Biologic Vedolizumab Does Not Impair Immune Surveillance of the Central Nervous System in Non-Human Primates," Presentation (2011).
Fedyk, et al., "Regional Immunomodulation of the Gastrointestinal Tract Without Systemic Immunosuppression in Cynomolgus Macaques by Vedolizumab," 15(S2): S50, Abstract P-0144, 2009 IBD Abstracts (2009).
Focosi, "Concerns on Unpredictable Pharmacokinetics and Pharmacodynamics of Natalizumab," American Neurological Association, p. 270 (2010).
Forrester, J.V., and Lackie, J.M., "Adhesion of Neutrophil Leucocytes Under Conditions of Flow," J. Cell Sci., 70:93-110 (1984).
Goldenberg, D.M., "New Developments in Monoclonal Antibodies for Cancer Detection and Therapy," CA Cancer J. Clin., 44:43-64 (1994).
Gordon et al., "Randomised Double-Blind Placebo-Controlled Trial of Recombinant Humanised Antibody to .alpha.4 Integrin (Antegren. TM.) in Active Crohn's Disease," Gastroenterology, 116(4) Part 2:A726 (1999).
Gordon, "Treatment of Active Ulcerative Colitis with a Recombinant Humanised Antibody to alpha.4 integrin (AntegrenTM.)," Gastroenterology, 116(4) Part 2:A726 (1999).
Gorman et al., "Humanisation of Monoclonal Antibodies for Therapy," Sem. Immunol., 2(6):457-466 (1990).
Grant et al., "MAdCAM-1 Expressed in Chronic Inflammatory Liver Disease Supports Mucosal Lymphocyte Adhesion to Hepatic Endothelium (MAdCAM-1 in Chronic Inflammatory Liver Disease)," Hepatology, 33:1065-1072 (2001).
Hall, D.E., et al., "The .alpha.1/.beta.1 and .alpha.6/.beta. 1 Integrin Heterodimers Mediate Cell Attachment to Distinct Sites on Laminin," J. Cell Biol., 110:2175-2184 (1990).
Hamann et al., "Role of a4-Integrins in Lymphocyte Homing to Mucosal Tissues in Vivo," Journal of Immunology, 152:3282-3293 (1994).
Hanninen A., et al., "Vascular Addressins Are Induced on Islet Vessels during Insulitis in Nonobese Diabetic Mice and Are Involved in Lymphoid Cell Binding to Islet Endothelium" J. Clin Invest., 92(5):2509-2515 (1993).
Harris et al., "Therapeutic Antibodies—The Coming of Age," Tibtech 11:42-44 (1993).
Herlyn et al., "Anti-Idiotypic Antibodies Bear the Internal Image of a Human Tumor Antigen," Science 232:100-102 (1986).
Hession et al., "Endothelial Leukocyte Adhesion Molecule 1: Direct Expression Cloning and Functional Interactions," Proc. Natl. Acad. Sci. USA, 87:1673-1677 (1990).
Hesterberg et al., "Rapid Resolution of Chronic Colitis in the Cotton-Top Tamarin with an Antibody to a Gut-Homing Intergrin .alpha.4.beta.7," Gastroenterology, 111:1373-1380 (1996).
Higgins, D.G., et al., "Using Clustal for Multiple Sequence Alignments," Methods in Enzymology, 266:383-402 (1996).
Higgins, D.H., Sharp, P.M., "Clustal; A Package for Performing Multiple Sequence Alignment on a Microcomputer," Gene, 73:237-244 (1988).
Hoentjen et al., "Safety of Anti-Tumor Necrosis Factor Therapy in Inflammatory Bowel Disease," World Journal of Gastroenterology, 15(17):2067-2073 (2009).

(56) References Cited

OTHER PUBLICATIONS

Holzmann, B., et al., "Identification of a Murine Peyer's Patch-Specific Lymphocyte Homing Receptor as an Integrin Molecule with an .alpha Chain Homologous to Human VLA-4.alpha.," Cell, 56:37-46 (1989).
Hu, M. C-T et al., "Cloning and Expression of Mouse Integrin .beta..rho.(.beta.7): A functional Role in Path-Specific Lymphocyte Homing," Proc. Natl. Acad. Sci., 89:8254-8258 (1992).
Huffnagle et al., "The Role of Monocyte Chemotactic Protein-1 (MCP-1) in the Recruitment of Monocytes and CD4 +T Cells During a Pulmonary Cryptococcus Neoformans Infection," J. of Immunology, 155:4790-4797 (1995).
Hutchinson, M., "Natalizumab: A New Treatment for Relapsing Remitting Multiple Sclerosis," Ther Clin Risk Manag. 3(2): 259-268 (2007).
Hynes, "Integrins: Versatility, Modulation, and Signaling in Cell Adhesion," Cell, 69:11-25 (1992).
Katz, "Medical and Surgical Management of Severe Colitis," Seminars in Gastrointestinal Disease, 11(1):18-32 (2000).
Katz, "Update in Medical Therapy in Inflammatory Bowel Disease: A Clinician's View," Digestive Diseases, 17:163-171 (1999).
Keeley et al., "Natalizumab for the Treatment of Multiple Sclerosis and Crohn's Disease," 39:1833-1843 (2005).
Kettleborough et al., "Humanization of a Mouse Monoclonal Antibody by CDR-Grafting: The Importance of Framework Residues on Loop Conformation," Protein Engng., 4(7):773-783 (1991).
Kola, et al., "Can the Pharmaceutical Industry Reduce Attrition Rates?", Nature Reviews, Drug Discovery, (2004), pp. 711-715, vol. 3.
International Search Report and the Written Opinion from Corresponding PCT/US2012/036072 dated Oct. 29, 2012.
Labrijin et al., "Therapeutic IgG4 Antibodies Engage in Fab-Arm Exchange with Endogenous Human IgG4 in Vivo," Nature Biotechnology, 27(8):767-772 (2009).
Lang, "Promising New Agents for the Treatment of Inflammatory Bowel Disorders," Drugs R&D, 1(3): 237-244 (1999).
Lazarovits et al., ".alpha.4.beta.7 Integrin in Rheumatoid Arthritis," in Leukocyte Typing V-White Cell Differentiation Antigens, S.F. Schlossman et al., eds., (Oxford: Oxford University Press), pp. 1686-1687 (1995).
Lazarovits et al., "Differential Expression in Rheumatoid Synovium and Synovial Fluid of .alpha.4.beta.7 Integrin—A Novel Receptor for Fibronectin and Vascular Cell Adhesion Molecule-1," J. Immunol., 151(11):6482-6489 (1993).
Lazarovits et al., "Lymphocyte Activation Antigens-I. A Monoclonal Antibody, Anti Act 1, Defines a New Late Lymphocyte Activation Antigen," J. Immunol., 133:1857-1862 (1984).
Lederman et al., "A Single Amino Acid Substitution in a Common African Allele of the CD4 Molecule Ablates Binding of the Monoclonal Antibody, OKT4," Molec. Immunol., 28:1171-1181 (1991).
Leung et al., "Cloning of the Mucosal Addressin MAdCAM-1 from Human Brain: Identification of Novel Alternatively Spliced Transcripts," Immunology and Cell Biology, 74:490-496 (1996).
Lin Ko-Chung et al., "Very Late Antigen 4 (VLA4) Antagonists as Anti-Inflammatory Agents," Current Opinion in Chemical Biology, 2(4):453-457 (1998).
Lobb et al., The Role of .alpha.4.beta.7 Integrins in Lung Pathophysiology, Eur. Respir. J., 9 (Supp 22):104s-108s (1996).
Loetscher et al., "Monocyte Chemotactic Proteins MCP-1, MCP-2, and MCP-3 are Major Attractants for Human CD4 + and CD8+a T Lymphocytes," Faseb J., 8:1055-1060 (1994).
Ma, Philip, et al., "Value of Novelty?", Nature Reviews, Drug Discovery, Aug. 2002, pp. 571-572, vol. 1.
McDonald, et al., "Selective Biopsy of Human Peyer's Patches During Ileal Endoscopy," Gastroenterology, 93:1356-1362 (1987) (abstract only).
Marehbian et al., Adverse Events Associated with Common Therapy Regimens for Moderate-to-Severe Crohn's Disease, The American Journal of Gastroenterology, 104:2524-2533 (2009).
Marlin et al., "Purified Intercellular Adhesion Molecule-1 (ICAM-1) is a Ligand for Lymphocyte Function-Associated Antigen 1 (LFA-1)," Cell, 51:813-819 (1987).
Mawhorter et al., "Identification of Surface Molecules Associated with Physiologic Activation of Eosinophils. Application of Whole-Blood Flow Cytometry to Eosinophils," J. Immunol., 156:4851-4858 (1996).
Mayo Clinic Staff, Inflammatory Bowel Disease (IBD) Treatments and Drugs—Mayo Clinic. http://www.mayoclinic.org/diseases/conditions/inflammatory-bowel-disease/basics/treatment/con-20034908, pp. 1-8, May 26, 2015.
McLure, M.A., et al., "Comparative Analysis of Multiple Protein-Sequence Alignment Methods," Mol. Biol. Evol. 11(4):571-592 (1994).
Michie et al., "The Human Peripheral Lymph Node Vascular Addressin, an Inducible Endothelial Antigen Involved in Lymphocyte Homing," American Journal of Pathology, 143(6):1688-1698 (1993).
Mountain, A. and Adair, J.R., "Engineering Antibodies for Therapy," Biotechnol. Genet. Eng. Rev., 10:1-1412 (1992).
Nakache et al., "The Mucosal Vascular Addressin is a Tissue-Specific Endothelial Cell Adhesion Molecule for Ciculating Lymphocytes." Nature, 337:179-181 (1989).
Natalizumab, http://en.wikipedia.org/wiki/Natalizumab, May 26, 2015, pp. 1-4.
Ngo et al., "Chapter 14," in the Protein Folding Problem and Tertiary Structure Predication, Merz et al., eds. (Boston: Birkhauser), pp. 491-495 (1994).
Nieto et al., "Expression of Functionally Active .alpha.4.beta. 1 Integrin by Thymic Epithelial Cells," Clin. Exp. Immunol. 106:170-178 (1996).
O'Kennedy et al., "Antibody Engineering: An Overview," Essays Biochem., 26:59-75 (1991).
Okayasu et al., "A Novel Method in the Induction of Reliable Experimental Acute and Chronic Ulcerative Colitis in Mice," Gastroenterology, 98:694-702 (1990).
Olson, T.S., and Ley, K., "Chemokines and Chemokine Receptors in Leukocyte Trafficking," Am. J. Physiol. Regulatory Integrative Comp Physiol., 283:R7-R28 (2002).
Osband et al., "Problems in the Investigational Study and Clinical use of Cancer Immunotherapy," Immunol. Today, 11(6):193-195 (1990).
Osband et al., "Problems in the Investigational Study and Clinical use of Cancer Immunotherapy," Immunol. Today, 11:103-105 (1990).
Osborn et al., "Direct Expression Cloning of Vascular Cell Adhesion Molecule 1, A Cytokine-Induced Endothelial Protein that Binds to Lymphocytes," Cell, 59:1203-1211 (1989).
Osborn, L., et al., "Arrangement of Domains, and Amino Acid Residues Required for Binding of Vascular Cell Ashesion Molecule-1 to Its Counter-Receptor VLA-4 (.alpha.4.beta. 1)," J. Cell Biol., 124:601-608 (1994).
Owens et al., "The Genetic Engineering of Monoclonal Antibodies," J. Immunol. Methods, 168(2):149-165 (1994).
Page et al., "High Level Expression of the Humanized Monoclonal Antibody Campth-1 H in Chinese Hamster Ovary Cells," Bio/Technology, 9:64-68 (1991).
Pals et al., "Expression of the Mucosal Homing Receptor .alpha.4.beta.7 in Malignant Lymphomatous Polyposis of the Intestine," Gastroenterology, 107:1519-1523 (1994).
Pan, J., et al., "Comparison of Promoters for the Murine and Human P-Selectin Genes Suggests Species-Specific and Conserved Mechanisms for Transcriptional Regulation in Endothelial Cells," J. Biol. Chem., 273:10058-10067 (1998).
Panitch, H.S., et al., "Exacerbations of Multiple Sclerosis in Patients Treated with Gamma Interferon," The Lancet 1(8538):893-895 (1987).
Parikh et al, "Gastrointestinal Selectivity of Vedolizumab (MLN0002), a Humanized Monoclonal Antibody to the .alpha.4.beta.7 Integrin," J Crohn's Colitis, 3(1):562. Abstract P130 (2009).
Parikh et al, "Gastrointestinal Selectivity of Vedolizumab (MLN0002), a Humanized Monoclonal Antibody to the .alpha.4.beta.7 Integrin. Inflamm Bowel Disease," P-0025 poster (2008).

(56) References Cited

OTHER PUBLICATIONS

Parikh et al., "Long-Term Clinical Experience with Vedolizumab for the Treatment of Inflammatory Bowel Disease: a Phase 2 Open-Label Safety Extension Study," J Crohn's Colitis, 5(1):S123. Abstract P263 (2011).
Parikh et al., "Long-Term Clinical Experience with Vedolizumab for the Treatment of Inflammatory Bowel Disease: A Phase 2 Open-Label Safety Extension Study," P263 poster (2011).
Parikh et al., "Long-Term Clinical Experience with Vedolizumab for the Treatment of Inflammatory Bowel Disease: Results of a Phase 2 Open-Label Safety Extension Study," Inflamm Bowel Disease, 17(suppl S1):S56. Abstract P-146 (2011).
Parikh et al., "Long-Term Clinical Experience with Vedolizumab for the Treatment of Inflammatory Bowel Disease: Results of a Phase 2 Open-Label Safety Extension Study," P-146 poster (2011).
Parikh et al., "No Association Between Vedolizumab Exposure and Serum JC Virus Levels," J Crohn's Colitis, 5(1):S109-S110. Abstract P231 (2011).
Parikh et al., "No Association Between Vedolizumab Exposure and Serum JC Virus Levels," P-147 poster (2011).
Parikh et al., "No Association Between Vedolizumab Exposure and Serum JC Virus Levels," P231 poster (2011).
Parikh et al., "No Increase in JC Viremia, Lymphocyte Count, or Circulating CD34+ Hematopoietic progenitor Cells After Treatment with Vedolizumab, a Humanized Monoclonal Antibody to .alpha. 4.beta.7 Integrin," Gastroenterolgy, vol. 138, No. 5, Supp.Supp. 1, pp. S145-S146. Abstract No. 1008 (2010).
Parikh et al., "No Increase in JC Viremia, Lymphocyte Count, or Circulating CD34+ Hematopoietic Progenitor Cells After Treatment with Vedolizumab," (2010) presentation.
Parikh et al., "No Increase in JC Viremia, Lymphocyte Count, or Circulating CD34+ Hematopoietic Progenitor Cells After Treatment with Vedolizumab," Gut, 59(suppl III):A73. Abstract OP338 (2010).
Parikh et al., "Vedolizumab for the Treatment of Active Ulcerative Colitis: A Randomized Controlled Phase 2 Dose-ranging Study," Inflamm. Bowel Dis., 18(8):1470-1479 (2012).
Patient Information on Corticosteroids, Australian Rheumatology Association, pp. 1-4, May 2009.
Pennica et al., "Expression Cloning of Cardiotrophin 1, A Cytokine that Induces Cardiac Myocyte Hypertrophy," Proc. Natl. Acad. Sci., 92:1142-1146 (1995).
Petrovic et al., "LPAM (.alpha.4.beta.7 Integrin) is an Important Homing Integrin on Alloreactive T Cells in the Development of Intestinal Graft-Versus-Host Disease," Blood, 103:1542-1547 (2004).
Picker et al., "Physiological and Molecular Mechanisms of Lymphocyte Homing," Annu. Rev. Immunol., 10:561-591 (1992).
Podolsky, "Inflammatory Bowel Disease (First of Two Parts)," the New England Journal of Medicine, 325(13):928-937 (1991).
Podolsky, "Inflammatory Bowel Disease (Second of Two Parts)," the New England Journal of Medicine, 325(14):1008-1016 (1991).
Podolsky, "Inflammatory Bowel Disease," New England Journal of Medicine, 347(6):417-429 (2002).
Podolsky, D.K, et al., "Attenuation of Colitis in the Cotton-Top Tamarin by Anti-a.sub.4 integrin Monoclonal Antibody," J. Clin, Invest., 92:372-380 (1993).
Postigo et al., ".alpha.4.beta.7 Integrin Mediates B-Cell Binding to Fibronectin and Vascular Cell Adhesion Molecule-1," J. Immunol, 151(5):2471-2483 (1993).
Prakash et al., "Cloning and Analysis of Murine cDNA that Encodes a Fibrogenic Lymphokine, Fibrosin," Proc. Natl. Acad. Sci. USA, 92:2154-2158 (1995).
Prasad et al., "Evaluation of Mutagenesis for Epitope Mapping," the Journal of Biological Chemistry, 15:10705-10708 (1993).
Present, "How to do Without Steroids in Inflammatory Bowel Disease," Inflammatory Bowel Diseases, 6(1):48-57 (2000).
Pritsch et al., Can Immunoglobulin C.sub.H1 Constant Region Domain Modulate Antigen Binding Affinity of Antibodies? J. Clin. Invest., 98:2235-2243 (1996).
Pulido et al., "Functional Evidence for Three Distinct and Independently Inhibitable Adhesion Activities Mediated by the Human Integrin VLA-4," J. Biol. Chem. 266(16):10241-10245 (1991).
Reichert, Janice M., Antibodies to watch in 2011. mAbs 3(1), 76-99 (2011).
Reichmann et al., "Reshaping Human Antibodies for Therapy," Nature, 332:323-327 (1988).
Rice, G.E., et al., "Vascular and Nonvascular Expression of INCAM-110; A Target for Mononuclear Leukocyte Adhesion in Normal and Inflamed Human Tissues," Am. J. of Pathology, 138:385-393 (1991).
Rinaldi et al., "Severe Relapses after the First Infusion of Natalizumab in Active Relapsing-Remitting Multiple Sclerosis," Multiple Sclerosis, 15(11):1359-1362 (2009).
Ringler, et al., "Cellular Localization of Simian Immunodeficiency Virus in Lymphoid Tissues I. Immunohistochemistry and Electron Microscopy," American Journal of Pathology, 134(2):373-383 (1989).
Roberts et al., "The Mucosal T-Cell Integrin .alpha.M290.beta.7 Recognizes a Ligand on Mucosal Epithelial Cell Lines," Eur. J. Immunol., 23:1630-1635 (1993).
Rott et al., "Expression of Mucosal Homing Receptor .alpha.4. beta.7 by Circulating CD4+ Cells with Memory for Intestinal Rotavirus," J. Clin Invest., 100(5):1204-1208 (1997).
Rudikoff et al., "Single Amino Acid Substitution Altering Antigen-Binding Specificity," Proc. Natl. Acad. Sci. USA, 79:1979-1983 (1982).
Rudinger, "Characteristics of the Amino Acids as Components of a Peptide Hormone Sequence," in Peptide Hormones, Parsons, J.A. (Ed.), University Park Press, Baltimore, M.D., p. 1-7 (1976).
Rutgeerts, "Review Article: Efficacy of Infliximab in Crohn's Disease-Induction and Maintenance of Remission," Aliment Pharmacol. Ther., 13(Suppl. 4):9-15 (1999).
Rutgeerts, "Summary," Aliment Pharmacol. Ther., 13(Suppl. 4):38 (1999).
Sachar, "How to do Without Steroids in Inflammatory Bowel Disease," Inflammatory Bowel Diseases, 6(1):58 (2000).
Sadlack et al., "Ulcerative Colitis-Like Disease in Mice with a Disrupted Interleukin-2 Gene," Cell, 75:253-261 (1993).
Salmi et al., "Aberrant Binding of Lamina Propia Lymphocytes to Vascular Endothelium in Inflammatory Bowel Diseases," Gastroenterology, 106:596-605 (1994).
Salmi et al., "Dual Binding Capacity of Mucosal Immunoblasts to Mucosal and Synovial Endothelium in Humans: Dissection of Molecular Mechanisms," J. Exp. Med., 181:137-149 (1995).
Sanborn et al., "Vedolizumab as Induction and Maintenance Therapy for Crohn's Disease," The New England Journal of Medicine, 369(8):711-721 (Aug. 22, 2013).
Sanchez et al., "VLA-3: A Novel Polypeptide Associate Within the VLA Molecular Complex: Cell distribution and Biochemical Characterization," Eur. J. Immunol., 16:1343-1349 (1986).
Santa Cruz Biotechnology Inc., ECV304 Human Whole Cell Lysate (sc-2269) Technical Datasheet.
Santa Cruz Biotechnology Inc., MAdCAM-1 siRNA (h) Technical Datasheet.
Santa Cruz Biotechnology, Inc. MAdCam-1 (Meca-367): sc-19604, www.scbt.com, obtained Sep. 25, 2007.
Scholz C, Wyant T, Leach T, Sankoh S, Mould DR, Patella M, et al., Clinical pharmacology of vedolizumab (MLN0002) in patients with active ulcerative colitis. P164 poster (2009).
Scholz et al., "Clinical Pharmacology of Vedolizumab (MLN0002) in Patients with Active Ulcerative Colitis," ECCO Annual Meeting Hamburg, Germany Feb. 5, 2009.
Schulz et al., Proteolytic Cleavage of CD25, the .alpha. Subunit of the Human T Cell Interleukin 2 Receptor, by Der p. 1, a Major Mite Allergen with Cysteine Protease Activity, J. Exp. Med., 187:271-275 (1998).
Schweighoffer et al., "Selective Expression of Integrin .alpha.4. beta.7 on a Subset of Human CD4+ Memory T Cells with Hallmarks of Gut-Trophism," the Journal of Immunology, 151:717-729 (1993).
Sela, "Overview: Antigens," in Handbook of Exp. Immunol., Immunochemistry, Weir et al., ed. Balckwell Sci. Pub., p. 1.1-1.7 (1986).

(56) References Cited

OTHER PUBLICATIONS

Shaw et al., "Molecular Cloning of the Human Mucosal Lymphocyte Integrin .alpha.E Subunit," J. Biol. Chem. 269(5):6016-6025 (1994).
Shaw et al., "Mouse/Human Chimeric Antibodies to a Tumor-Associated Antigen: Biologic Activity of the Four Human IgG Subclasses," J. Natl. Cancer Inst., 80:1553-1559 (1988).
Shiner, "Immunopathology of the Digestive Apparatus in Infancy," Pediatr. Med. Chir. 4:359-364 (1982) (abstract only).
Shyjan et al., "Human Mucosal Addressin Cell Adhesion Molecule-1 (MAdCAM-1) Demonstrates Structural and Functional Similarities to the .alpha.4.beta.7-Integrin Binding Domains of Murine MadCAM-1, but Extreme Divergence of Mucin-like Sequences," J.of Immunology, 156:2851-2857 (1996).
Silber et al, "Recruitment of Lymphocytes During Cutaneous Delayed Hypersensitivity in Nonhuman Primates is Dependent on E-Selectin and Vascular Cell Adhesion Molecule 1," J. Clin. Invest., 93:1554-1563 (1994).
Springer et al., "Leukocyte Typing V White Cell Differentiation Antigens, vol. II," Oxford University Press, pp. 1443-1456 (1995).
Springer, "The Sensation and Regulation of Interactions with the Extracellular Environment: The Cell Biology of Lymphocyte Adhesion Receptors," Annu. Rev. Cell Biol., 6:359-402 (1990).
Staunton, DE, et al., "Functional cloning of ICAM-2, a Cell Adhesion Ligand for LFA-1 Homologous to ICAM-1," Nature, 339(6219):61-64 (1989).
Streeter, P.R.E.L., et al., "A Tissue-Specific Endothelial Cell Molecule Involved in Lympocyte Homing," Nature, 331:41-46 (1988).
Strober et al., "Chronic Intestinal Inflammation: An Unexpected Outcome in Cytokine or T-Cell Receptor Mutant Mice," Cell, 75:203-205 (1993).
Teague et al., "Integrin .alpha.4.beta.7 Co-Stimulation in Human Peripheral Blood T-Cell Proliferation," Cell Ad. Comm., 2:539-547 (1994).
The Declaration of Steven B. Landau, M.D. Under 37 CFR 1. 132 as filed in U.S. Appl. No. 08/700,737, filed Aug. 15, 1996 (Now U.S. Pat. No. 7,147,851, Issued Dec. 12, 2006.).
Thompson, J.D., et al., "Clustal W: Improving the Sensitivity of Progressive Multiple Sequence Alignment through Sequence Weighting, Position-Specific Gap Penalties and Weight Matrix Choice," Nucleic Acids Res., 22:4673-4680. (1994).
Thorpe, S.J., and T. Feizi, "Species Differences in the Expression of Carbohydrate Differentiation Antigens on Mammalian Blood Cells Revealed by Immunoflurescence with Monoclonal Antibodies," Bioscience Reports, 4:673-685 (1984).
Tidswell et al., "Structure-Function Analysis of the Integrin .beta.7 Subunit," J. Immunol., 159:1497-1505 (1997).
Tiisala et al., ".alpha..sub.E .beta.7 and .alpha.4.beta.7 Integrins Associated with Intraepithelial and Mucosal Homing are Expressed in Macrophages," Eur. J. Immunol., 25:411-417 (1995).
Toruner et al., "Risk Factors for Opportunistic Infections in Patients with Inflammatory Bowel Disease," Gastroenterology, 134:929-936 (2008).
Tromm et al., "Oral Mesalazine for the Treatment of Crohn's Disease: Clinical Efficacy with Respect to Pharmacokinetic Properties," Hepato-Gastroenterology, 46:3124-3135 (1999).
Vadan et al., "The Prevalence of Malnutrition and the Evolution of Nutritional Status in Patients with Moderate to Severe Forms of Crohn's Disease Treated with Infliximab," Clinical Nutrition, 30:86-91 (2011).
Van der Voort et al., "Paracrine Regulation of Germinal Center B Cell Adhesion Through the c-Met-Hepatocyte Growth Factor/Scatter Factor Pathway," J. Exp. Med., 185(12):2121-2131 (1997).
Vasiliauskas, "An Open-Label Pilot Study of Low-Dose Thalidomide in Chronically Active, Steroid-Dependant Crohn's Disease," Gastroenterology, 117:1278-1287 (1999).
Waldmann, "Monoclonal Antibodies in Diagnosis and Therapy," Science, 252:1657-1662 (1991).
Wan et al., "Expression of .alpha.4.beta.7 Integrin on Eosinophils and Modulation of .alpha.4-Integrin-Mediated Eosinophil Adhesion via CD4," Int. Arch. Allergy Immunol., 107:343-344 (1995).
Wang et al., "Fixed Dosing Versus Body Size-Based Dosing of Monoclonal Antibodies in Adult Clinical Trials," Journal of Clinical Pharmacol, 49:1012-1024 (2009).
Webster's II New Riverside Dictionary, The Riverside Publishing Company, p. 755, (1988).
West et al., "Natalizumab Dosage Suspension: Are We Helping or Hurting?" Annals of Neurology, 68(3):395-399 (2010).
Winter et al., "Humanized Antibodies," Immunol. Today, 14(6):243-246 (1993).
Woodside et al., "Specific Inhibition of T Lymphocyte Coactivation by Triggering Integrin .beta. 1 Reveals Convergence of .beta.2 and .beta.7 Signaling Pathways," J. Immunol., 157:700-706 (1996).
Wu, N.W., et al., "Evolutionary Conservation of Tissue-specific Lymphocyte-Endothelial Cell Recognition Mechanisms Involved in Lymphocyte Homing," J. Cell Biol., 107(5):1845-1851 (1998).
Yacyshyn et al., "Crohn's Disease, Ulcerative Colitis, and Normal Intestinal Lymphocytes Express Integrins in Dissimilar Patterns," Gastroenterology, 107:1364-1371 (1994).
Yang et al., "Construction and Adhesion Properties of a Soluble MAdCAM-1-Fe Chimera Expressed in a Baculovirus System: Phylogenetic Conservation of Receptor-Ligand Interation," Scand. J. Immunol., 42:235-247 (1995).
Yang et al., "Involvement of .beta..sub.7 Integrin and Mucosal Addressin Cell Adhesion Molecule-1 (MAdCAM-1) in the Development of Diabetes in Nonobese Diabetic Mice," Diabetes, 46;1542-1547 (1997).
Yuan et al., "Cloning and Sequence Analysis of a Novel b2—Related Integrin Transcript from T Lymphocytes: Homology of Integrin Cysteine-Rich Repeats to Domain III of Laminin B Chains," International Immunology, 2:1097-1108 (1990).
Yuan et al., "Cloning and Sequence Analysis of a Novel b2—Related Integrin Transcript from T Lymphocytes: Homology of Integrin Cysteine-Rich Repeats to Domain III of Laminin B Chains," International Immunology, 3:1373-1374 (1990).
Yuan et al., "Human Peripheral Blood Eosinophils Express a Functional C-Kit Receptorfor Stem Cell Factor that Stimulates Very Late Antigen 4 (VLA-4)-Mediated Cell Adhesion to Fibronectin and Vascular Cell Adhesion Molecule 1 (VCAM01)," J. Exp. Med., 186:313-323 (1997).
"A Study of Ocrelizumab in Patients with Primary Progressive Multiple Sclerosis," downloaded from [https//www.ClinicalTrails.gov/ct2/show/NCT01194570?term+NCT01194570&rank-=1] on Nov. 25, 2015.
Arakawa et al., Amino Acids. Nov. 2007; 33 (4): 587-605. Epub Mar. 16, 2007.
Briskin, Michael J., Integrins as Therapeutic Targets for Inflammatory Disease, Chapter 15, in Leukocyte Trafficking: Molecular Mechanisms, TherapeuticTargets, and Methods. Trafficking. Edited by A. Hamann and B. Engelhardt, publisher John Wiley & Sons, May 12, 2006, pp. 339-370.
Clark. American Gastroenterological Association Consensus Development Conference on the Use of Biologic. Gastroenterology, Jul. 1, 2007; 133:312-339.
ClinicalTrials.gov Archive. Study of Vedolizumab (MLN0002) in Patients With Moderate to Severe Ulcerative Colitis. NCT00783718, Nov. 2, 2008, pp. 1-3.
Archive representation for JAPIC Clinical Trials Information CTI-No. 101133 on May 18, 2010.
Decision and Grounds for Decision Rejecting Opposition issued in connection with Opposition Proceedings of European Patent No. 2704798, Aug. 6, 2019.
E.V.Loftus, "New Data on the Use of Biologic Agents for Crohn's Disease and Ulcerative Colitis: Highlights from the 2009 CCFA Advances in IBD Meeting," Gastroenterology & Hepatology, vol. 6, Issue 2, Supplement 3, (2010).
Entyvio [package insert], Deerfield, IN: Takeda Pharmaceuticals America, Inc.; 2014.
Erbitux [package insert] Princeton, NJ: Bristol-Myers Squibb Co.; 2004.

(56) References Cited

OTHER PUBLICATIONS

Fagg. Takeda results point to novel ulcerative colitis treatment. Evaluate Ltd. Feb. 21, 2012.
FDA Drug Safety Communication: Risk of Progrssive Multifocal Leukoencephalopathy (PML) With The Use of Tysabri (Natalizumab); http://www.fda.gov/Drugs/DrugSafety/PostmarketDrugSafetyInformationPatien-tsand . . . ; U.S. Food and Drug Administration;(Feb. 5, 2010).
Feagan et al., Induction Therapy for Ulcerative Colitis: Results of Gemini I, a Randomized, Placebo-Controlled, Double-Blind, Multicenter Phase 3 Trial. Gastroenterology, May 1, 2012, 142 (5 Suppl. 1):S160-S161 (Abstr.No. 943b).
Feagan et al., "Treatment of Active Crohn's Disease with MLN0002, a Humanized Antibody to the alpha4beta7 Integrin", Clin Gastroenterol Hepatol., Dec. 2008;6(12):1370-7.
Gordon, et al., "A pilot study of treatment of active ulceratve colitis with natalizumab, a humanized monoclonal antibody to alpha-4 integrin," Aliment Pharmacol Ther, 16:699-705 (2002).
Kornbluth et al. "Ulcerative Colitis Practice Guidelines in Adults: American College of Gastroenterology, Practice Parameters Committee," Am. J. Gastroenterol. 105(3): 501-23 (2010).
MacDonald et al. "Natalizumab for induction of remission in Crohn's disease," Cochrane Database Syst Rev. (1): CD006097, 40 pages (2007).
Marshall. LDP-02. Curr Opin in Invest Drugs, Mar. 31, 2001; 2(4):502-504.
Mechcatie, "FDA Allows Tysabri Marketing with Restrictions," Rheumatology News, 31, 2006.
Moss et al. Residual Inflammation and Ulcerative Colitis in Remission. Gastroenterology & Hepatology vol. 10, Issue Mar. 3, 2014, pp. 181-182 (Year: 2014).
Parikh. Long Term Clinical Experience with Vedolizumab (1236). Am J Gastroenterol, (2011); S467.
Parikh A, Wyant T, Clifford DB, Berger JR, Feagan BG, Fox IH, et al., "No increase in JC viremia, lymphocyte count, or ciculating CD34+ hematopoietic progenitor cells after treatment with vedolizumab, a humanized monoclonal antibody to.alpha.4.beta.7 integrin." (2010) presentation.
Parikh et al, "Gastrointestinal Selectivity of Vedolizumab (MLN0002), a Humanized Monoclonal Antibody to the .alpha.4.beta.7 Integrin," P130 poster (2009).
Parikh et al., "No Association Between Vedolizumab Exposure and Serum JC Virus Levels," Inflamm Bowel Disease, 14(suppl S1):S56. Abstract P-147 (2010).
Parker et al., "A Family of .beta.7 Integrins on Human Mucosal Lymphocytes," Proc. Natl. Acad. Sci. USA, 89:1924-1928 (1992).
Pastorelli et al., Emerging drugs for the treatment of ulcerative colitis. Expert Opin. Emerg. Drugs. Sep. 2009.; 14(3): 505-521.
Physician's Desk Reference, Orthoclone OKT, pp. 1971-1974 (1998).
Raptiva [Jun. 10, 2005—Final Draft PI and PPI-Clean copy]. South San Francisco, CA: Genetech Inc.; 2005.
Raptiva [package insert]. South San Francisco, CA: Genetech Inc.; 2009.
ReoPro [package insert], Indianapolis, IN: Eli Lily and Co.; 1997.
Ribas, A. et al., "Phase III Randomized Clinical Trial Comparing Tremelimumab with Standard-of-Care Chemotherapy in Patients with Advanced Melanoma," J. Clinical Oncology, 31(5): 616-622.
Reichert, Janice M., Antibodies to watch in 2010. mAbs 2:1, 84-100; Jan./Feb. 2010.
Riutxan [package Insert]. South San Francisco, CA: Genentech, Inc. 2007.
Rutgeerts et al., "Biological therapies for inflammatory bowel diseases," Gastroenterology, Apr. 2009, 136(4):1182-1197.
Sands et al., Safety and Tolerability of Concurrent Natalizumab Treatment for Patients with Crohn's Disease Not in Remission While Receiving Infliximab. Inflamm Bowel Dis, Jan. 1, 2007, 13(1):2-11.
Simulect [package insert]. East Hanover, NJ: Novartis Pharmaceuticals Corp.: 1998.
Soler Dulce et al., The Binding Specificity and Selective Antagonism of Vedolizumab, an Anti-alpha(4)beta(7) Integrin Therapeutic Antibody in Development for Inflammatory Bowel Diseases. Journal of Pharmacology and Experimental Therapeutics, American Society for Pharmacology and Experimental Therapeutics, US, Sep. 1, 2009; 330(3): 864-875.
Soler-Ferran and Briskin. Integrin alpha4beta7 Antagonists: Activities, Mechanisms of Action and Therapeutic Prospects. Current Immunology Reviews, Mar. 1, 2012; 8:118-134.
Sorbera et al., Natalizumab. Treatment of IBD, treatment of multiple sclerosis: AN100226, AntegrenTM. Drugs of the Future, Barcelona, ES, Sep. 1, 2000; 25(9): 917- 921.
Takeda Press Release, Feb. 21, 2012.
"Takeda Initiates Two Phase III Studies with Vedolizumab (MLN0002) in Patients with Inflammatory Bowel Disease—Simultaneous Studies to Investigate Novel Therapy for Ulcerative Colitis and Crohn's Disease," 2 pages, Jan. 22, 2009.
Tysabri [package insert] and Final Med Guide; Cambridge, MA: Biogen Idec Inc.; 2006.
Tysabri [package insert], Cambridge, MA: Biogen Idec Inc.; 2008, revised.
Tysabri® Risk Minimization Action Plan: Summary of Touch; Department of Health & Human Services: pp. 1-5.
Vectibix [package insert], Thousand Oaks, CA: Amgen; 2006.
Williams and Goh, Investigational new drugs in the treatment of inflammatory bowel disease: a review. J Exp Pharmacol, Feb. 27, 2011; 3:13-19.
Yervoy [package insert]. Princeton, NJ: Bristol-Myers Squibb Co.; 2011.
Zenapax [package insert]. Nutley, NJ: Roche Pharmaceuticals; 1997.
Clinical Trials.gov—NCT01224171 on Dec. 22, 2010 Study of Vedolizumab (MLN0002) in Patients With Moderate to Severe Crohn's Disease.
ClinicalTrials.gov—NCT00783692 on Mar. 17, 2011. Study of Vedolizumab (MLN0002) in Patients With Moderate to Severe Crohn's Disease.
Feagan et al. (2005) New England Journal of Medicine 352(24): 2499-2507.
Tilg et al. (2010) Curr Opin Invest Drugs 11(11): 1295-1304.
Springer, "Traffic Signals for Lymphocyte Recirculation and Leukocyte Emigration: The Multistep Paradigm," Cell, 76:301-314 (1994).
Tang, D.G., et al., "Phenotypic Properties of Cultured Tumor Cells: Integrin .alpha.11.beta.3 Expression, Tumor-Cell-Induced Platelet Aggregation, and Tumor-Cell Adhesion to Endothelium as Important Parameters of Experimental Metastasis," Int. J.Cancer, 54:338-347 (1993).
Taub et al., "Monocyte Chemotactic Protein-1 (MCP-1), -2 and -3 are Chemotactic for Human T Lymphocytes," J. of Clin. Investigation, 95:1370-1376 (1995).
Fasanmade et al. Population pharmacokinetic analysis of infliximab in patients with ulcerative colitis. (Eur J Clin Pharmacol (2009) 65: 1211-1228).
Mould et al. Pharmacokinetics and Pharmacodynamics of Monoclonal Antibodies. (BioDrugs. Feb. 1, 2010;24(1):23-39).
Reenaers et al., Ther Adv Gastroenterol., 2010, 3(2): 99-106.
Subrata Ghosh et al., "Anti-adhesion molecule therapy for inflammatory bowel disease", Therapeutic Advances in Gastroenterology, 2010, 3(4), pp. 239-258, published on Jul. 3, 2010.
Francesco Lanzarotto et al., "Novel treatment options for inflammatory bowel disease: targeting alpha4 integrin", Drugs, 2006, 66(9), pp. 1179-1189, published on Dec. 31, 2006.
Yvette Leung et al., "Anti-Adhesion Molecule Strategies for Crohn Disease", Biodrugs, 2008, 22(4): pp. 259-264, published on Jul. 31, 2008.
MJ Carter et al., "Guidelines for the management of inflammatory bowel disease in adults", Gut, 2004, 53: pp. 1-16, published on Sep. 30, 2004.
Travis SP et al., "European evidence based consensus on the diagnosis and management of Crohn's disease: definitions and diagnosis", Gut., 2006, 55 (Suppl1): pp. i16-i35, published on Mar. 31, 2006.

(56) References Cited

OTHER PUBLICATIONS

Best WR., "Predicting the Crohn's disease activity index from the Harvey-Bradshaw Index", Inflamm Bowel Dis., 2006, 12(4): pp. 304-310, published on Apr. 30, 2006.
Thia K et al., "Short CDAI: development and validation of a shortened and simplified Crohn's disease activity index.", Inflamm Bowel Dis., 2011, 17(1): pp. 105-111, published on Jul. 13, 2010.
Bernstein CN, et al. World Gastroenterology Organization Practice Guidelines for the diagnosis and management of IBD in 2010. Inflamm Bowel Dis. Jan. 2010;16(1):112-24.
Burger D, Travis S. Conventional medical management of inflammatory bowel disease. Gastroenterology. May 2011;140(6):1827-1837.e2.
NHS-Health Research Authority. Open-label study of MLN0002 in Ulcerative Colitis & Crohn's Disease. pp. 1-4, 2010.
Gionata Fiorino et al., "Leukocyte traffic control: a novel therapeutic strategy for inflammatory bowel disease", Expert Rev. Clin. Immunol. 6(4), 567-572 (2010).
Decision of Examination on Request for Invalidation (Decision No. 587108) for Chinese Patent No. 201711310404.0. Date of Decision Sept. 8, 2025 (English translation).
Baumgart, "The diagnosis and treatment of Crohn's disease and ulcerative colitis". Dtsch Arztebl Int. Feb. 2009; 106(8):123-33.
ClinicalTrials.gov entry of Dec. 23, 2010 for NCT00619489.
ClinicalTrials.gov entry for NCT00783718 (Mar. 4, 2010, ("Version 13")).
"An Open-label Study of Vedolizumab (MLN0002) in Participants With Ulcerative Colitis and Crohn's Disease (Gemini Lts)", Version 8, NCT00790933, available on the ClinicalTrials.gov website on Dec 22, 2010.
Clinical trial protocol version dated Dec. 10, 2010 for Japanese study jRCT2080221099, obtained from https://jrct. mhlw.go.jp/pages/endetail/39593/jRCT/3 on Sep. 30, 2025.
ClinicalTrials.gov entry of Mar. 2, 2012 for NCT00783718.
ClinicalTrials.gov entry of Mar. 2, 2012 for NCT00783692.
ClinicalTrials.gov entry of Mar. 21, 2011 for NCT00783718.
ClinicalTrials.gov entry of Mar. 21, 2011 for NCT00783692.
Crohn's Disease Activity Index from Italian Group for Inflammatory Bowel Disease (IG-IBD) (see https://www. igibdscores.it/en/info-cdal.php).
FDA label for natalizumab; Mar. 2011.
FDA pharmacology review for natalizumab (approved Nov. 2004); from https://www.accessdata.fda.gov/drugsatfda_docs/nda/2004/125104s000_natalizumab.cfm; date created Mar. 8, 2005.
Ghosh S, et al. Natalizumab for active Crohn's disease. N Engl J Med. 348(1):24-32, Jan. 2, 2003.
"A Phase 3, Randomized, Placebo Controlled, Blinded, Multicenter Study of the Induction and Maintenance of Clinical Response and Remission by MLN0002 in Patients with Moderate to Severe Ulcerative Colitis", Central Committee on Research Involving Human Subjects (Centrale Commissie Mensgebonden Onderzoek, CCMO) register; ID NL-OMON33523, Published: Feb. 11, 2009; last updated Sep. 1, 2025.
"A Phase 3, Randomized, Placebo Controlled, Blinded, Multicenter Study of the Induction of Clinical Response and Remission by Vedolizumab in Patients With Moderate to Severe Crohn's Disease", Central Committee on Research Involving Human Subjects (Centrale Commissie Mensgebonden Onderzoek, CCMO) register; ID: NL-OMON36532, Published: Nov. 5, 2010; last updated Sep. 1, 2025.
"A Phase 3, Open-label Study to Determine the Long-Term Safety and Efficacy of Vedolizumab (MLN0002) in Patients with Ulcerative Colitis and Crohn's Disease", Central Committee on Research Involving Human Subjects (Centrale Commissie Mensgebonden Onderzoek, CCMO) register; ID: NLOMON43573, Published: Feb. 11, 2009; last updated Sep. 1, 2025.
Lewis JD. The utility of biomarkers in the diagnosis and therapy of inflammatory bowel disease. Gastroenterology. May 2011;140(6):1817-1826.e2. doi: 10.1053/j.gastro.2010.11.058.
Milch et al., Inflammatory Bowel Diseases, 17(suppl 2):S54, Abstract P-136, Dec. 1, 2011.
Milch et al., "Vedolizumab Does Not Reduce theCD4+:CD8+ Ratio in the CSF of Healthy Volunteers: 1221". American Journal of Gastroenterology 106():p $460-S461, Oct. 2011.
Partial Mayo Score from Italian Group for Inflammatory Bowel Disease (IG-IBD) (see https://www.igibdscores.it/en/info-mayo-partial.php).
Patentee's letter from examination dated Mar. 16, 2021 for EP18150968.8.
Rutgeerts et al., "Infliximab for Induction and Maintenance Therapy for Ulcerative Colitis" N Engl J Med. Dec 2005. 8 353;23: 2462.
Sandborn et al., "Natalizumab induction and maintenance therapy for Crohn's disease", N Engl J Med. Nov. 3, 2005;353(18):1912-25.
Sandborn WJ, Hanauer SB. Infliximab in the treatment of Crohn's disease: a user's guide for clinicians. Am J Gastroenterol. Dec 2002;97(12):2962-72.
Vedolizumab, Drug Bank entry, accessed on Dec. 2, 160252.
The WHO Drug Information for vedolizumab, 2008.
"GEMINI programme provides first boost for Takeda's vedolizumab in ulcerative colitis". Scrip, Citeline Commercial, Published on Feb. 22, 2012.
Emea, Committee for Medicinal Products for Human Use: Guideline on the development of new medical products for the treatment of Crohn's disease (Feb. 22, 2007).
Opposition to EP3329965 dated Dec. 17, 2025 (Brand Murray Fuller LLP).
Opposition to EP3329965 dated Dec. 18, 2025 (Abel and Imray LLP).
Opposition to EP3329965 dated Dec. 18, 2025 (Fresenius Kabi SwissBiosim GmbH).
Opposition to EP3329965 dated Dec. 18, 2025 (Advanz Pharma Services (UK) Ltd).
Opposition to EP3329965 dated Dec. 19, 2025 (Ulrich Storz—Michalski Huttermann and Partner).
Opposition to EP3329965 dated Dec. 19, 2025 (Graf von Stosch Patentanwaltsgesellschaft mbH)).

* cited by examiner

FIG. 1A

New LDP02 Heavy DNA – – contains cloning sites (lower case),Kozak sequence (upper case) and Leader (lower case)

gaattctcgagatcgatCTCACCatgggatggagctgtatcatcctcttcttggtagcaacagctacaggtgtccactcccag
gtgCAATTGGTGCAGTCTGGGGCTGAGGTTAAGAAGCCTGGGGCTTCAGTGAA
GGTGTCCTGCAAGGGTTCTGGCTACACCTTCACCAGCTACTGGATGCATTGGG
TGAGGCAGGCGCCTGGCCAACGTCTAGAGTGGATCGGAGAGATTGATCCTTC
TGAGAGTAATACTAACTACAATCAAAAATTCAAGGGACGCGTCACATTGACT
GTAGACATTTCCGCTAGCACAGCCTACATGGAGCTCTCCAGCCTGAGATCTG
AGGACACTGCGGTCTACTATTGTGCAAGAGGGGGTTACGACGGATGGGACTA
TGCTATTGACTACTGGGGTCAAGGCACCCTGGTCACCGTCAGCTCAGCCTCCA
CCAAGGGCCCATCGGTCTTCCCCCTGGCACCCTCCTCCAAGAGCACCTCTGGG
GGCACAGCGGCCCTGGGCTGCCTGGTCAAGGACTACTTCCCCGAACCGGTGA
CGGTGTCGTGGAACTCAGGCGCCCTGACCAGCGGCGTGCACACCTTCCCGGC
TGTCCTACAGTCCTCAGGACTCTACTCCCTCAGCAGCGTGGTGACCGTGCCCT
CCAGCAGCTTGGGCACCCAGACCTACATCTGCAACGTGAATCACAAGCCCAG
CAACACCAAGGTGGACAAGAAAGTTGAGCCCAAATCTTGTGACAAAACTCAC
ACATGCCCACCGTGCCCAGCACCTGAACTCGCGGGGGCACCGTCAGTCTTCC
TCTTCCCCCCAAAACCCAAGGACACCCTCATGATCTCCCGGACCCCTGAGGTC
ACATGCGTGGTGGTGGACGTGAGCCACGAAGACCCTGAGGTCAAGTTCAACT
GGTACGTGGACGGCGTGGAGGTGCATAATGCCAAGACAAAGCCGCGGGAGG
AGCAGTACAACAGCACGTACCGTGTGGTCAGCGTCCTCACCGTCCTGCACCA
GGACTGGCTGAATGGC AAGGAGTACAAGTGCAAGGTCTCCAACAAAGCCCTCCCAGCCCCCATCGAGA
AAACCATCTCCAAAGCCAAAGGGCAGCCCCGAGAACCACAGGTGTACACCCT
GCCCCCATCCCGGGATGAGCTGACCAAGAACCAGGTCAGCCTGACCTGCCTG
GTCAAAGGCTTCTATCCCAGCGACATCGCCGTGGAGTGGGAGAGCAATGGGC
AGCCGGAGAACAACTACAAGACCACGCCTCCCGTGCTGGACTCCGACGGCTC
CTTCTTCCTCTACAGCAAGCTCACCGTGGACAAGAGCAGGTGGCAGCAGGGG
AACGTCTTCTCATGCTCCGTGATGCATGAGGCTCTGCACAACCACTACACGCA
GAAGAGCCTCTCCCTGTCTCCGGGTAAAtaatctagagca

New LDP02 Heavy Protein (space between VHL, VH and Human IgG1-FcRmut)
MGWSCIILFLVATATGVHS
QVQLVQSGAEVKKPGASVKVSCKGSGYTFTSYWMHWVRQAPGQRLEWIGEIDP
SESNTNYNQKFKGRVTLTVDISASTAYMELSSLRSEDTAVYYCARGGYDGWDY
AIDYWGQGTLVTVSS
ASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCP
PCPAPELAGAPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIEKTI
SKAKGQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKSLSLS
PGK

FIG. 1B

FIG. 2

New LDP02 Light DNA – contains cloning sites (lower case),Kozak sequence (upper case) and Leader (lower case)

gaattctcgagatcgatCTCACCatgggatggagctgtatcatcctcttcttggtagcaacagctacaggtgtccactccgat
GTAGTGATGACTCAAAGTCCACTCTCCCTGCCTGTCACCCCTGGAGAACCAGC
TTCTATCTCTTGCAGGTCTAGTCAGAGTCTTGCAAAGAGTTATGGGAACACCT
ATTTGTCTTGGTACCTGCAGAAGCCTGGCCAGTCTCCACAGCTCCTCATCTAT
GGGATTTCCAACAGATTTTCTGGGGTGCCAGACAGGTTCAGTGGCAGTGGTT
CAGGGACAGATTTCACACTCAAGATCTCGCGAGTAGAGGCTGAGGACGTGGG
AGTGTATTACTGCTTACAAGGTACACATCAGCCGTACACGTTCGGACAGGGG
ACCAAGGTGGAGATCAAGCGTACGGTGGCTGCACCATCTGTCTTCATCTTCCC
GCCATCTGATGAGCAGTTGAAATCTGGAACTGCCTCTGTTGTGTGCCTGCTGA
ATAACTTCTATCCCAGAGAGGCCAAAGTACAGTGGAAGGTGGATAACGCCCT
CCAATCGGGTAACTCCCAGGAGAGTGTCACAGAGCAGGACAGCAAGGACAG
CACCTACAGCCTCAGCAGCACCCTGACCCTGAGCAAAGCAGACTACGAGAAA
CACAAAGTCTACGCCTGCGAAGTCACCCATCAGGGCCTGAGCTCGCCCGTCA
CAAAGAGCTTCAACAGGGGAGAGTGTtagtctagagcagc

New LDP02 Light Protein (space between VKL, VK and Human C Kappa)

MGWSCIILFLVATATGVHS
DVVMTQSPLSLPVTPGEPASISCRSSQSLAKSYGNTYLSWYLQKPGQSPQLLIYGI
SNRFSGVPDRFSGSGSGTDFTLKISRVEAEDVGVYYCLQGTHQPYTFGQGTKVEI
K
RTVAAPSVFIFPPSDEQLKSGTASVVCLLNNFYPREAKVQWKVDNALQSGNSQE
SVTEQDSKDSTYSLSSTLTLSKADYEKHKVYACEVTHQGLSSPVTKSFNRGEC

FIG. 3

PAIRWISE newMLN02-no sig LDP-02-no sig.txt

```
A 1 DVVMTQSPLSLPVTPGEPASISCRSSQSLAKSYGNTYLSWYLQKPGQSPQ 50
    ||||||||||||||||||||||||||||||||||||||||||||||||||
B 1 DVVMTQSPLSLPVTPGEPASISCRSSQSLAKSYGNTYLSWYLQKPGQSPQ 50
             .         .         .         .         .
 51 LLIYGISNRFSGVPDRFSGSGSGTDFTLKISRVEAEDVGVYYCLQGTHQP 100
    ||||||||||||||||||||||||||||||||||||||||||||||||||
 51 LLIYGISNRFSGVPDRFSGSGSGTDFTLKISRVEAEDVGVYYCLQGTHQP 100
             .         .         .         .         .
101 YTFGQGTKVEIKRTVAAPSVFIFPPSDEQLKSGTASVVCLLNNFYPREAK 150
    |||||||||||||  |||||||||||||||||||||||||||||||||||
101 YTFGQGTKVEIKRADAAPSVFIFPPSDEQLKSGTASVVCLLNNFYPREAK 150
             .         .         .         .         .
151 VQWKVDNALQSGNSQESVTEQDSKDSTYSLSSTLTLSKADYEKHKVYACE 200
    ||||||||||||||||||||||||||||||||||||||||||||||||||
151 VQWKVDNALQSGNSQESVTEQDSKDSTYSLSSTLTLSKADYEKHKVYACE 200
             .
201 VTHQGLSSPVTKSFNRGEC 219
    |||||||||||||||||||
201 VTHQGLSSPVTKSFNRGEC 219
```

FIG. 4

Pairwise Hum kappa-const MI:Mur kappa-const.txt

```
A 1 rtvaapsvfifppsdeqlksgtasvvcllnnfypreakvqwkvdnalqsg 50
    |  |||.| ||||| ||| || ||||| ||||||::  |.||:| . .
B 1 radaaptvsifppsseqltsggasvvcflnnfypkdinvkwkidgserqn 50

             .         .         .         .         .
 51 nsqesvteqdskdstyslsstltlskadyekhkvyacevthqglsspvtk 100
        | |:|||||||||:||||||.| :||:|  | || ||.  .||: |
 51 gvlnswtdqdskdstysmsstltltkdeyerhnsytceathktstspivk 100

101 sfnrgec 107
    |||| ||
101 sfnrnec 107
```

pLKTOK38D

FIG. 7

GM607'Cl antibody kappa light chain variable region

SEQ ID NO: 14

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Tyr Asn Tyr Leu Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Ala
85 90 95

Leu Gln Thr Pro Gln Thr Phe Gly Gln Gly Thr Lys Val Glu Ile Lys
100 105 110

21/28'CL antibody heavy chain variable region

SEQ ID NO: 15

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Ala Met His Trp Val Arg Gln Ala Pro Gly Gln Arg Leu Glu Trp Met
35 40 45

Gly Trp Ile Asn Ala Gly Asn Gly Asn Thr Lys Tyr Ser Gln Lys Phe
50 55 60

Gln Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Gly Gly Tyr Tyr Gly Ser Gly Ser Asn Tyr Trp Gly Gln Gly
100 105 110

Thr Leu Val Thr Val Ser Ser
115

SEQUENCE LISTING

```
Sequence total quantity: 15
SEQ ID NO: 1            moltype = DNA  length = 1445
FEATURE                 Location/Qualifiers
misc_feature            1..1445
                        note = Description of Artificial Sequence: Synthetic
                         polynucleotide
source                  1..1445
                        mol_type = other DNA
                        organism = synthetic construct
SEQUENCE: 1
gaattctcga gatcgatctc accatgggat ggagctgtat catcctcttc ttggtagcaa  60
cagctacagg tgtccactcc caggtgcaat tggtgcagtc tggggctgag gttaagaagc  120
ctggggcttc agtgaaggtg tcctgcaagg gttctggcta caccttcacc agctactgga  180
tgcattgggt gaggcaggcg cctggccaac gtctagagtg gatcggagag attgatcctt  240
ctgagagtaa tactaactac aatcaaaaat tcaagggacg cgtcacattg actgtagaca  300
tttccgctag cacagcctac atggagctct ccagcctgag atctgaggac actgcggtct  360
actattgtgc aagagggggt tacgacggat gggactatgc tattgactac tggggtcaag  420
gcaccctggt caccgtcagc tcagcctcca ccaagggccc atcggtcttc cccctggcac  480
cctcctccaa gagcacctct gggggcacag cggccctggg ctgcctggtc aaggactact  540
tccccgaacc ggtgacggtg tcgtggaact caggcgccct gaccagcggc gtgcacacct  600
tcccggctgt cctacagtcc tcaggactct actccctcag cagcgtggtg accgtgccct  660
ccagcagctt gggcacccag acctacatct gcaacgtgaa tcacaagccc agcaacacca  720
aggtggacaa gaaagttgag cccaaatctt gtgacaaaac tcacacatgc ccaccgtgcc  780
cagcacctga actcgcgggg gcaccgtcag tcttcctctt ccccccaaaa cccaaggaca  840
ccctcatgat ctcccggacc cctgaggtca catgcgtggt ggtggacgtg agccacgaag  900
accctgaggt caagttcaac tggtacgtgg acggcgtgga ggtgcataat gccaagacaa  960
agccgcggga ggagcagtac aacagcacgt accgtgtggt cagcgtcctc accgtcctgc  1020
accaggactg gctgaatggc aaggagtaca agtgcaaggt ctccaacaaa gccctcccag  1080
cccccatcga gaaaaccatc tccaaagcca aagggcagcc ccgagaacca caggtgtaca  1140
ccctgccccc atcccgggat gagctgacca agaaccaggt cagcctgacc tgcctggtca  1200
aaggcttcta tcccagcgac atcgccgtgg agtgggagag caatgggcag ccggagaaca  1260
actacaagac cacgcctccc gtgctggact ccgacggctc cttcttcctc tacagcaagc  1320
tcaccgtgga caagagcagg tggcagcagg ggaacgtctt ctcatgctcc gtgatgcatg  1380
aggctctgca caaccactac acgcagaaga gcctctccct gtctccgggt aaataatcta  1440
gagca                                                              1445

SEQ ID NO: 2            moltype = AA  length = 470
FEATURE                 Location/Qualifiers
REGION                  1..470
                        note = Description of Artificial Sequence: Synthetic
                         polypeptide
source                  1..470
                        mol_type = protein
                        organism = synthetic construct
SEQUENCE: 2
MGWSCIILFL VATATGVHSQ VQLVQSGAEV KKPGASVKVS CKGSGYTFTS YWMHWVRQAP  60
GQRLEWIGEI DPSESNTNYN QKFKGRVTLT VDISASTAYM ELSSLRSEDT AVYYCARGGY  120
DGWDYAIDYW GQGTLVTVSS ASTKGPSVFP LAPSSKSTSG GTAALGCLVK DYFPEPVTVS  180
WNSGALTSGV HTFPAVLQSS GLYSLSSVVT VPSSSLGTQT YICNVNHKPS NTKVDKKVEP  240
KSCDKTHTCP PCPAPELAGA PSVFLFPPKP KDTLMISRTP EVTCVVVDVS HEDPEVKFNW  300
YVDGVEVHNA KTKPREEQYN STYRVVSVLT VLHQDWLNGK EYKCKVSNKA LPAPIEKTIS  360
KAKGQPREPQ VYTLPPSRDE LTKNQVSLTC LVKGFYPSDI AVEWESNGQP ENNYKTTPPV  420
LDSDGSFFLY SKLTVDKSRW QQGNVFSCSV MHEALHNHYT QKSLSLSPGK             470

SEQ ID NO: 3            moltype = DNA  length = 751
FEATURE                 Location/Qualifiers
misc_feature            1..751
                        note = Description of Artificial Sequence: Synthetic
```

```
                         polynucleotide
source                  1..751
                        mol_type = other DNA
                        organism = synthetic construct
SEQUENCE: 3
gaattctcga gatcgatctc accatgggat ggagctgtat catcctcttc ttggtagcaa  60
cagctacagg tgtccactcc gatgtagtga tgactcaaag tccactctcc ctgcctgtca  120
cccctggaga accagcttct atctcttgca ggtctagtca gagtcttgca aagagttatg  180
ggaacaccta tttgtcttgg tacctgcaga agcctggcca gtctccacag ctcctcatct  240
atgggatttc caacagattt tctggggtgc cagacaggtt cagtggcagt ggttcaggga  300
cagatttcac actcaagatc tcgcgagtag aggctgagga cgtgggagtg tattactgct  360
tacaaggtac acatcagccg tacacgttcg gacaggggac caaggtggag atcaagcgta  420
cggtggctgc accatctgtc ttcatcttcc cgccatctga tgagcagttg aaatctggaa  480
ctgcctctgt tgtgtgcctg ctgaataact tctatcccag agaggccaaa gtacagtgga  540
aggtggataa cgccctccaa tcgggtaact cccaggagag tgtcacagag caggacagca  600
aggacagcac ctacagcctc agcagcaccc tgaccctgag caaagcagac tacgagaaac  660
acaaagtcta cgcctgcgaa gtcacccatc agggcctgag ctcgcccgtc acaaagagct  720
tcaacagggg agagtgttag tctagagcag c                                 751

SEQ ID NO: 4            moltype = AA  length = 238
FEATURE                 Location/Qualifiers
REGION                  1..238
                        note = Description of Artificial Sequence: Synthetic
                         polypeptide
source                  1..238
                        mol_type = protein
                        organism = synthetic construct
SEQUENCE: 4
MGWSCIILFL VATATGVHSD VVMTQSPLSL PVTPGEPASI SCRSSQSLAK SYGNTYLSWY  60
LQKPGQSPQL LIYGISNRFS GVPDRFSGSG SGTDFTLKIS RVEAEDVGVY YCLQGTHQPY  120
TFGQGTKVEI KRTVAAPSVF IFPPSDEQLK SGTASVVCLL NNFYPREAKV QWKVDNALQS  180
GNSQESVTEQ DSKDSTYSLS STLTLSKADY EKHKVYACEV THQGLSSPVT KSFNRGEC    238

SEQ ID NO: 5            moltype = AA  length = 219
FEATURE                 Location/Qualifiers
REGION                  1..219
                        note = Description of Artificial Sequence: Synthetic
                         polypeptide
source                  1..219
                        mol_type = protein
                        organism = synthetic construct
SEQUENCE: 5
DVVMTQSPLS LPVTPGEPAS ISCRSSQSLA KSYGNTYLSW YLQKPGQSPQ LLIYGISNRF  60
SGVPDRFSGS GSGTDFTLKI SRVEAEDVGV YYCLQGTHQP YTFGQGTKVE IKRADAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 6            moltype = AA  length = 107
FEATURE                 Location/Qualifiers
source                  1..107
                        mol_type = protein
                        organism = Homo sapiens
SEQUENCE: 6
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC                107

SEQ ID NO: 7            moltype = AA  length = 107
FEATURE                 Location/Qualifiers
source                  1..107
                        mol_type = protein
                        organism = Mus sp.
SEQUENCE: 7
RADAAPTVSI FPPSSEQLTS GGASVVCFLN NFYPKDINVK WKIDGSERQN GVLNSWTDQD  60
SKDSTYSMSS TLTLTKDEYE RHNSYTCEAT HKTSTSPIVK SFNRNEC                107

SEQ ID NO: 8            moltype = AA  length = 5
FEATURE                 Location/Qualifiers
source                  1..5
                        mol_type = protein
                        organism = Mus sp.
SEQUENCE: 8
SYWMH                                                             5

SEQ ID NO: 9            moltype = AA  length = 17
FEATURE                 Location/Qualifiers
source                  1..17
                        mol_type = protein
                        organism = Mus sp.
SEQUENCE: 9
```

-continued

```
EIDPSESNTN YNQKFKG                                                17

SEQ ID NO: 10          moltype = AA  length = 12
FEATURE                Location/Qualifiers
source                 1..12
                       mol_type = protein
                       organism = Mus sp.
SEQUENCE: 10
GGYDGWDYAI DY                                                     12

SEQ ID NO: 11          moltype = AA  length = 16
FEATURE                Location/Qualifiers
source                 1..16
                       mol_type = protein
                       organism = Mus sp.
SEQUENCE: 11
RSSQSLAKSY GNTYLS                                                 16

SEQ ID NO: 12          moltype = AA  length = 7
FEATURE                Location/Qualifiers
source                 1..7
                       mol_type = protein
                       organism = Mus sp.
SEQUENCE: 12
GISNRFS                                                           7

SEQ ID NO: 13          moltype = AA  length = 9
FEATURE                Location/Qualifiers
source                 1..9
                       mol_type = protein
                       organism = Mus sp.
SEQUENCE: 13
LQGTHQPYT                                                         9

SEQ ID NO: 14          moltype = AA  length = 111
FEATURE                Location/Qualifiers
source                 1..111
                       mol_type = protein
                       organism = Homo sapiens
SEQUENCE: 14
DIVMTQSPLS LPVTPGEPAS ISCRSSQSLL HSNGYNYLDW YLQKPGQSPQ LLIYLGSNRA  60
SGVPDRFSGS GSGTDFTLKI SRVEAEDVGV YYCMQALQTP QTFGQGKVEI K           111

SEQ ID NO: 15          moltype = AA  length = 119
FEATURE                Location/Qualifiers
source                 1..119
                       mol_type = protein
                       organism = Homo sapiens
SEQUENCE: 15
QVQLVQSGAE VKKPGASVKV SCKASGYTFT SYAMHWVRQA PGQRLEWMGW INAGNGNTKY  60
SQKFQGRVTI TRDTSASTAY MELSSLRSED TAVYYCARGG YYGSGSNYWG QGTLVTVSS   119
```

METHODS FOR TREATMENT USING ANTI-α4β7 ANTIBODY

RELATED APPLICATIONS

This application is a continuation of U.S. Non-Provisional Ser. No. 18/778,906 filed on Jul. 19, 2024, which is a continuation of U.S. Non-Provisional Ser. No. 16/743,813 filed on Jan. 15, 2020, which is a continuation of U.S. Non-Provisional patent application Ser. No. 15/678,744 filed on Aug. 16, 2017, which is a continuation of U.S. Non-Provisional application Ser. No. 14/114,832 filed on Feb. 25, 2014, now U.S. Pat. No. 9,764,033 issued on Sep. 19, 2017, which is a National Stage Entry of International Application No. PCT/US2012/036072 filed on May 2, 2012, which claims the benefit of U.S. Provisional Application 61/585,859 filed on Jan. 12, 2012, U.S. Provisional Application 61/550,545 filed on Oct. 24, 2011, and U.S. Provisional Application 61/481,533 filed on May 2, 2011. The entire contents of the foregoing applications are hereby incorporated by reference.

SEQUENCE LISTING

The instant application contains a Sequence Listing which has been submitted electronically in XML file format via EFS-Web and is hereby incorporated by reference in its entirety. Said XML copy, created on Oct. 21, 2024, is named T103022_1010US_C12T1 SL.xml and is 19,535 bytes in size.

BACKGROUND OF THE INVENTION

Advances in biotechnology have made it possible to produce a variety of proteins for pharmaceutical applications using recombinant DNA techniques. Because proteins are larger and more complex than traditional organic and inorganic drugs (i.e. possessing multiple functional groups in addition to complex three-dimensional structures), the formulation of such proteins poses special problems. For a protein to remain biologically active, a formulation must preserve the conformational integrity of at least a core sequence of the protein's amino acids, while at the same time protecting the protein's multiple functional groups from degradation. Proteins may suffer from a lack of stability, and monoclonal and polyclonal antibodies in particular may be relatively unstable (See e.g., Wang et al., *J. Pharm Sci.* 96:1-26 (2007)). A large number of formulation options are available, and not one approach or system is suitable for all proteins. Several factors to be considered have been reported (See e.g., Wang et al).

Numerous characteristics may affect a protein's stability. In fact, even in the case of purified antibodies, the antibody structures may be heterogeneous, which further complicates the formulation of such systems. Moreover, the excipients included in antibody formulations preferably minimize any potential immune response.

In the case of antibodies, preservation of the conformational integrity is even more important. Degradation pathways for proteins can involve chemical instability (i.e., any process which involves modification of the protein by bond formation or cleavage resulting in a new chemical entity) or physical instability (i.e., changes in the higher order structure of the protein). Chemical instability is manifested in, for example, deamidation, isomerization, hydrolysis, oxidation, fragmentation, glycan beta elimination or disulfide exchange. Physical instability can result from denaturation, aggregation, precipitation or adsorption, for example. The four most common protein degradation pathways are protein fragmentation, aggregation, deamidation, and oxidation. Consequences of chemical or physical instability of therapeutic protein include a lowering of the effective administered dose, decreased safety of the therapy due to, for example irritation or immunological reactivity, and more frequent manufacturing due to short shelf life.

Freeze-drying is a commonly employed technique for preserving proteins; freeze-drying serves to remove water from the protein preparation of interest. Freeze-drying, or lyophilization, is a process by which the material to be dried is first frozen and then the ice or frozen solvent is removed by sublimation under vacuum. Excipients can be included in the pre-lyophilized formulation to stabilize proteins during the lyophilization process and/or to improve the stability of the lyophilized protein formulation (Pikal M., *Biopharm.* 3(9)26-30 (1990) and Arakawa et al. *Pharm. Res.* (3):285-291 (1991)).

Several publications have disclosed generally various methods of treating inflammatory bowel diseases, and provided dosing schemes for administration of agents designed to treat inflammatory bowel disease. For example, WO 96/24673 discloses mucosal vascular addressins and treatment of diseases associated with leukocyte recruitment to the gastrointestinal tract as a result of leukocyte binding to cells expressing MAdCAM. U.S. 2005/0095238 describes methods of treating a disease associated with leukocyte infiltration of mucosal tissue and administration to a human an effective amount of a human or humanized immunoglobulin or antigen binding fragment having binding specificity for α4β7 integrin. U.S. 2005/0095238 further describes various doses (e.g. 0.15, about 0.5, about 1.0, about 1.5 or about 2.0 mg immunoglobulin or fragment per kg body weight) and various intervals between doses (7, 14, 21, 28, or 30 days). However, the aforementioned patents and publications do not disclose specific formulations of the anti-α4β7 antibody or the specific doses and dose regimens described and claimed herein. Importantly, the aforementioned patents do not disclose formulations, doses, and dose regimens that provide for the methods of treatment (supported by clinical trial data) described and claimed herein.

The antibody formulations of the present invention may be useful for inhibiting leukocyte binding to cells expressing MAdCAM and therefore aid in treatment of inflammatory bowel diseases in patients. There is, accordingly, an urgent need to discover suitable dosages and dosing schedules of these compounds, and to develop formulations, preferably intravenous formulations, which give rise to steady, therapeutically effective blood levels of the antibody formulations over an extended period of time in a stable and convenient form.

SUMMARY OF THE INVENTION

The invention relates to the identification of a non-reducing sugar and at least one amino acid, as useful excipients for formulating anti-α4β7 antibody formulations whose instability makes them susceptible to deamidation, oxidation, isomerization and/or aggregation. The formulation improves stability, reduces aggregate formation and retards degradation of the antibody therein.

Thus, in a first aspect, the invention relates to a stable formulation comprising a mixture of a non-reducing sugar, an anti-α4β7 antibody and at least one free amino acid, and the molar ratio of non-reducing sugar to anti-α4β7 antibody (mole:mole) is greater than 600:1. The formulation may be a liquid formulation or a dry formulation (e.g., lyophilized). The formulation can also contain a buffering agent. In some embodiments, the non-reducing sugar is mannitol, sorbitol, sucrose, trehalose, or any combination thereof.

In some embodiments, the free amino acid of the formulation is histidine, alanine, arginine, glycine, glutamic acid, or any combination thereof. The formulation can comprise between about 50 mM to about 175 mM of free amino acid. The formulation can comprise between about 100 mM and about 175 mM of free amino acid. The ratio of free amino acid to antibody molar ratio can be at least 250:1.

The formulation can also contain a surfactant. The surfactant can be polysorbate 20, polysorbate 80, a poloxamer, or any combination thereof.

In some aspects, the formulation can minimize immunogenicity of the anti-α4β7 antibody.

The formulation, e.g., in the dried state, can be stable for at least three months at 40° C., 75% relative humidity (RH).

In another aspect, the formulation is lyophilized and comprises at least about 5% to about 10% anti-α4β7 antibody before lyophilization. The formulation can contain at least about 6% anti-α4β7 antibody before lyophilization. The formulation can be reconstituted from a lyophilized formulation (e.g., reconstituted to comprise a stable liquid formulation).

In another aspect, the invention relates to a stable formulation comprising a mixture of a non-reducing sugar, an anti-α4β7 antibody and at least one free amino acid, and the molar ratio of non-reducing sugar to anti-α4β7 antibody (mole:mole) is greater than 600:1 and the ratio of free amino acid to anti-α4β7 antibody (mole:mole) is greater than 250:1.

In another aspect, the invention relates to a stable liquid formulation comprising in aqueous solution with a non-reducing sugar, an anti-α4β7 antibody and at least one free amino acid, wherein the molar ratio of non-reducing sugar to anti-α4β7 antibody (mole:mole) is greater than 600:1. In yet a further aspect, the invention concerns a liquid formulation comprising at least about 40 mg/ml to about 80 mg/ml anti-α4β7 antibody, at least about 50-175 mM of one or more amino acids, and at least about 6% to at least about 10% (w/v) sugar. The liquid formulation may also contain a buffering agent. In some embodiments the liquid formulation also comprises a metal chelator. In some embodiments, the liquid formulation also comprises an anti-oxidant.

In another aspect, the invention relates to a liquid formulation comprising at least about 60 mg/ml anti-α4β7 antibody, at least about 10% (w/v) non-reducing sugar, and at least about 125 mM of one or more free amino acids.

In another aspect, the invention relates to a liquid formulation comprising at least about 60 mg/ml anti-α4β7 antibody, at least about 10% (w/v) non-reducing sugar, and at least about 175 mM of one or more free amino acids In still yet a further aspect, the invention also relates to a dry, e.g., lyophilized formulation comprising a mixture of a non-reducing sugar, an anti-α4β7 antibody, histidine, arginine, and polysorbate 80, wherein the formulation is in solid form, and the molar ratio of non-reducing sugar to anti-α4β7 antibody (mole:mole) is greater than 600:1.

In still yet a further aspect, the invention relates to a lyophilized formulation comprising a mixture of a non-reducing sugar, an anti-α4β7 antibody, histidine, arginine, and polysorbate 80. In this aspect, the molar ratio of non-reducing sugar to anti-α4β7 antibody (mole:mole) is greater than 600:1. Furthermore, the molar ratio of arginine to anti-α4β7 antibody (mole:mole) in the formulation is greater than 250:1.

In another aspect, the invention relates to a method of making a formulation described herein, comprising maintaining the product temperature below the collapse temperature during primary drying. The method can also contain an annealing step.

In one aspect, the invention relates to a method for treating a human patient suffering from inflammatory bowel disease, wherein the method comprises the step of administering to a patient suffering from inflammatory bowel disease, a humanized immunoglobulin or antigen-binding fragment thereof having binding specificity for human α4β7 integrin, wherein the humanized immunoglobulin or antigen-binding fragment comprises an antigen-binding region of nonhuman origin and at least a portion of an antibody of human origin, wherein the humanized immunoglobulin or antigen-binding fragment thereof is administered to the patient according to the following dosing regimen: (a) an initial dose of 300 mg of the humanized immunoglobulin or antigen-binding fragment thereof as an intravenous infusion; (b) followed by a second subsequent dose of 300 mg of the humanized immunoglobulin or antigen-binding fragment thereof as an intravenous infusion at about two weeks after the initial dose; (c) followed by a third subsequent dose of 300 mg of the humanized immunoglobulin or antigen-binding fragment thereof as an intravenous infusion at about six weeks after the initial dose; (d) followed by a fourth and subsequent doses of 300 mg of the humanized immunoglobulin or antigen-binding fragment thereof as an intravenous infusion every four weeks or every eight weeks after the third subsequent dose of the humanized antibody as needed; wherein the dosing regimen induces a clinical response and/or clinical remission in the inflammatory bowel disease of the patient; and further wherein the humanized immunoglobulin or antigen-binding fragment has binding specificity for the α4β7 complex, wherein the antigen-binding region comprises three complementarity determining regions (CDR1, CDR2, and CDR3) of a light chain variable region and three complementarity determining regions (CRD1, CDR2, and CDR3) of a heavy chain variable region of the amino acid sequence set forth below: light chain: CDR1 SEQ ID NO:11, CDR2 SEQ ID NO:12, CDR3 SEQ ID NO:13; heavy chain: CDR1 SEQ ID NO:8, CDR2 SEQ ID NO:9, CDR3 SEQ ID NO:10.

In another aspect, the invention relates to a dosing regimen for the therapeutic treatment of inflammatory bowel disease, wherein the dosing regimen comprises the step of: administering to a patient suffering from inflammatory bowel disease, a humanized immunoglobulin or antigen-binding fragment thereof having binding specificity for human α4β7 integrin, wherein the humanized immunoglobulin or antigen-binding fragment comprises an antigen-binding region of nonhuman origin and at least a portion of an antibody of human origin, wherein the humanized immunoglobulin or antigen-binding fragment thereof is administered to the patient according to the following dosing regimen: (a) an initial dose of 300 mg of the humanized immunoglobulin or antigen-binding fragment thereof as an intravenous infusion; (b) followed by a second subsequent dose of 300 mg of the humanized immunoglobulin or antigen-binding fragment thereof as an intravenous infusion at about two weeks after the initial dose; (c) followed by a third subsequent dose of 300 mg of the humanized immunoglobulin or antigen-binding fragment thereof as an intravenous infusion at about six weeks after the initial dose; (d) followed by a fourth and subsequent doses of 300 mg of the humanized immunoglobulin or antigen-binding fragment thereof as an intravenous infusion every four weeks or every eight weeks after the third subsequent dose of the humanized antibody as needed; wherein the dosing regimen induces a clinical response and/or clinical remission in the inflammatory bowel disease of the patient; and further wherein the humanized immunoglobulin or antigen-binding fragment has binding specificity for the α4β7 complex, wherein the antigen-binding region comprises three complementarity determining regions (CDR1, CDR2, and CDR3) of a light chain variable region and three complementarity determining regions (CRD1, CDR2, and CDR3) of a heavy chain variable region of the amino acid sequence set forth below: light chain: CDR1 SEQ ID NO:11, CDR2 SEQ ID NO:12, CDR3 SEQ ID NO:13; heavy chain: CDR1 SEQ ID NO:8, CDR2 SEQ ID NO:9, CDR3 SEQ ID NO:10.

In some aspects the method of treatment with the anti-α4β7 antibody formulation, the dose, or the dose regimen can minimize immunogenicity of the anti-α4β7 antibody.

The patient may have had a lack of an adequate response with, loss response to, or was intolerant to treatment with at least one of an immunomodulator, a tumor necrosis factor-alpha (TNF-α) antagonist or combinations thereof.

The inflammatory bowel disease can be Crohn's disease or ulcerative colitis. The inflammatory bowel disease can be moderate to severely active ulcerative colitis.

The dosing regimen can result in mucosal healing in patients suffering from moderate to severely active ulcerative colitis.

The patient may have previously received treatment with at least one corticosteroid for the inflammatory bowel disease. The dosing regimen can result in a reduction, elimination or reduction and elimination of corticosteroid use by the patient.

In some aspects, the humanized immunoglobulin or antigen-binding fragment thereof is administered in a final dosage form at a concentration of between about 1.0 mg/ml to about 1.4 mg/ml. The humanized immunoglobulin or antigen-binding fragment thereof can be administered in a final dosage form of about 1.2 mg/ml. The humanized immunoglobulin or antigen-binding fragment can be administered to the patient in about 30 minutes.

The humanized immunoglobulin or antigen-binding fragment thereof can be reconstituted from a lyophilized formulation.

The humanized immunoglobulin or antigen-binding fragment thereof can be reconstituted to comprise a stable liquid formulation.

In some aspects, the dosing regimen does not alter the ratio of CD4 to CD8 in cerebrospinal fluid of patients receiving said treatment.

The patient can be a person 65 years of age or older and does not require any adjustment of the dosing regimen.

BRIEF DESCRIPTION OF THE DRAWINGS

FIGS. 1A and 1B are illustrations of a nucleotide sequence (SEQ ID NO:1) encoding the heavy chain of a humanized anti-α4β7 immunoglobulin, and the deduced amino acid sequence of the heavy chain (SEQ ID NO:2). The nucleotide sequence contains cloning sites (lower case), Kozak sequence (upper case, nucleotides 18-23 of SEQ ID NO:1) and leader sequence (lower case, nucleotides 24-86 of SEQ ID NO:1) at the 5' end of the heavy chain. The open reading frame of the nucleotide sequence is nucleotides 24-1433 of SEQ ID NO:1.

FIG. 2 is an illustration of a nucleotide sequence (SEQ ID NO:3) encoding the light chain of a humanized immunoglobulin referred to herein as vedolizumab, and the deduced amino acid sequence (SEQ ID NO: 4) of the light chain. The nucleotide sequence contains cloning sites (lower case), Kozak sequence (upper case, nucleotides 18-23 of SEQ TD NO:3) and leader sequence (lower case, nucleotides 24-80 of SEQ ID NO:3) at the 5' end of the heavy chain. The open reading frame of the nucleotide sequence is nucleotides 24-737 of SEQ ID NO:3.

FIG. 3 is an alignment of the amino acid sequences of (A) the mature humanized light chain (amino acids 20-238 of SEQ ID NO:4) of the humanized immunoglobulin referred to herein as vedolizumab and (B) the mature humanized light chain of the humanized immunoglobulin referred to herein as LDP-02 (SEQ ID NO:5). (Regarding LDP-02, see, WO 98/06248 and Feagan et al., *N. Eng. J. Med.* 352:2499-2507 (2005). Feagan et al. describe a clinical study of LDP-02, but in the article they refer to LDP-02 as MLNO2.) The alignment illustrates that the amino acid sequences of the light chains of vedolizumab and LDP-02 differ at positions 114 and 115 of the mature light chains.

FIG. 4 is an alignment of amino acid sequences of (A) a generic human kappa light chain constant region (SEQ ID NO:6) and (B) a generic murine kappa light chain constant region (SEQ ID NO:7). The amino acid residues Thr and Val (which are present at positions 114 and 115 of the mature vedolizumab light chain (amino acids 133 and 134 of SEQ ID NO:4)) are present in the constant region of the human kappa light chain, whereas the amino acid residues Ala and Asp (which arc present at positions 114 and 115 of the mature LDP-02 light chain (SEQ ID NO:5)) are present in the constant region of the mouse kappa light chain.

FIG. 7 shows the amino acid sequences of (A) the mature human GM607'TCL antibody kappa light chain variable region and (B) the human 21/28'CL heavy chain variable region.

DETAILED DESCRIPTION OF THE INVENTION

Figure 5:
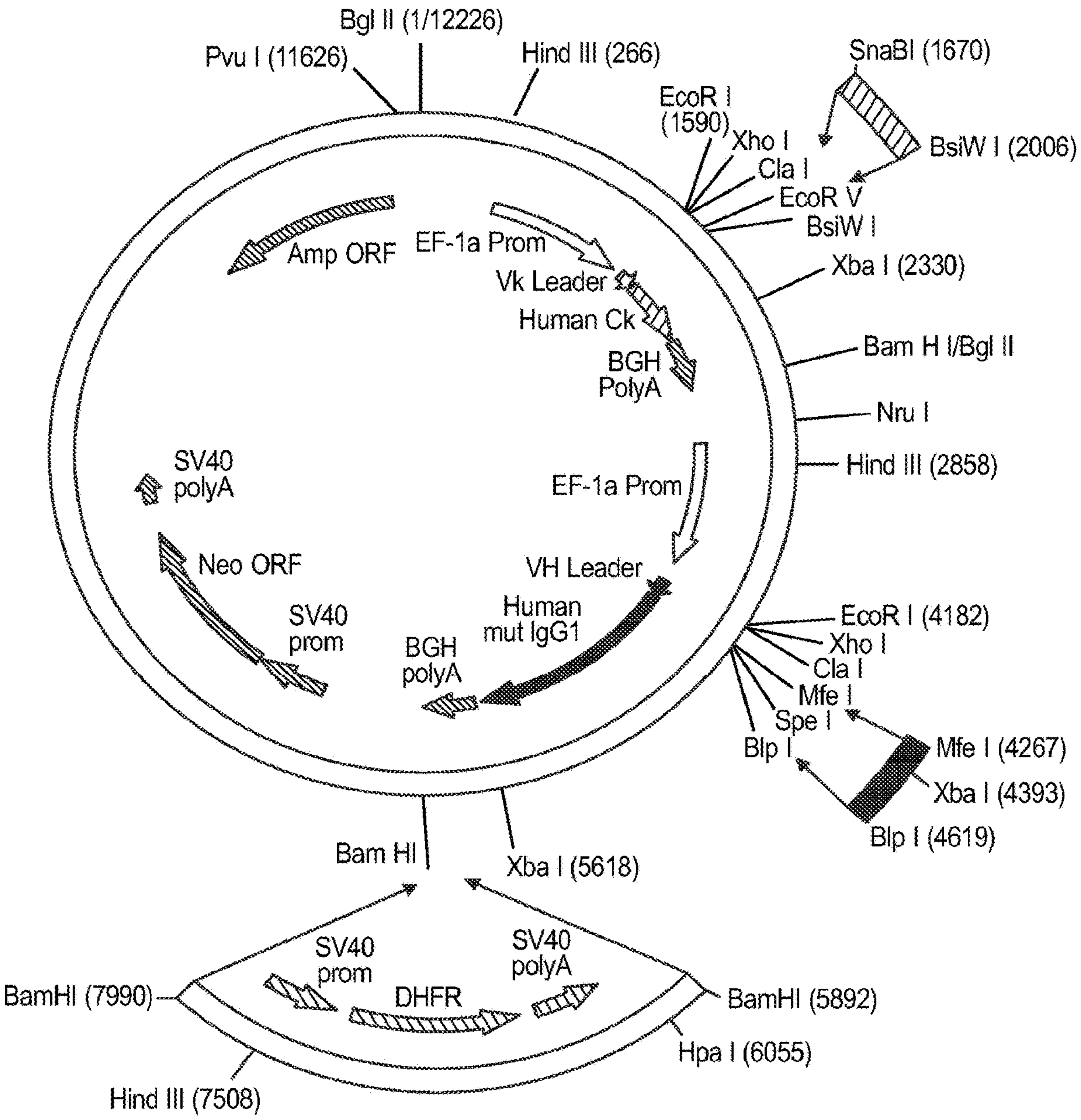
FIG. 5 is a map of vector pLKTOK38D (also referred to as pTOK38MLN02-TV), which encodes the humanized heavy chain and the humanized light chain of MLNO2, and is suitable for producing vedolizumab in CHO cells. (See, U.S. Patent Application Publication No. 2004/0033561 A1 which discloses pLKTOK38. pLKTOK38D is a variant of pLKTOK38 in which the restriction sites indicated on the map flank the sequence encoding the light chain variable region.)

The invention relates to formulations comprising anti-α4β7 antibodies. The formulations may be mixtures comprising non-reducing sugar, anti-α4β7 antibody and one or more free amino acids, and the molar ratio of the non-reducing sugar to anti-α4β7 antibody is greater than 600 mole non-reducing sugar:1 mole anti-α4β7 antibody. The formulations may be in a solid or liquid form.

Definitions

The term "pharmaceutical formulation" refers to a preparation that contains an anti-α4β7 antibody in such form as to permit the biological activity of the antibody to be effective, and which contains no additional components which are unacceptably toxic to a subject to which the formulation would be administered.

A "stable" formulation is one in which the antibody therein substantially retains its physical stability and/or chemical stability and/or its biological activity upon storage. In one aspect, the formulation substantially retains its physical and chemical stability, as well as its biological activity upon storage. The storage period is generally selected based on the intended shelf-life of the formulation. Various analytical techniques for measuring protein stability are available in the art and are reviewed in *Peptide and Protein Drug Delivery,* 247-301, Vincent Lee Ed., Marcel Dekker, Inc., New York, N.Y., Pubs. (1991) and Jones, A. *Adv. Drug Delivery Rev.* 10: 29-90 (1993), for example.

A "deamidated" monoclonal antibody is one in which one or more asparagine or glutamine residue thereof has been derivatized, e.g. to an aspartic acid or an iso-aspartic acid.

An antibody which is "susceptible to deamidation" is one comprising one or more residue which has been found to be prone to deamidate.

An antibody which is "susceptible to oxidation" is an antibody comprising one or more residue which has been found to be prone to oxidation.

An antibody which is "susceptible to aggregation" is one which has been found to aggregate with other antibody molecule(s), especially upon freezing, heating, drying, reconstituting and/or agitation.

An antibody which is "susceptible to fragmentation" is one which has been found to be cleaved into two or more fragments, for example at a hinge region thereof.

By "reducing deamidation, oxidation, aggregation, or fragmentation" is intended to mean preventing or decreasing (e.g., to 80%, 60%, 50%, 40%, 30%, 20% or 10% of) the amount of deamidation, aggregation, or fragmentation relative to the monoclonal antibody formulated at a different pH or in a different buffer.

An "aggregate", "SEC aggregate", or "soluble aggregate" is more than one and less than or equal to ten antibody proteins and/or fragments associated together through either covalent, ionic, or hydrophobic interactions to form a larger protein body.

An "insoluble aggregate" or "particle" is greater than ten antibody proteins and/or fragments associated together through either covalent, ionic, or hydrophobic interactions to form a larger protein body.

As used herein, "biological activity" of a monoclonal antibody refers to the ability of the antibody to bind to antigen and result in a measurable biological response which can be measured in vitro or in vivo. Such activity may be antagonistic or agonistic.

The cell surface molecule, "α4β7 integrin," or "α4β7," is a heterodimer of an $\alpha_4$ chain (CD49D, ITGA4) and a $\beta_7$ chain (ITGB7). Each chain can form a heterodimer with an alternative integrin chain, to form $\alpha_4\beta_1$ or $\alpha_E\beta_7$. Human $\alpha_4$ and $\beta_7$ genes (GenBank (National Center for Biotechnology Information, Bethesda, MD) RefSeq Accession numbers NM_000885 and NM_000889, respectively) are expressed by B and T lymphocytes, particularly memory CD4+ lymphocytes. Typical of many integrins, α4β7 can exist in either a resting or activated state. Ligands for α4β7 include vascular cell adhesion molecule (VCAM), fibronectin and mucosal addressin (MAdCAM (e.g., MAdCAM-1)).

As used herein, a human immunoglobulin or antigen-binding fragment thereof that has "binding specificity for the α4β7 complex" binds to α4β7, but not to α4β1 or αEB7.

As used herein, an "isotonic" formulation has substantially the same osmotic pressure as human blood. Isotonic formulations will generally have an osmotic pressure from about 250 to 350 mOsm. Isotonicity can be measured using a vapor pressure or ice-freezing type osmometer, for example.

As used herein, "buffering agent" refers to a buffer that resists changes in pH by the action of its acid-base conjugate components. The buffering agent may be present in a liquid or solid formulation of the invention. The buffering agent adjusts the pH of the formulation to about 5.0 to about 7.5, to about 5.5 to about 7.5, to about 6.0 to about 6.5, or to a pH of about 6.3. In one aspect, examples of buffering agents that will control the pH in the 5.0 to 7.5 range include acetate, succinate, gluconate, histidine, citrate, phosphate, maleate, cacodylate, 2-[N-morpholino]ethanesulfonic acid (MES), bis(2-hydroxyethyl)iminotris[hydroxymethyl]methane (Bis-Tris), N-[2-acetamido]-2-iminodiacetic acid (ADA), glycylglycine and other organic acid buffers. In another aspect, the buffering agent herein is histidine or citrate.

A "histidine buffer" is a buffer comprising histidine ions. Examples of histidine buffers include histidine chloride, histidine acetate, histidine phosphate, histidine sulfate solutions. The histidine buffer or histidine-HCl buffer has a pH between about pH 5.5 to 6.5, about pH 6.1 to 6.5, or about pH 6.3.

A "saccharide" herein is a compound that has a general formula $(CH_2O)_n$ and derivatives thereof, including monosaccharides, disaccharides, trisaccharides, polysaccharides, sugar alcohols, reducing sugars, nonreducing sugars, and the like. In one aspect, examples of saccharides herein include glucose, sucrose, trehalose, lactose, tructose, maltose, dextran, erythritol, glycerol, arabitol, sylitol, sorbitol, mannitol, mellibiose, melezitose, raffinose, mannotriose, stachyose, maltose, lactulose, maltulose, glucitol, maltitol, lactitol, isomaltulose, and the like. A saccharide can be a lyoprotectant. In another aspect, the saccharide herein is a nonreducing disaccharide, such as sucrose.

A "surfactant" herein refers to an agent that lowers surface tension of a liquid. The surfactant can be a nonionic surfactant. In one aspect, examples of surfactants herein include polysorbate (polyoxyethylene sorbitan monolaurate, for example, polysorbate 20 and, polysorbate 80); TRITON (t-Octylphenoxypolyethoxyethanol, nonionic detergent, Union Carbide subsidiary of Dow Chemical Co., Midland MI); sodium dodecyl sulfate (SOS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroarnidopropyl-, cocamidopropyl-, linoleamidopropyl-, myristarnidopropyl-, palmidopropyl-, or isostearamidopropyl-betaine (e.g. lauroarnidopropyl); myristamidopropyl-, palmidopropyl-, or isostearamidopropyl-dimethylarnine; sodium methyl cocoyl-, or disodium methyl oleyl-taurate; sorbitan monopalmitate; and the MONAQUAT series (Mona Industries, Inc., Paterson, N.J.); polyethyl glycol (PEG), polypropylene glycol (PPG), and copolymers ofpoloxyethylene and poloxypropylene glycol (e.g. Pluronics/Poloxamer, PF68 etc); etc. In another aspect, the surfactant is polysorbate 80.

The term "antibody" herein is used in the broadest sense and specifically covers full length monoclonal antibodies, immunoglobulins, polyclonal antibodies, multispecific antibodies (e.g. bispecific antibodies) formed from at least two full length antibodies, e.g., each to a different antigen or epitope, and individual antigen binding fragments, including dAbs, scFv, Fab, $F(ab)'_2$, Fab', including human, humanized and antibodies from non-human species and recombinant antigen binding forms such as monobodies and diabodies.

Molar amounts and ratios of anti-α4β7 antibody to other excipients described herein are calculated on the assumption of an approximate molecular weight of about 150,000 daltons for the antibody. The actual antibody molecular weight may differ from 150,000 daltons, depending on amino acid composition or post-translational modification, e.g., as dependent on the cell line used to express the antibody. Actual antibody molecular weight can be +/−5% of 150,000 daltons.

The term "human antibody" includes an antibody that possesses a sequence that is derived from a human germ-line immunoglobulin sequence, such as an antibody derived from transgenic mice having human immunoglobulin genes (e.g., XENOMOUSE genetically engineered mice (Abgenix, Fremont, CA), HUMAB-MOUSE®, KIRIN TC MOUSE™ transchromosome mice, KMMOUSE® (MEDAREX, Princeton, NJ)), human phage display libraries, human myeloma cells, or human B cells.

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature,* 352:624-628 (1991) and Marks et al., *J Mol. Biol.,* 222:581-597 (1991), for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA,* 81:6851-6855 (1984)). Chimeric antibodies of interest herein include "primatized" antibodies comprising variable domain antigen binding sequences derived from a non-human primate (e.g. Old World Monkey, Ape etc) and human constant region sequences.

"Antigen binding fragments" of the humanized immunoglobulin prepared in the formulation of the invention comprise at least the variable regions of the heavy and/or light chains of an anti-α4β7 antibody. For example, an antigen binding fragment of vedolizumab comprises amino acid residues 20-131 of the humanized light chain sequence of SEQ ID NO:4. Examples of such antigen binding fragments include Fab fragments, Fab' fragments, scFv and F(ab')2 fragments of a humanized immunoglobulin known in the art. Antigen binding fragments of the humanized immunoglobulin of the invention can be produced by enzymatic cleavage or by recombinant techniques. For instance, papain or pepsin cleavage can be used to generate Fab or F(ab')2 fragments, respectively. Antibodies can also be produced in a variety of truncated forms using antibody genes in which one or more stop codons have been introduced upstream of the natural stop site. For example, a recombinant construct encoding the heavy chain of an F(ab')2 fragment can be designed to include DNA sequences encoding the $CH_1$ domain and hinge region of the heavy chain. In one aspect, antigen binding fragments inhibit binding of α4β7 integrin to one or more of its ligands (e.g. the mucosal addressin MAdCAM (e.g., MAdCAM-1), fibronectin).

Papain digestion of antibodies produces two identical antigen binding fragments, called "Fab" fragments, each with a single antigen binding site, and a residual "Fc" fragment, whose name reflects its ability to crystallize readily. Pepsin treatment yields an F(ab')2 fragment that has two antigen binding sites and is still capable of cross-linking antigen.

"Fv" is an antibody fragment which consists of a dimer of one heavy chain variable domain and one light chain variable domain in non-covalent association.

The Fab fragment also contains the constant domain of the light chain and the first constant domain (CHI) of the heavy chain. Fab' fragments differ from Fab fragments by the addition of a few residues at the carboxy terminus of the heavy chain CHI domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. In one aspect, the Fv polypeptide further comprises a polypeptide linker between the $V_H$ and $V_L$ domains which enables the scFv to form the desired structure for antigen binding. For a review of scFv see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen binding sites, which fragments comprise a variable heavy domain ($V_H$) connected to a variable light domain ($V_L$) in the same polypeptide chain ($VHV_L$). By using a linker that is too short to allow pairing between the two domains on the same chain, the domains are forced to pair with the complementary domains of another chain and create two antigen binding sites. Diabodies are described more fully in, for example, EP 404,097; WO 93/11161; and Hollinger et al., *Proc. Natl. Acad. Sci USA,* 90:6444-6448 (1993).

A "full length antibody" is one which comprises an antigen binding variable region as well as a light chain constant domain ($C_L$) and heavy chain constant domains, $C_{H1}$, $C_{H2}$ and CH3. The constant domains may be native sequence constant domains (e.g. human native sequence constant domains) or amino acid sequence variants thereof. In one aspect, the full length antibody has one or more effector functions.

An "amino acid sequence variant" antibody herein is an antibody with an amino acid sequence which differs from a main species antibody. Ordinarily, amino acid sequence variants will possess at least about 70%, at least about 80%, at least about 85%, at least about 90%, or at least about 95% homology with the main species antibody. The amino acid sequence variants possess substitutions, deletions, and/or additions at certain positions within or adjacent to the amino acid sequence of the main species antibody, but retain antigen binding activity. Variations in sequence of the constant regions of the antibody will have less effect on the antigen binding activity than variations in the variable regions. In the variable regions, amino acid sequence variants will be at least about 90% homologous, at least about 95% homologous, at least about 97% homologous, at least about 98% homologous, or at least about 99% homologous with the main species antibody.

"Homology" is defined as the percentage of residues in the amino acid sequence variant that are identical after aligning the sequences and introducing gaps, if necessary, to achieve the maximum percent homology. Methods and computer programs for the alignment are well known in the art.

A "therapeutic monoclonal antibody" is an antibody used for therapy of a human subject. Therapeutic monoclonal antibodies disclosed herein include anti-α4β7 antibodies.

A "glycosylation variant" antibody herein is an antibody with one or more carbohydrate moieties attached thereto which differ from one or more carbohydrate moieties attached to a main species antibody. Examples of glycosylation variants herein include antibody with a G1 or G2 oligosaccharide structure, instead of a G0 oligosaccharide structure, attached to an Fc region thereof, antibody with one or two carbohydrate moieties attached to one or two light chains thereof, antibody with no carbohydrate attached to one or two heavy chains of the antibody, etc, and combinations of glycosylation alterations.

Antibody "effector functions" refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), and the like.

Depending on the amino acid sequence of the constant domain of their heavy chains, full length antibodies can be assigned to different "classes". There are five major classes of full length antibodies: IgA, IgD, IgE, IgG, and IgM, and several of these may be further divided into "subclasses" (isotypes), e.g., IgG1, IgG2, IgG3, IgG4, IgA, and TgA2. The heavy-chain constant domains that correspond to the different classes of antibodies are called a, 6, c, 7, and, respectively. The subunit structures and three-dimensional configurations of different classes of immunoglobulins are well known.

The "light chains" of antibodies from any vertebrate species can be assigned to one of two clearly distinct types, called kappa (κ) and lambda (λ), based on the amino acid sequences of their constant domains.

"Antibody-dependent cell-mediated cytotoxicity" and "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or U.S. Pat. No. 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *PNAS* (*USA*) 95:652-656 (1998).

The terms "Fc receptor" or "FcR" are used to describe a receptor that binds to the Fc region of an antibody. In one aspect, the FcR is a native sequence human FcR. In another aspect, the FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (See review in M. Daeron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J Lab. Clin. Med.* 126:33-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J Immunol.* 117:587 (1976) and Kim et al., *J Immunol.* 24:249 (1994)).

The term "hypervariable region" when used herein refers to the amino acid residues of an antibody which are responsible for antigen binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mal. Biol.* 196:901-917 (1987)). "Framework Region" or "FR" residues are those variable domain residues other than the hypervariable region residues as herein defined. The hypervariable region or the CDRs thereof can be transferred from one antibody chain to another or to another protein to confer antigen binding specificity to the resulting (composite) antibody or binding protein.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

An "affinity matured" antibody is one with one or more alterations in one or more hypervariable regions thereof which result an improvement in the affinity of the antibody for antigen, compared to a parent antibody which does not possess those alteration(s). In one aspect, affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. Proc Nat. Acad. Sci, USA 91:3809-3813 (1994); Schier et al. *Gene* 169:147-155 (1995); Yelton et al. *J Immunol.* 155:1994-2004 (1995); Jackson et al., *J Immunol.* 154(7): 3310-9 (1995); and Hawkins et al., *J Mol. Biol.* 226:889-896 (1992).

An "isolated" antibody is one which has been identified and separated and/or recovered from a component of its natural environment. In certain embodiments, the antibody will be purified (1) to greater than 95% by weight of protein as determined by the Lowry method, and alternatively, more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coornassie blue or silver stain. Isolated antibody includes the antibody in situ within recombinant cells since at least one component of the antibody's natural environment will not be present. Ordinarily, however, isolated antibody will be prepared by at least one purification step.

"Treatment" refers to both therapeutic treatment and prophylactic or preventative measures. Those in need of treatment include those already with the disease as well as those in which the disease or its recurrence is to be prevented. Hence, the patient to be treated herein may have been diagnosed as having the disease or may be predisposed or susceptible to the disease. The terms "patient" and "subject" are used interchangeably herein.

The antibody which is formulated is substantially pure and desirably substantially homogeneous (i.e. free from contaminating proteins etc). "Substantially pure" antibody means a composition comprising at least about 90% antibody by weight, based on total weight of the protein in the composition, at least about 95% or 97% by weight. "Substantially homogeneous" antibody means a composition comprising protein wherein at least about 99% by weight of protein is specific antibody, e.g., anti-$\alpha4\beta7$ antibody, based on total weight of the protein.

"Clinical remission" as used herein with reference to ulcerative colitis subjects refers to a complete Mayo score of 2 or less points and no individual subscore greater than 1 point. Crohn's disease "clinical remission" refers to a CDAI score of 150 points or less.

A "clinical response" as used herein with reference to ulcerative colitis subjects refers to a reduction in complete Mayo score of 3 or greater points and 30% from baseline, (or a partial Mayo score of 2 or greater points and 25% or greater from baseline, if the complete Mayo score was not performed at the visit) with an accompanying decrease in rectal bleeding subscore of 1 or greater points or absolute rectal bleeding score of 1 or less point. A "clinical response" as used herein with reference to Crohn's disease subjects refers to a 70 point or greater decrease in CDAI score from baseline (week 0).

"Mucosal healing" as used herein with reference to ulcerative colitis subjects refers to an endoscopic subscore of 1 point or less.

As used herein, "treatment failure" refers to disease worsening, a need for rescue medications or surgical intervention for treatment of ulcerative colitis or Crohn's disease. A rescue medication is any new medication or any increase in dose of a baseline medication required to treat new or unresolved ulcerative colitis or Crohn's disease symptoms (other than antidiarrheals for control of chronic diarrhea).

Formulations

As described herein, it has been discovered that anti-$\alpha4\beta7$ antibodies are highly stable when in a dry, e.g., lyophilized formulation with excess (on a mole basis) non-reducing sugar. In particular, lyophilized formulations in which the ratio of non-reducing sugar to anti-$\alpha4\beta7$ antibody (mole:mole) is greater than 600:1 are shown herein to be stable for at least 2 years.

The present invention provides, in a first aspect, a stable anti-$\alpha4\beta7$ antibody formulation. In one aspect, the formulation comprises a buffer, at least one stabilizer and an anti-$\alpha4\beta7$ antibody. In one aspect, a dry formulation comprises one or more non-reducing sugars and an anti-$\alpha4\beta7$ antibody, wherein the ratio of non-reducing sugar to anti-$\alpha4\beta7$ antibody (mole:mole) is greater than 600:1. The formulation also comprises one or more free amino acids. One or more of the amino acids also can act as a buffer. In one aspect, one or more of the amino acids can act as a stabilizer. The formulation may optionally further comprise at least one surfactant. In one embodiment, the formulation is dry, e.g., lyophilized. The antibody in the formulation may be a full length antibody or an antigen binding fragment thereof, such as a Fab, Fv, scFv, Fab' or F(ab')2 fragment.

The formulation can contain any desired non-reducing sugars. In one aspect, non-reducing sugars that can be included in the formulation include, for example, mannitol, sorbital, sucrose, trehalose, raffinose, stachyose, melezitose, dextran, maltitol, lactitol, isomaltulose, palatinit and combinations thereof. In another aspect, non-reducing sugars are sucrose, trehalose, mannitol, and sorbitol. The absolute amount of non-reducing sugar in the formulation is not critical, but the ratio of non-reducing sugar to anti-$\alpha4\beta7$ antibody (mole:mole) is greater than 400:1 In another aspect, the ratio of non-reducing sugar to anti-α4β7 antibody (mole:mole) is at least about 600:1; at least about 625:1; at least about 650:1; at least about 675:1, at least about 700:1; at least about 750:1, at least about 800:1, at least about 1000:1, at least about 1200:1, at least about 1400:1, at least about 1500:1, at least about 1600:1, at least about 1700:1, at least about 1800:1, at least about 1900:1, or at least about 2000:1. Generally, it is desirable that the non-reducing sugar is present in an amount which reduces soluble aggregate formation in a liquid formulation, such as aggregate formation which occurs upon freezing and thawing and/or drying and reconstituting. A ratio of non-reducing sugar to anti-α4β7 antibody (mole:mole) higher than about 730:1 may give slightly reduced soluble aggregate formation in the lyophilized state. The sugar:protein weight ratio can be greater than 1.5:1 (w/w). In another aspect, the non-reducing sugar concentrations for liquid (e.g., pre-drying or post-reconstitution) formulations are in the range from about 10 mM to about 1 M, for example, from about 60 mM to about 600 mM, about 100 mM to about 450 mM, about 200 mM to about 350 mM, about 250 mM to about 325 mM, and about 275 mM to about 300 mM. In another aspect, the amounts of non-reducing sugar in a dry, (e.g., lyophilized) formulation are in the range from about 40% to about 70% (w/w of dry formulation). In another aspect, the amounts of non-reducing sugar in a dry (e.g., lyophilized) formulation are in the range from about 40% to about 60%, from about 45% to about 55% or about 51% (w/w). In other aspects, the amount of non-reducing sugar in a dry, (e.g., lyophilized) formulation is greater than about 51% (w/w of dry formulation) when the protein amount is about 31% (w/w of dry formulation) or greater than about a 1.6:1 mass ratio of non-reducing sugar to protein in the dry formulation. In yet still another aspect, sucrose is the non-reducing sugar for use in the formulation.

The formulation can contain any desired free amino acid, which can be in the L-form, the D-form or any desired mixture of these forms. In one aspect, free amino acids that can be included in the formulation include, for example, histidine, alanine, arginine, glycine, glutamic acid, serine, lysine, tryptophan, valine, cysteine and combinations thereof. Some amino acids can stabilize the proteins against degradation during manufacturing, drying, lyophilization and/or storage, e.g., through hydrogen bonds, salt bridges antioxidant properties or hydrophobic interactions or by exclusion from the protein surface. Amino acids can act as tonicity modifiers or can act to decrease viscosity of the formulation. In another aspect, free amino acids, such as histidine and arginine, can act as cryoprotectants and lyoprotectants, and do not crystallize when lyophilized as components of the formulation. Free amino acids, such as glutamic acid and histidine, alone or in combination, can act as buffering agents in aqueous solution in the pH range of 5 to 7.5. In still yet another aspect, the formulation contains histidine, or histidine and arginine. In still yet a further aspect, the free amino acid concentrations for liquid formulations are in the range from about 10 mM to about 0.5 M, for example, from about 15 mM to about 300 mM, about 20 mM to about 200 mM, or about 25 mM to about 150 mM, about 50 mM or about 125 mM. In still yet a further aspect, the amounts of histidine in a dry, (e.g., lyophilized) formulation are in the range from about 1% to about 10% (w/w of dry formulation), or from about 3% to about 6% (w/w). In some embodiments, the amount of histidine in a dry, (e.g., lyophilized) formulation is greater than about 4% (w/w of the dry formulation) when the protein amount is about 31% (w/w of the dry formulation) or greater than about a 0.15:1 mass ratio of histidine to protein in the dry formulation. In still yet another aspect, the amounts of arginine in a dry, (e.g., lyophilized) formulation are in the range from about 4% to about 20% (w/w of dry formulation), or from about 10% to about 15% (w/w). In some embodiments, the amount of arginine in a dry, (e.g., lyophilized) formulation is greater than about 13% (w/w of the dry formulation) when the protein amount is about 31% (w/w of the dry formulation) or greater than about a 0.4:1 mass ratio of arginine to protein in the dry formulation. In embodiments of combinations of amino acids, such as histidine and arginine, the molar ratio of total amino acid to antibody ratio can be at least 200:1, about 200:1 to about 500:1, or at least 400:1.

The formulation can optionally further contain at least one surfactant. In one aspect, surfactants that can be included in the formulation include, for example, polysorbate 20, polysorbate 80, a poloxamer (Pluronic®) and combinations thereof. When present, the surfactant is generally included in an amount which reduces formation of insoluble aggregates of antibody, e.g., during bottling, freezing, drying, lyophilization and/or reconstitution. The surfactant concentration, e.g., in a pre-dry, (e.g., lyophilized) or post-reconstitution formulation, is generally from about 0.0001% to about 1.0%, from about 0.01% to about 0.1%, for example about 0.02%, 0.03%, 0.04%, 0.05%, 0.06%, 0.07%, 0.08%, or 0.09% (w/v), 0.05% to 0.07% or 0.06% (w/v). The surfactant amount, e.g., in a dry, (e.g., lyophilized) formulation, is generally from about 0.01% to about 3.0% (w/w), from about 0.10% to about 1.0%, for example about 0.15%, 0.20%, 0.25%, 0.30%, 0.35%, 0.40%, or 0.50% (w/w). In another aspect, the surfactant: antibody molar ratio is about 1:1. The anti-α4β7 antibody can be present in any desired amount in the formulation, provided that the ratio of non-reducing sugar to anti-α4β7 antibody (mole:mole) is greater than about 600:1. However, the formulation can contain a high concentration of anti-α4β7 antibody. For example, liquid formulations can comprise at least about 10 mg/ml, at least about 20 mg/ml, at least about 30 mg/ml, at least about 40 mg/ml, at least about 50 mg/ml, at least about 60 ml/ml, at least about 70 mg/ml, at least about 80 mg/ml, at least about 90 mg/ml, at least about 100 mg/ml, from about 40 mg/ml to about 80 mg/ml anti-α4β7 antibody, about 60 mg/ml anti-α4β7 antibody. Dry formulations (e.g., lyophilized) can contain at least about 5%, at least about 10%, at least about 15%, at least about 20%, at least about 25%, at least about 30%, or about 31% or about 32% anti-α4β7 antibody by weight.

If desired, the formulation can further comprise a metal chelator and/or an anti-oxidant, as well as other pharmaceutically acceptable excipients. Suitable metal chelators include, for example, methylamine, ethylenediamine, desferoxamine, trientine, histidine, malate, phosphonate compounds, e.g., etidronic acid, ethylenediaminetetraacetic acid (EDTA), ethyleneglycoltetraacetic acid (EGTA), and the like. Suitable anti-oxidants include, for example, citric acid, uric acid, ascorbic acid, lipoic acid, glutathione, tocopherol, carotene, lycopene, cysteine and the like.

The formulation can be a liquid or a solid. Liquid formulations can be aqueous solutions or suspensions, prepared in a suitable aqueous solvent, such as water or an aqueous/organic mixture, such as water alcohol mixtures. Liquid formulations can have a pH between about 5.5 and about 7.5, between about 6.0 and about 7.0, or between about 6.0 and about 6.5, such as about 6.0, 6.1, 6.2, 6.3, 6.4 or 6.5. Liquid formulations can be refrigerated (e.g., 2-8° C.) or frozen (e.g., at −20° C. or −80° C.) for storage. Solid formulations can be prepared in any suitable way and can be in the form of a cake or powder, for example. The solid formulation is prepared by drying a liquid formulation as described herein, for example by lyophilization, spray drying, air drying in a film (e.g., for transdermal delivery), mixing into a lipid emulsion and drying as spheres for oral delivery or film for transdermal delivery. When the formulation is a solid formulation, the formulation can have a moisture content of no more than about 5%, no more than about 4.5%, no more than about 4%, no more than about 3.5%, no more than about 3%, no more than about 2.5%, no more than about 2%, no more than about 1.5%, no more than about 1%, or is substantially anhydrous. Solid formulations can be dissolved, i.e. reconstituted, in a suitable medium or solvent to become liquid suitable for administration. Suitable solvents for reconstituting the solid formulation include water, isotonic saline, buffer, e.g., phosphate-buffered saline, Ringer's (lactated or dextrose) solution, minimal essential medium, alcohol/aqueous solutions, dextrose solution, etc. The amount of solvent can result in a therapeutic protein concentration higher, the same, or lower than the concentration prior to drying. In one aspect, the reconstituted anti-α4β7 antibody concentration is the same concentration as in the pre-drying liquid formulation.

The formulation may be sterile, and this can be achieved according to the procedures known to the skilled person for generating sterile pharmaceutical formulations suitable for administration to human subjects, prior to, or following, preparation of the formulation. The formulation can be sterilized as a liquid, e.g., before drying and/or after reconstitution by filtration through small pores, through aseptic processing or by exposure to ultraviolet radiation. Filter pore sizes can be 0.1 μm or 0.2 μm to filter microorganisms or 10 to 20 nm to filter virus particles. Alternatively, or additionally, the dried formulation can be sterilized, e.g., by exposure to gamma radiation. In one aspect, the anti-α4β7 antibody liquid formulation is sterilized by filtration before drying.

In one aspect, the formulation is stable upon storage. In another aspect, the formulation is stable upon storage in the dry state. Stability can be tested by evaluating physical stability, chemical stability, and/or biological activity of the antibody in the formulation around the time of formulation as well as following storage at the noted temperatures. Physical and/or chemical stability of a liquid formulation or a reconstituted dry powder can be evaluated qualitatively and/or quantitatively in a variety of different ways (see, e.g., Analytical Techniques for Biopharmaceutical Development, Rodriguez-Diaz et al. eds. Informa Healthcare (2005)), including evaluation of aggregate formation (for example using size exclusion (or gel filtration) chromatography (SEC), matrix-assisted laser desorption-ionization time-of-flight mass spectrometry (MALDI-TOF MS), analytical ultracentrifugation, light scattering (photon correlation spectroscopy, dynamic light scattering (DLS), multi-angle laser light scattering (MALLS)), flow-based microscopic imaging, electronic impedance (coulter) counting, light obscuration or other liquid particle counting system, by measuring turbidity, by density gradient centrifugation and/or by visual inspection); by assessing charge heterogeneity using cation exchange chromatography (see also Vlasak and Ionescu, Curr. Pharm. Biotechnol. 9:468-481 (2008) and Harris et al. J Chromatogr. B Biomed. Sci. Appl. 752:233-245 (2001)), isoelectric focusing (IEF), e.g. capillary technique (cIEF), or capillary zone electrophoresis; amino-terminal or carboxy terminal sequence analysis; mass spectrometric analysis; SDS-PAGE or SEC analysis to compare fragmented, intact and multimeric (i.e., dimeric, trimeric, etc.) antibody; peptide map (for example tryptic or LYS—and the like); evaluating biological activity or antigen binding function of the antibody; and the like. Biological activity or antigen binding function, e.g., binding of the anti-α4β7 antibody to MAdCAM (e.g., MAdCAM-1) or inhibition of the binding of a cell expressing α4β7 integrin to MAdCAM (e.g., MAdCAM-1), e.g., immobilized MAdCAM (e.g., MAdCAM-1), can be evaluated using various techniques available to the skilled practitioner (see e.g., Soler et al., *J. Pharmacol. Exper. Ther.* 330:864-875 (2009)).

Stability of a solid-state formulation can also be evaluated qualitatively and/or quantitatively in a variety of different ways, including direct tests, such as identifying crystal structure by X-Ray Powder Diffraction (XRPD); evaluating antibody structure in the solid state using Fourier Transform Infrared Spectroscopy (FTIR); and measuring thermal transitions in the lyophilized solid (melting, glass transition, etc.) using Differential Scanning Calorimetry (DSC, e.g., to assess denaturation) and indirect tests such as measuring moisture content by Karl Fisher test, e.g., to extrapolate the likelihood of chemical instability through hydrolysis. Measurement of the moisture content of a dry formulation can indicate how likely a formulation will undergo chemical or physical degradation, with higher moisture leading to more degradation.

Stability can be measured at a selected temperature for a selected time period. In one aspect, a dry, (e.g., lyophilized) formulation is stable at about 40° C., 75% RH for at least about 2-4 weeks, at least about 2 months, at least about 3 months, at least about 6 months, at least about 9 months, at least about 12 months, or at least about 18 months. In another aspect, the formulation (liquid or dry (e.g., lyophilized)) is stable at about 5° C. and/or 25° C. and 60% RH for at least about 3 months, at least about 6 months, at least about 9 months, at least about 12 months, at least about 18 months, at least about 24 months, at least about 30 months, at least about 36 months, or at least about 48 months. In another aspect, the formulation (liquid or dry (e.g., lyophilized)) is stable at about −20° C. for at least about 3 months, at least about 6 months, at least about 9 months, at least about 12 months, at least about 18 months, at least about 24 months, at least about 30 months, at least about 36 months, at least about 42 months, or at least about 48 months. Furthermore, the liquid formulation may, in some embodiments, be stable following freezing (to, e.g., −80° C.) and thawing, such as, for example, following 1, 2 or 3 cycles of freezing and thawing.

Instability may involve any one or more of: aggregation (e.g., non-covalent soluble aggregation (caused by hydrophobic or charge interactions), covalent soluble aggregation (e.g., disulfide bond rearrangement/scrambling), insoluble aggregation (cause by denaturing of the protein at the liquid/air and liquid/solid interfaces)), deamidation (e.g. Asn deamidation), oxidation (e.g. Met oxidation), isomerization (e.g. Asp isomeriation), denaturation, clipping/hydrolysis/fragmentation (e.g. hinge region fragmentation), succinimide formation, N-terminal extension, C-terminal processing, glycosylation differences, and the like.

A stable formulation can contribute to a low immunogenicity of an anti-α4β7 antibody. An immunogenic anti-α4β7 antibody can lead to a human-anti-human antibody (HAHA) response in human subjects or patients. Patients who develop a HAHA response to an anti-α4β7 antibody can have adverse events (e.g., site infusion reaction) upon treatment or can eliminate anti-α4β7 antibody quickly, resulting in a lower dose than planned by treatment. A report (Feagen et al. (2005) N. Engl. J. Med. 352:2499-2507) of early study of an anti-α4β7 antibody treatment indicated that human antihuman antibodies developed by week 8 in 44% of treated patients. The antibody in this study was stored as a liquid and did not contain any polysorbate.

In some embodiments, the formulation can increase the proportion of HAHA 2 negative patients to at least 40%, at least 50%, at least 60%, at least 70%, at least 80% or at least 90% of patients compared to the HAHA results of a less stable formulation.

In some embodiments, an anti-α4β7 antibody formulation has ≥50% major charged isoform, ≥55% major charged isoform, or 65 to 70% major charged isoform. In other aspects, a stable anti-α4β7 antibody formulation has ≤45% acidic charged isoforms, ≤40% acidic charged isoforms, ≤30% acidic charged isoforms or 22 to 28% acidic isoforms. In still other aspects, a stable anti-α4β7 antibody formulation has ≤25% basic isoforms, ≤20% basic isoforms, ≤15% basic isoforms, about 5% basic isoforms or about 10% basic isoforms. In one aspect, a stable anti-α4β7 antibody formulation has ≥55% major isoform, ≤30% acidic isoforms and/or ≤20% basic isoforms, e.g., as determined by CEX. In another aspect, a stable anti-α4β7 antibody formulation has ≥50% major isoform, ≤45% acidic isoforms and/or ≤10% basic isoforms, e.g., as determined by cIEF.

In some aspects, an anti-α4β7 antibody dry, solid formulation has ≤10% moisture content, ≤5% moisture content or ≤2.5% moisture content. The time required for reconstitution is ≤60 minutes, ≤50 minutes or ≤40 minutes or ≤30 minutes or ≤20 minutes.

Monomeric content and/or aggregate content (e.g., as dimers, trimers, tetramers, pentamers, oligomers and higher-order aggregates), i.e., in the liquid formulation, or in a dry formulation after reconstitution, can be measured by SEC, MALDI-TOF MS, analytical ultracentrifugation, light scattering (DLS or MALLS), or nanoscale measurement, such as nanoparticle tracking analysis NTA, NanoSight Ltd, Wiltshire, UK). Resolution, characterization and quantification of aggregate can be achieved in a number of ways, including increasing the length of the SEC column separation, e.g., by a longer column or by serial attachment of a second or more SEC column(s) in line with the initial analytical SEC column, supplementing SEC quantification of monomers with light scattering, or by using NTA.

In one embodiment, an anti-α4β7 antibody formulation has ≥90% monomeric antibody, ≥95% monomeric antibody, or 97 to 99% monomeric antibody. In another embodiment, the majority of the material in an anti-α4β7 antibody formulation has an average radius of ≤20 nm, ≤15 nm, ≤10 nm, or about 5 to about 7 nm. In one aspect, an anti-α4β7 antibody formulation has ≥80% amount heavy plus light chain by protein analysis. In one aspect, there is ≥90% heavy plus light chain. In another aspect, an anti-α4β7 antibody formulation has ≤10% aggregate, ≤5% aggregate, ≤2.5% aggregate ≤1.5% aggregate, ≤1.0% aggregate or ≤0.5% aggregate. In another aspect, a stable anti-α4β7 antibody formulation has ≥96% monomer and/or ≤2.5% aggregate. In yet another aspect, a stable anti-α4β7 antibody formulation has about 99% monomer and/or about <1% aggregate.

Particle sizes, e.g., of aggregates or undissolved excipient, i.e., in reconstituted formulation can be measured by light obscuration (e.g., liquid particle counting system (HIAC) by Hach Ultra Analytics (Grants Pass, OR)), microscopy, coulter counter, or digital (e.g., flow-based) microscopic imaging based system such as microfluidics imaging (MFI) by Brightwell (Ottawa, CA) or FLOWCAM® Image particle analyzer by Fluid Imaging Technologies (Yarmouth, ME). In one aspect, particle size in an anti-α4β7 antibody preparation is about 30 μm, about 25 μm, about 10 μm, about 5 μm, about 2 μm or 1 μm or less. The amount of particles should be minimized in antibody formulations. In one aspect, the anti-α4β7 antibody formulation has less than 6000 particles ≥10 μm and less than 600 particles ≥25 μm diameter in one dose (U.S. Pharmacopoeia Chp. 788, light obscuration counting method; half those amounts by microscopic quantification 1 method). In yet another aspect, an amount of particles per milliliter, e.g., by MFI measurement, in a dose of an anti-α4β7 antibody formulation, e.g., reconstituted formulation is about 500 to about 2000, or about 1000 to about 3000 of 2-10 μm particles per ml, about 50 to about 350 ≥10 μm particles per ml and about 0 to about 50 of ≥25 μm particles per ml.

In one embodiment, an anti-α4β7 antibody formulation has a binding affinity of about 60% to about 140% of the reference standard anti-α4β7 antibody. In one aspect, an anti-α4β7 antibody in a formulation described herein binds to α4β7, e.g., on a cell (WO98/06248 or U.S. Pat. No. 7,147,851), at a value of about 80% to about 120% of the reference standard. In another embodiment, an anti-α4β7 antibody formulation has the ability to inhibit at least 50% or at least 60% of the binding of a cell expressing α4β7 integrin to MAdCAM, e.g., MAdCAM-1, a MAdCAM-Ig chimera (see U.S. Patent Application Publication No. 20070122404, also for reference standard examples).

As noted above, freezing of the formulation is specifically contemplated herein. Hence, the formulation can be tested for stability upon freezing and thawing. Accordingly, the antibody in a liquid formulation may be stable upon freezing and thawing the formulation, for example the antibody can be stable after one, two, three, four, five or more freeze/thaw cycles.

In some embodiments, the formulation is a liquid formulation comprising at least about 50 mg/ml to about 100 mg/ml anti-α4β7 antibody, a buffering agent (e.g., histidine), and at least about 9% (w/w) non-reducing sugar (e.g, sucrose, trehalose or mannitol). In one embodiment, the formulation comprises at least about 50 to about 80 mg/ml, about 60 mg/ml anti-α4β7 antibody, a buffering agent (e.g., histidine), a free amino acid (e.g., arginine) and at least about 9% or 10% (w/w) non-reducing sugar (e.g, sucrose, trehalose or mannitol).

In another embodiment, the formulation comprises at least about 60 mg/ml anti-α4β7 antibody, a buffering agent (e.g., histidine), a free amino acid (e.g., arginine) and at least about 10% (w/w) non-reducing sugar (e.g., sucrose, trehalose or mannitol). In such embodiments, the buffer concentration is about 15 to about 75 mM, about 25 to about 65 mM, or about 50 mM. The free amino acid concentration is about 50 to about 250 mM, about 75 to about 200 mM, about 100 to about 150 mM or about 125 mM.

In one embodiment, the formulation is a dry, solid formulation (e.g., a lyophilized formulation), comprising a mixture of a non-reducing sugar, an anti-α4β7 antibody, histidine, arginine, and polysorbate 80, and the molar ratio of non-reducing sugar to anti-α4β7 antibody (mole:mole) is greater than 600:1.

In another embodiment, the formulation is a dry, solid, amorphous formulation (e.g., a lyophilized formulation), comprising a mixture of a non-reducing sugar, an anti-α4β7 antibody, histidine, arginine, and polysorbate 80, and the molar ratio of non-reducing sugar to anti-α4β7 antibody (mole:mole) is greater than 600:1.

In one embodiment, the formulation is a lyophilized formulation comprising a non-reducing sugar, an anti-α4β7 antibody, histidine, arginine and polysorbate 80, and the molar ratio of non-reducing sugar to anti-α4β7 antibody (mole:mole) in the formulation is greater than 600:1.

In one embodiment, the formulation is a lyophilized formulation comprising a non-reducing sugar, an anti-α4β7 antibody, histidine, arginine and polysorbate 80, wherein the molar ratio of non-reducing sugar to anti-α4β7 antibody (mole:mole) in the formulation is greater than 600:1 and the molar ratio of arginine to anti-α4β7 antibody (mole:mole) in the formulation is greater than 250:1.

In one embodiment, the formulation is a liquid formulation and comprises at least about 60 mg/ml anti-α4β7 antibody, at least about 10% (w/v) non-reducing sugar, and at least about 125 mM of one or more free amino acids.

In one embodiment, the formulation is a liquid formulation and comprises at least about 60 mg/ml anti-α4β7 antibody, at least about 10% (w/v) non-reducing sugar, and at least about 175 mM of one or more free amino acids.

In one embodiment, the formulation is a liquid formulation and comprises between about 60 mg/ml to about 80 mg/ml anti-α4β7 antibody, a buffering agent and at least about 10% (w/w) sugar.

In one embodiment, the formulation is a liquid formulation and comprises between about 60 mg/ml to about 80 mg/ml anti-α4β7 antibody, histidine and at least about 10% (w/w) sucrose.

In one embodiment, the formulation is lyophilized and stored as a single dose in one vial. The vial is desirably stored at about 2-8° C. until it is administered to a subject in need thereof. The vial may for example be a 20 or 50 cc vial (for example for a 60 mg/ml dose). The vial may contain at least about 120 mg, at least about 180 mg, at least about 240 mg, at least about 300 mg, at least about 360 mg, at least about 540 mg, or at least about 900 mg of anti-α4β7 antibody. In one aspect, the vial contains about 300 mg of anti-α4β7 antibody.

One or more other pharmaceutically acceptable carriers, excipients or stabilizers such as those described in *Remington: The Science and Practice of Pharmacy,* 21st Edition, Hendrickson, R. Ed. (2005) may be included in the formulation provided that they do not adversely affect the desired characteristics of the formulation. Acceptable carriers, excipients or stabilizers arc nontoxic to recipients at the dosages and concentrations employed and include; additional buffering agents; co-solvents; antioxidants including ascorbic acid and methionine; chelating agents such as EDTA; metal complexes (e.g., Zn-protein complexes); biodegradable polymers such as polyesters; preservatives; and/or salt-forming counterions such as sodium.

α4β7 Antibodies

Anti-α4β7 antibodies suitable for use in the formulations include antibodies from any desired source, such as fully human antibodies, murine antibodies, rabbit antibodies and the like, and any desired engineered antibodies, such as chimeric antibodies, humanized antibodies, and the like. Antigen-binding fragments of any of these types of antibodies, such as Fab, Fv, scFv, Fab' and $F(ab')_2$ fragments, are also suitable for use in the formulations.

The anti-α4β7 antibody can bind to an epitope on the α4 chain (e.g., humanized MAb 21.6 (Bendig et al., U.S. Pat. No. 5,840,299), on the 37 chain (e.g., FIB504 or a humanized derivative (e.g., Fong et al., U.S. Pat. No. 7,528,236)), or to a combinatorial epitope formed by the association of the α4 chain with the 37 chain. In one aspect, the antibody binds a combinatorial epitope on the α4β7 complex, but docs not bind an epitope on the α4 chain or the β7 chain unless the chains are in association with each other. The association of α4 integrin with β7 integrin can create a combinatorial epitope for example, by bringing into proximity residues present on both chains which together comprise the epitope or by conformationally exposing on one chain, e.g., the α4 integrin chain or the 37 integrin chain, an epitopic binding site that is inaccessible to antibody binding in the absence of the proper integrin partner or in the absence of integrin activation. In another aspect, the anti-α4β7 antibody binds both the α4 integrin chain and the 37 integrin chain, and thus, is specific for the α4β7 integrin complex. Such antibodies can bind α4β1, and/or not bind $\alpha_E$β7, for example. In another aspect, the anti-α4β7 antibody binds to the same or substantially the same epitope as the Act-1 antibody (Lazarovits, A. I. et al., *J. immunol.,* 133(4): 1857-1862 (1984), Schweighoffer et al., *J Immunol.,* 151(2): 717-729, 1993; Bednarczyk et al., *J Biol. Chem.,* 269(11): 8348-8354, 1994). Murine ACT-1 Hybridoma cell line, which produces the murine Act-1 monoclonal antibody, was deposited under the provisions of the Budapest Treaty on Aug. 22, 2001, on behalf Millennium Pharmaceuticals, Inc., 40 Landsdowne Street, Cambridge, Mass. 02139, U.S.A., at the American Type Culture Collection, 10801 University Boulevard, Manassas, Va. 20110-2209, U.S.A., under Accession No. PTA-3663. In another aspect, the anti-α4β7 antibody is a human antibody or an α4β7 binding protein using the CDRs provided in U.S. Patent Application Publication No. 2010/0254975.

In one aspect, the anti-α4β7 antibody inhibits binding of α4β7 to one or more of its ligands (e.g. the mucosal addressin, e.g., MAdCAM (e.g., MAdCAM-1), fibronectin, and/or vascular addressin (VCAM)). Primate MAdCAMs are described in the PCT publication WO 96/24673, the entire teachings of which are incorporated herein by this reference. In another aspect, the anti-α4β7 antibody inhibits binding of α4β7 to MAdCAM (e.g., MAdCAM-1) and/or fibronectin without inhibiting the binding of VCAM.

In one aspect, the anti-α4β7 antibodies for use in the formulations are humanized versions of the mouse Act-1 antibody. Suitable methods for preparing humanized antibodies are well-known in the art. Generally, the humanized anti-α4β7 antibody will contain a heavy chain that contains the 3 heavy chain complementarity determining regions (CDRs, CDR1, SEQ ID NO:8, CDR2, SEQ ID NO:9 and CDR3, SEQ ID NO:10) of the mouse Act-1 antibody and suitable human heavy chain framework regions; and also contain a light chain that contains the 3 light chain CDRs (CRD1, SEQ ID NO:11, CDR2, SEQ ID NO:12 and CDR3, SEQ ID NO:13) of the mouse Act-1 antibody and suitable human light chain framework regions. The humanized Act-1 antibody can contain any suitable human framework regions, including consensus framework regions, with or without amino acid substitutions. For example, one or more of the frame work amino acids can be replaced with another amino acid, such as the amino acid at the corresponding position in the mouse Act-1 antibody. The human constant region or portion thereof, if present, can be derived from the κ or λ light chains, and/or the γ (e.g., γ1, γ2, γ3, γ4), μ, α (e.g., α1, α2), 6 or F heavy chains of human antibodies, including allelic variants. A particular constant region (e.g., IgG1), variant or portions thereof can be selected in order to tailor effector function. For example, a mutated constant region (variant) can be incorporated into a fusion protein to minimize binding to Fe receptors and/or ability to fix complement (see e.g., Winter et al., GB 2,209,757 B; Morrison et al., WO 89/07142; Morgan et al., WO 94/29351, Dec. 22, 1994). Humanized versions of Act-1 antibody were described in PCT publications nos. WO98/06248 and WO07/61679, the entire teachings of each of which are incorporated herein by this reference.

In another aspect, the anti-α4β7 humanized antibodies for use in the formulation comprise a heavy chain variable region comprising amino acids 20 to 140 of SEQ ID NO:2, and a light chain variable region comprising amino acids 20 to 131 of SEQ ID NO:4 or amino acids 21 to 132 of SEQ ID NO:5. If desired, a suitable human constant region(s) can be present. For example, the humanized anti-α4β7 antibody can comprise a heavy chain that comprises amino acids 20 to 470 of SEQ ID NO:2 and a light chain comprising amino acids 21 to 239 of SEQ ID NO:5. In another example, the humanized anti-α4β7 antibody can comprise a heavy chain that comprises amino acids 20 to 470 of SEQ ID NO:2 and a light chain comprising amino acids 20 to 238 of SEQ ID NO:4. FIG. 4 shows an alignment which compares the generic light chains of human antibodies with murine antibodies. The alignment illustrates that the humanized light chain of vedolizumab (e.g., Chemical Abstract Service (CAS, American Chemical Society) Registry number 943609-66-3), with two mouse residues switched for human residues, is more human than the light chain of LDP-02 (FIG. 3). In addition, LDP-02 has the somewhat hydrophobic, flexible alanine 114 and a hydrophilic site (Aspartate 115) that is replaced in vedolizumab with the slightly hydrophilic hydroxyl-containing threonine 114 and hydrophobic, potentially inward facing valine 115 residue.

Further substitutions to the antibody sequence can be, for example, mutations to the heavy and light chain framework regions, such as a mutation of isoleucine to valine on residue 2 of SEQ ID NO:14; a mutation of methionine to valine on residue 4 of SEQ ID NO:14; a mutation of alanine to glycine on residue 24 of SEQ ID NO:15; a mutation of arginine to lysine at residue 38 of SEQ ID NO:15; a mutation of alanine to arginine at residue 40 of SEQ ID NO:15; a mutation of methionine to isoleucine on residue 48 of SEQ ID NO:15; a mutation of isoleucine to leucine on residue 69 of SEQ ID NO:15; a mutation of arginine to valine on residue 71 of SEQ ID NO:15; a mutation of threonine to isoleucine on residue 73 of SEQ ID NO:15; or any combination thereof; and replacement of the heavy chain CDRs with the CDRs (CDR1, SEQ ID NO:8, CDR2, SEQ ID NO:9 and CDR3, SEQ ID NO:10) of the mouse Act-1 antibody; and replacement of the light chain CDRs with the light chain CDRs (CDR1, SEQ ID NO:11, CDR2, SEQ ID NO:12 and CDR3, SEQ ID NO:13) of the mouse Act-1 antibody.

In some embodiments, the anti-α4β7 humanized antibodies for use in the formulation comprise a heavy chain variable region that has about 95%, 96%, 97%, 98%, or 99% sequence identity to amino acids 20 to 140 of SEQ ID NO:2, and a light chain variable region that has about 95%, 96%, 97%, 98%, or 99% sequence identity to amino acids 20 to 131 of SEQ ID NO:4 or amino acids 21 to 132 of SEQ ID NO:5. Amino acid sequence identity can be determined using a suitable sequence alignment algorithm, such as the Lasergene system (DNASTAR, Inc., Madison, Wis.), using the default parameters. In an embodiment, the anti-α4β7 antibody for use in the formulation is vedolizumab (CAS, American Chemical Society, Registry number 943609-66-3).

Other α4β7 antibodies may also be used in the formulations and dosing regimes described herein. For example, the α4β7 antibodies described in US 2010/0254975 (Amgen, Inc.), incorporated by reference herein in its entirety, are suitable for use in the formulations and methods of treating inflammatory bowel disease in an individual.

The anti-α4β7 antibody can be produced by expression of nucleic acid sequences encoding each chain in living cells, e.g., cells in culture. A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an anti-α4β7 antibody in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3, NS0 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). For example, mammalian cells such as Chinese hamster ovary cells (CHO), in conjunction with a vector such as the major intermediate early gene promoter element from human cytomegalovirus is an effective expression system for antibodies (Foecking et al., *Gene* 45:101 (I 986); Cockett et al., *Bio/Technology* 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., *EMBO J.* 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, *J Biol. Chem.* 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, *Proc. Natl. Acad Sci. USA* 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to Chinese hamster ovary (CHO), NS0, HeLa, VERY, baby hamster kidney (BHK), monkey kidney (COS), MDCK, 293, 3T3, WI38, human hepatocellular carcinoma cells (e.g., Hep 02), breast cancer cell lines such as, for example, BT483, Hs578T, HTB2, BT20 and T47D, and normal mammary gland cell line such as, for example, CRL7030 and Hs578Bst.

The glycosylation machinery of different cell types can produce antibodies with different glycosylation composition than in another cell type, or no glycosylation, as with bacterial cells. In one aspect, cell types for production of the anti-$\alpha 4\beta 7$ antibody are mammalian cells, such as NS0 or CHO cells. In one aspect, the mammalian cells can comprise the deletion of an enzyme involved in cell metabolism and the exogenous gene of interest can be operably linked to a replacement enzyme, e.g., in a construct or vector for introduction into the cells, e.g., by transformation or transfection. The construct or vector with the exogenous gene confers to the cells which host the construct or vector a selection advantage to encourage production of the polypeptide encoded by the exogenous gene. In one embodiment, CHO cells are DG44 cells (Chasin and Urlaub (1980) PNAS USA 77:4216), comprising the deletion or inactivation of the dihydrofolate reductase gene. In another embodiment, CHO cells are CHO Kl cells comprising the deletion or inactivation of the glutamine synthase gene (see, e.g., U.S. Pat. No. 5,122,464 or U.S. Pat. No. 5,827,739).

Solid Formulations

Solid formulations of the invention are generally prepared by drying a liquid formulation. Any suitable method of drying can be used, such as lyophilization or spray drying. Lyophilization involves freezing a liquid formulation, usually in the container that will be used to store, ship and distribute the formulation (e.g., a vial). (See, e.g., Gatlin and Nail in *Protein Purification Process Engineering*, ed. Roger G. Harrison, Marcel Dekker Inc., 317-367 (1994).) Once the formulation is frozen, the atmospheric pressure is reduced and the temperature is adjusted to allow removal of the frozen solvent e.g., through sublimation. This step of the lyophilization process is sometimes referred to as primary drying. If desired, the temperature can then be raised to remove any solvent that is still bound to the dry formulation by evaporation. This step of the lyophilization process is sometimes referred to as secondary drying. When the formulation has reached the desired degree of dryness, the drying process is concluded and the containers are sealed. The final solid formulation is sometimes referred to as a "lyophilized formulation" or a "cake." The lyophilization process can be performed using any suitable equipment. Suitable lyophilization equipment is available from a number of commercial sources (e.g., SP Scientific, Stone Ridge, NY).

A variety of suitable apparatuses can be used to dry liquid formulations to produce a solid (e.g., lyophilized) formulation. Generally, lyophilized formulations arc prepared by those of skill in the art using a sealed chamber that contains shelves, on which vials of the liquid formulation to be dried are placed. The temperature of the shelves, as well as cooling and heating rate can be controlled, as can the pressure inside the chamber. It will be understood that various process parameters discussed herein refer to processes performed using this type of apparatus. Persons of ordinary skill can easily adapt the parameters described herein to other types of drying apparatuses if desired.

Suitable temperatures and the amount of vacuum for primary and secondary drying can be readily determined by a person of ordinary skill. In general, the formulation is frozen at a temperature of about −30° C. or less, such as −40° C. or −50° C. The rate of cooling can affect the amount and size of ice crystals in the matrix. Primary drying is generally conducted at a temperature that is about 10° C., about 20° C., about 30° C., about 40° C. or about 50° C. warmer than the freezing temperature. In one aspect, the primary drying conditions can be set to maintain the anti-$\alpha 4\beta 7$ antibody below the glass transition temperature or collapse temperature of the formulation. Above the collapse temperature, the amorphous frozen matrix can flow (collapse), with a result that the protein molecules may not be surrounded by a rigid, solid matrix, and the protein molecules may not be stable in the collapsed matrix. Also, the formulation can be difficult to fully dry if collapse occurs. The resulting higher amounts of moisture in the formulation can lead to higher rates of protein degradation and a decrease in the amount of time that the lyophilized product can be stored before its quality diminishes to unacceptable levels. In one aspect, the shelf temperature and chamber pressure are selected to maintain the product temperature below the collapse temperature during primary drying. The glass transition temperature of a frozen formulation can be measured by methods known in the art, e.g., by differential scanning calorimetry (DSC). The collapse temperature can be measured by methods known in the art, e.g. freeze-drying microscopy. The ratio of non-reducing sugar to protein (mole:mole) and the amounts of other formulation components will impact the glass transition temperature and collapse temperature. In some embodiments, a glass transition temperature for an $\alpha 4\beta 7$ antibody formulation is about −35°

C. to about −10° C., about −35° C. to about −25° C., or about −35° C. to about −29° C. In another embodiment, the glass transition temperature of an α4β7 antibody formulation is about −29° C. In some embodiments, the glass transition temperature of an α4β7 antibody formulation is about −30° C., about −31° C., about −32° C., about −33° C., about −34° C., about −35° C. or about −36° C. In some embodiments, a collapse temperature of an α4β7 antibody formulation is about −30° C. to about 0° C., about −28° C. to about −25° C., or about −20° C. to about −10° C. In another embodiment, the collapse temperature of an α4β7 antibody formulation is about −26° C. Without wishing to be bound by any particular theory, the faster the ramp-up rate, the higher the collapse temperature of the product. The primary drying step can remove at least 50%, at least 60%, at least 70% or more of the solvent. In one aspect, the primary drying step removes more than 80% of the solvent from the anti-α4β7 antibody formulation.

Primary drying is dependent on shelf temperature and pressure. The conditions for primary drying can be determined empirically with lyophilization under different process parameters. Primary drying may also be mathematically modeled based on product temperature. Mass and heat transfer equations (Milton, et al. (1997) *PDA J of Pharm Sci & Tech,* 51: 7-16), coupled with knowledge of Rp and Kv, allow for understanding the combination and interaction of input variables including process input variables such as shelf temperature and pressure and formulation variables which are captured in the Rp value. These models can aid in determining the parameters to be used for an efficient process based on the limitations of the product temperature by the collapse temperature and equipment capability.

$$\frac{dm}{dt} = \frac{A_p(P_o - P_c)}{R_p} \qquad \text{Equation 1}$$

$$\ln P_0 = -6144.96/T_p + 24.0185 \qquad \text{Equation 2}$$

$$\frac{dQ}{dt} = A_v K_v (T_s - T_p) \qquad \text{Equation 3}$$

$$\frac{dQ}{dt} = \Delta H_s \frac{dm}{dt} \qquad \text{Equation 4}$$

Equation 1 relates the sublimation rate (dm/dt) during primary drying to the internal cross-sectional area of the container ($A_p$), the vapor pressure of ice ($P_o$), the pressure of the chamber ($P_c$), and an area normalized mass transfer resistance for the cake and stopper ($R_p$). $P_o$ at the sublimation interface can be determined from Equation 2, where $P_o$ is related to the temperature of the product ice at the sublimation interface, which is an approximation from the product temperature ($T_p$), which can be measured with a thermocouple at the bottom of the vial or can be derived from the equations above when the other variables are determined. Equation 3 relates the heat transfer rate from the shelf to the vials, where $A_v$ is the area of the vial, $K_v$ is the heat transfer coefficient of the vial, $T_s$ is the temperature of the shelf and $T_p$ is the product temperature. Equation 4 couples the heat and mass transfer equations, where $\Delta H_s$ is the heat of sublimation.

As seen from the equations for primary drying, the shelf temperature ($T_s$), the product temperature ($T_p$), the chamber pressure ($P_c$), the mass transfer resistance of the cake ($R_p$), and the heat transfer coefficient ($K_v$) can affect the sublimation rate.

An optional step after freezing and before primary drying is annealing. In this step the shelf temperature of the lyophilizer is raised above the glass transition of the formulation for a short period of time, e.g., about 2 to 6 hours, about 3 to 5 hours, or about 4 hours, then the shelf temperature is lowered again to below the glass transition temperature of the formulation. Annealing can be used to crystallize bulking agents and to form larger, more uniform ice crystals. The annealing process can affect reconstitution time because the annealed, dried cake has a higher surface area than the unannealed, dried cake. An annealing step of an α4β7 antibody formulation can be at about −30° C. to about −10° C. or about −25° C. to about −15° C. In one aspect, an annealing temperature for an α4β7 antibody formulation is about −20° C.

Secondary drying is generally conducted at a temperature that is above the freezing temperature of the liquid formulation. For example, secondary drying can be conducted at about 10° C., about 20° C., about 30° C., about 40° C. or about 50° C. In one aspect, the temperature for secondary drying is ambient temperature, e.g., 20-30° C. The time for secondary drying should be sufficient to reduce the amount of moisture to <5%.

In another aspect, the lyophilization cycle includes freezing at about −45° C., annealing at about −20° C., refreezing at about −45° C., primary drying at about −24° C. and 150 mTorr, and secondary drying at about 27° C. and 150 mTorr.

$R_p$ is affected by the solids content of the frozen DP and by the DP's thermal history (freeze, anneal, and refreeze stages) which affects the pore structure of the cake. The thermal history can also affect the secondary drying stage, where a larger surface area can aid in desorption of water (Pikal, et al. (1990) Int. J. Pharm., 60: 203-217). Useful process parameters to control during the primary and secondary lyophilization stages can be the shelf temperature and chamber pressure during each stage of the drying cycle.

For scale-up, freeze dryer load and solid content can affect the drying cycle. Primary drying time can be affected by the solids content in the formulation. At higher solids contents, e.g., where overall solids (excipients and/or protein) concentrations vary more than 10 w/v % or more than 15 w/v %, e.g., 50 to 100% variance from formulations whose drying time is determined, the drying time can be affected. For example, a high solids content formulation can have a longer drying time than a low solids content formulation. In some embodiments, the percent usage of freeze dryer capacity can range from about 25 to about 100%. At higher loading % of capacity, the primary drying time can increase up to 2-fold in comparison to a lower loading % capacity. The differences between the primary drying times at different load % increases as the solids content increases. In one embodiment, the solids content is less than 20-25% and the load is from 25-100%.

Vial size can be selected based on the surface area which will be exposed to the shelf and to the vacuum during lyophilization. Drying time is directly proportional to cake height, thus the vial size may be chosen based upon what is determined to be a reasonable cake height. A vial with a large diameter relative to volume can provide a high amount of contact with the shelf for efficient heat transfer during the lyophilization cycle. A dilute antibody solution in a high volume of liquid will require more time for drying. A balance in vial size versus formulation volume needs to be struck, because larger vials can be more expensive to store and ship and have a larger headspace to formulation ratio and may expose a high proportion of the formulation to the degradative effects of moisture during long term storage. For a 300 mg dose, anti-α4β7 antibody formulation can have a volume of 3 ml, 5 ml, 6 ml, 10 ml, 20 ml, 50 ml or 100 ml prior to lyophilization. In one aspect, the vial size is 20 ml for a 60 mg/ml solution in a 300 mg dose.

After lyophilization, the vial can be sealed, e.g., stoppered, under a vacuum. Alternatively, a gas, e.g., dry air or nitrogen, can be allowed into the vial prior to sealing. Where oxidation is a concern, the gas allowed into the lyophilization chamber can comprise a gas which retards or prevents oxidation of the lyophilized product. In one aspect, the gas is a non-oxygenated gas, e.g., nitrogen, or an inert gas, e.g., helium, neon, argon, krypton or xenon. In another aspect, the gas is nitrogen or argon.

In some embodiments, the pre-lyophilization anti-α4β7 antibody formulation volume is the same as the pre-administration reconstituted solution volume. For example, a formulation which is about 5.5 ml pre-lyophilization can be reconstituted to a volume of about 5.5 ml, by adding an amount of liquid, e.g. water or saline, that takes into account the volume of the dry solids. In other embodiments, it may be desirable to lyophilize the anti-α4β7 antibody formulation in a different volume than the reconstituted solution volume. For example, the anti-α4β7 antibody formulation can be lyophilized as a dilute solution, e.g. 0.25×, 0.5×, or 0.75× and reconstituted to 1× by adding less liquid, e.g., 75% less, half, or 25% less than the pre-lyophilization volume. In an embodiment, a 300 mg dose can be lyophilized as a 30 mg/ml antibody solution in 5% sucrose and reconstituted to a 60 mg/ml antibody solution in 10% sucrose. Alternatively, the lyophilized anti-α4β7 antibody formulation can be reconstituted into a more dilute solution than the pre-lyophilized formulation.

Treatment with the Antibody Formulation

In one aspect, the invention provides a method of treating a disease or disorder in a subject comprising administering to a subject the anti-α4β7 antibody formulation described herein in an amount effective to treat the disease or disorder, e.g., in humans. The human subject may be an adult (e.g., 18 years or older), an adolescent, or a child. The human subject may be a person 65 years or older. In contrast to alternative therapeutic dosing regimens, a human subject 65 years or older docs not require any modification of the dosing regimen described herein, and may be administered the conventional anti-α4β7 antibody formulation described herein.

The subject may have had a lack of an adequate response with, loss of response to, or was intolerant to treatment with an immunomodulator, a TNF-α antagonist, or combinations thereof. The patient may have previously received treatment with at least one corticosteroid (e.g., prednisone) for the inflammatory bowel disease. An inadequate response to corticosteroids refers to signs and symptoms of persistently active disease despite a history of at least one 4-week induction regimen that included a dose equivalent to prednisone 30 mg daily orally for 2 weeks or intravenously for 1 week. A loss of response to corticosteroids refers to two failed attempts to taper corticosteroids to below a dose equivalent to prednisone 10 mg daily orally. Intolerance of corticosteroids includes a history of Cushing's syndrome, osteopenia/osteoporosis, hyperglycemia, insomnia and/or infection.

An immunomodulator may be, for example, oral azathioprine, 6-mercaptopurine, or methotrexate. An inadequate response to an immunomodulator refers to signs and symptoms of persistently active disease despite a history of at least one 8 week regimen or oral azathioprine (≥1.5 mg/kg), 6-mercaptopurine (≥0.75 mg/kg), or methotrexate (≥12.5 mg/week). Intolerance of an immunomodulator includes, but is not limited to, nausea/vomiting, abdominal pain, pancreatitis, LFT abnormalities, lymphopenia, TPMT genetic mutation and/or infection.

In one aspect, the subject may have had a lack of an adequate response with, loss of response to, or was intolerant to treatment a TNF-α antagonist. A TNF-α antagonist is, for example, an agent that inhibits the biological activity of TNF-α, and preferably binds TNF-α, such as a monoclonal antibody, e.g., REMICADE (infliximab), HUMIRA (adalimumab), CIMZIA (certolizumab pegol), SIMPONJ (golimumab) or a circulating receptor fusion protein such as ENBREL (etanercept). An inadequate response to a TNF-α antagonist refers to signs and symptoms of persistently active disease despite a history of at least one 4 week induction regimen of infliximab 5 mg/kg IV, 2 doses at least 2 weeks apart; one 80 mg subcutaneous dose of adalimumab, followed by one 40 mg dose at least two weeks apart; or 400 mg subcutaneously of certolizumab pegol, 2 doses at least 2 weeks apart. A loss of response to a TNF-α antagonist refers to recurrence of symptoms during maintenance dosing following prior clinical benefit. Intolerance of a TNF-α antagonist includes, but is not limited to infusion related reaction, demyelination, congestive heart failure, and/or infection.

A loss of maintenance of remission, as used herein for ulcerative colitis subjects, refers to an increase in Mayo score of at least 3 points and a Modified Baron Score of at least 2.

In another aspect, the present invention provides anti-α4β7 antibody formulations which (1) can bind α4β7 integrin in vitro and/or in vivo; and (2) can modulate an activity or function of an α4β7 integrin, such as (a) binding function (e.g., the ability of α4β7 integrin to bind to MAdCAM (e.g., MAdCAM-1), fibronectin and/or VCAM-1) and/or (b) leukocyte infiltration function, including recruitment and/or accumulation of leukocytes in tissues (e.g., the ability to inhibit lymphocyte migration to intestinal mucosa}tissue). In one embodiment, an antibody in the formulation can bind an α4β7 integrin, and can inhibit binding of the α4β7 integrin to one or more of its ligands (e.g., MAdCAM (e.g., MAdCAM-1), VCAM-1, fibronectin), thereby inhibiting leukocyte infiltration of tissues (including recruitment and/or accumulation of leukocytes in tissues). In another embodiment, an antibody in the formulation can bind an α4β7 integrin, and can selectively inhibit binding of the α4β7 integrin to one or more of its ligands (e.g., MAdCAM (e.g., MAdCAM-1), VCAM-1, fibronectin), thereby inhibiting leukocyte infiltration of tissues (including recruitment and/or accumulation of leukocytes in tissues). Such anti-α4β7 antibody formulations can inhibit cellular adhesion of cells bearing an α4β7 integrin to vascular endothelial cells in mucosa}tissues, including gut-associated tissues, lymphoid organs or leukocytes (especially lymphocytes such as T or B cells) in vitro and/or in vivo. In yet another embodiment, the anti-α4β7 antibody formulation of the present invention can inhibit the interaction of α4β7 with MAdCAM (e.g., MAdCAM-1) and/or fibronectin. In still yet another embodiment, the anti-α4β7 antibody formulation of the present invention can inhibit the interaction of α4β7 with MAdCAM (e.g., MAdCAM-1) and/or fibronectin selectively, e.g., without inhibiting the interaction of α4β7 with VCAM.

The anti-α4β7 antibody formulations of the present invention can be used to modulate (e.g., inhibit (reduce or prevent)) binding function and/or leukocyte (e.g., lymphocyte, monocyte) infiltration function of α4β7 integrin. For example, humanized immunoglobulins which inhibit the binding of α4β7 integrin to a ligand (i.e., one or more ligands) can be administered according to the method in the treatment of diseases associated with leukocyte (e.g., lymphocyte, monocyte) infiltration of tissues (including recruitment and/or accumulation of leukocytes in tissues), particularly of tissues which express the molecule MAdCAM (e.g., MAdCAM-1).

An effective amount of an anti-α4β7 antibody formulation of the present invention (i.e., one or more) is administered to an individual (e.g., a mammal, such as a human or other primate) in order to treat such a disease. For example, inflammatory diseases, including diseases which are associated with leukocyte infiltration of the gastrointestinal tract (including gut-associated endothelium), other mucosal tissues, or tissues expressing the molecule MAdCAM (e.g., MAdCAM-1) (e.g., gut-associated tissues, such as venules of the lamina propria of the small and large intestine; and mammary gland (e.g., lactating mammary gland)), can be treated according to the present method. Similarly, an individual having a disease associated with leukocyte infiltration of tissues as a result of binding of leukocytes to cells (e.g., endothelial cells) expressing MAdCAM (e.g., MAdCAM-1) can be treated according to the present invention.

In one embodiment, diseases which can be treated accordingly include inflammatory bowel disease (IBD), such as ulcerative colitis, Crohn's disease, ileitis, Celiac disease, nontropical Sprue, enteropathy associated with seronegative arthropathies, microscopic or collagenous colitis, eosinophilic gastroenteritis, or pouchitis resulting after proctocolectomy, and ileoanal anastomosis. Preferably, the inflammatory bowel disease is Crohn's disease or ulcerative colitis. The ulcerative colitis may be moderate to severely active ulcerative colitis. Treatment may result in mucosal healing in patients suffering from moderate to severely active ulcerative colitis. Treatment may also result in a reduction, elimination, or reduction and elimination of corticosteroid use by the patient.

Pancreatitis and insulin-dependent diabetes mellitus are other diseases which can be treated using the formulations of the invention. It has been reported that MAdCAM (e.g., MAdCAM-1) is expressed by some vessels in the exocrine pancreas from NOD (nonobese diabetic) mice, as well as from BALB/c and SJL mice. Expression of MAdCAM-1 was reportedly induced on endothelium in inflamed islets of the pancreas of the NOD mouse, and MAdCAM-1 was the predominant addressin expressed by NOD islet endothelium at early stages of insulitis (Hanninen, A., et al., *J Clin. Invest.,* 92: 2509-2515 (1993)). Treatment of NOD mice with either anti-MAdCAM (e.g., anti-MAdCAM-1) or anti 7 antibodies prevented the development of diabetes (Yang et al., *Diabetes,* 46:1542-1547 (1997)). Further, accumulation of lymphocytes expressing α4β7 within islets was observed, and MAdCAM-1 was implicated in the binding of lymphoma cells via α4β7 to vessels from inflamed islets (Hanninen, A., et al., *J Clin. Invest.,* 92: 2509-2515 (1993)) or to the gastrointestinal tract in mantle cell lymphoma (Geissmann et al., *Am. J Pathol.,* 153:1701-1705 (1998)).

Examples of inflammatory diseases associated with mucosal tissues which can be treated using a formulation of the invention include cholecystitis, cholangitis (Adams and Eksteen *Nature Reviews* 6:244-251 (2006) Grant et al., *Hepatology* 33:1065-1072 (2001)), e.g., primary sclerosing cholangitis, Behcet's disease, e.g., of the intestine, or pericholangitis (bile duct and surrounding tissue of the liver), and graft versus host disease (e.g., in the gastrointestinal tract (e.g., after a bone marrow transplant) (Petrovic et al. *Blood* 103:1542-1547 (2004)). As seen in Crohn's disease, inflammation often extends beyond the mucosal surface, accordingly chronic inflammatory diseases, such as sarcoidosis, chronic gastritis, e.g., autoimmune gastritis (Katakai et al., *Int. immunol.,* 14:167-175 (2002)) and other idiopathic conditions can be amenable to treatment.

The invention also relates to a method of inhibiting leukocyte infiltration of mucosal tissue. The invention also relates to a method for treating cancer (e.g., an α4β7 positive tumor, such as a lymphoma). Other examples of inflammatory diseases associated with mucosal tissues which can be treated using a formulation of the invention include mastitis (mammary gland) and irritable bowel syndrome.

Diseases or pathogens whose etiologies exploit the interaction of MAdCAM (e.g., MAdCAM-1) with α4β7 can be treated with an anti-α4β7 antibody in a formulation described herein. Examples of such diseases include immunodeficiency disorders, such as caused by human immunodeficiency virus (see e.g., WO2008140602).

A formulation of the invention is administered in an effective amount which inhibits binding of α4β7 integrin to a ligand thereof. For therapy, an effective amount will be sufficient to achieve the desired therapeutic (including prophylactic) effect (such as an amount sufficient to reduce or prevent α4β7 integrin-mediated binding and/or signaling, thereby inhibiting leukocyte adhesion and infiltration and/or associated cellular responses). An effective amount of an anti-α4β7 antibody, e.g., an effective titer sufficient to maintain saturation, e.g., neutralization, of α4β7 integrin, can induce clinical response or remission in inflammatory bowel disease. A formulation of the invention can be administered in a unit dose or multiple doses. The dosage can be determined by methods known in the art and can be dependent, for example, upon the individual's age, sensitivity, tolerance and overall well-being. Examples of modes of administration include topical routes such as nasal or inhalational or transdermal administration, enteral routes, such as through a feeding tube or suppository, and parenteral routes, such as intravenous, intramuscular, subcutaneous, intraarterial, intraperitoneal, or intravitreal administration. Suitable dosages for antibodies can be from about 0.1 mg/kg body weight to about 10.0 mg/kg body weight per treatment, for example about 2 mg/kg to about 7 mg/kg, about 3 mg/kg to about 6 mg/kg, or about 3.5 to about 5 mg/kg. In particular embodiments, the dose administered is about 0.3 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg.

The final dosage form, e.g., after dilution of the reconstituted antibody (e.g., in a saline or 5% dextrose infusion system) of the anti-α4β7 antibody can be about 0.5 mg/ml to about 5 mg/ml for administration. The final dosage form may be at a concentration of between about 1.0 mg/ml to about 1.4 mg/ml, about 1.0 mg/ml to about 1.3 mg/ml, about 1.0 mg/ml to about 1.2 mg/ml, about 1.0 to about 1.1 mg/ml, about 1.1 mg/ml to about 1.4 mg/ml, about 1.1 mg/ml to about 1.3 mg/ml, about 1.1 mg/ml to about 1.2 mg/ml, about 1.2 mg/ml to about 1.4 mg/ml, about 1.2 mg/ml to about 1.3 mg/ml, or about 1.3 mg/ml to about 1.4 mg/ml. The final dosage form may be at a concentration of about 0.6 mg/ml, 0.8 mg/ml, 1.0 mg/ml, 1.1 mg/ml, about 1.2 mg/ml, about 1.3 mg/ml, about 1.4 mg/ml, about 1.5 mg/ml, about 1.6 mg/ml, about 1.8 mg/ml or about 2.0 mg/ml. In one embodiment, the total dose is 180 mg. In another embodiment, the total dose is 300 mg. A 300 mg anti-α4β7 antibody dose can be diluted into a 250 ml saline or 5% dextrose solution for administration.

In some aspects, the dosing regimen has two phases, an induction phase and a maintenance phase. In the induction phase, the antibody or antigen-binding fragment thereof is administered in a way that quickly provides an effective amount of the antibody or antigen binding fragment thereof suitable for certain purposes, such as inducing immune tolerance to the antibody or antigen-binding fragment thereof or for inducing a clinical response and ameliorating inflammatory bowel disease symptoms. A patient can be administered an induction phase treatment when first being treated by an anti-α4β7 antibody, when being treated after a long absence from therapy, e.g., more than three months, more than four months, more than six months, more than nine months, more than one year, more than eighteen months or more than two years since anti-α4β7 antibody therapy or during maintenance phase of anti-α4β7 antibody therapy if there has been a return of inflammatory bowel disease symptoms, e.g., a relapse from remission of disease. In some embodiments, the induction phase regimen results in a higher mean trough serum concentration, e.g., the concentration just before the next dose, than the mean steady state trough serum concentration maintained during the maintenance regimen.

In the maintenance phase, the antibody or antigen-binding fragment thereof is administered in a way that continues the response achieved by induction therapy with a stable level of antibody or antigen-binding fragment thereof. A maintenance regimen can prevent return of symptoms or relapse of inflammatory bowel disease. A maintenance regimen can provide convenience to the patient, e.g., be a simple dosing regimen or require infrequent trips for treatment. In some embodiments, the maintenance regimen can include administration of the anti-α4β7 antibody or antigen-binding fragment thereof, e.g., in a formulation described herein, by a strategy selected from the group consisting of low dose, infrequent administration, self-administration and a combination any of the foregoing.

In one embodiment, e.g., during an induction phase of therapy, the dosing regimen provides an effective amount of an anti-α4β7 antibody or antigen-binding fragment in a formulation described herein for inducing remission of an inflammatory bowel disease in a human patient. In some embodiments, the effective amount of the anti-α4β7 antibody is sufficient to achieve about 5 μg/ml to about 60 μg/ml, about 15 μg/ml to about 45 μg/ml, about 20 μg/ml to about 30 μg/ml, or about 25 μg/ml to about 35 μg/ml mean trough serum concentration of the anti-α4β7 antibody by the end of the induction phase. The duration of induction phase can be about four weeks, about five weeks, about six weeks, about seven weeks, or about eight weeks of treatment. In some embodiments, the induction regimen can utilize a strategy selected from the group consisting of high dose, frequent administration, and a combination of high dose and frequent administration of the anti-α4β7 antibody or antigen-binding fragment thereof, e.g., in a formulation described herein. Induction dosing can be once, or a plurality of more than one dose, e.g., at least two doses. During induction phase, a dose can be administered once per day, every other day, twice per week, once per week, once every ten days, once every two weeks or once every three weeks. In some embodiments, the induction doses are administered within the first two weeks of therapy with the anti-α4β7 antibody. In one embodiment, induction dosing can be once at initiation of treatment (day 0) and once at about two weeks after initiation of treatment. In another embodiment, the induction phase duration is six weeks. In another embodiment, the induction phase duration is six weeks and a plurality of induction doses are administered during the first two weeks.

In some embodiments, e.g., when initiating treatment of a patient with severe inflammatory bowel disease (e.g., in patients who have failed anti-TNFα therapy), the induction phase needs to have a longer duration than for patients with mild or moderate disease. In some embodiments, the induction phase for a patient with a severe disease can have a duration of at least 6 weeks, at least 8 weeks, at least 10 weeks, at least 12 weeks or at least 14 weeks. In one embodiment, an induction dosing regimen for a patient with a severe disease can include a dose at week 0 (initiation of treatment), a dose at week 2 and a dose at week 6. In another embodiment, an induction dosing regimen for a patient with a severe disease can comprise a dose at week 0 (initiation of treatment), a dose at week 2, a dose at week 6 and a dose at week 10.

In one embodiment, e.g., during a maintenance phase of therapy, the dosing regimen maintains a mean steady state trough serum concentration, e.g., the plateau concentration just before the next dose, of about 5 to about 25 μg/mL, about 7 to about 20 μg/mL, about 5 to about 10 μg/mL, about 10 to about 20 μg/mL, about 15 to about 25 μg/mL or about 9 to about 13 μg/mL of anti-α4β7 antibody. In another embodiment, the dosing regimen e.g., during a maintenance phase of therapy, maintains a mean steady state trough serum concentration of about 20 to about 30 μg/mL, about 20 to about 55 μg/mL, about 30 to about 45 μg/mL, about 45 to about 55 μg/mL or about 35 to about 40 μg/mL of anti-α4β7 antibody.

The dose can be administered once per week, once every 2 weeks, once every 3 weeks, once every 4 weeks, once every 6 weeks, once every 8 weeks or once every 10 weeks. A higher or more frequent dose, e.g., once per week, once every 2 weeks, once every 3 weeks or once every 4 weeks can be useful for inducing remission of active disease or for treating a new patient, e.g., for inducing tolerance to the anti-α4β7 antibody. A less frequent dose, e.g., once every 4 weeks, once every 5 weeks, once every 6 weeks, once every 8 weeks or once every 10 weeks, can be useful for preventative therapy, e.g., to maintain remission of a patient with chronic disease. In one aspect, the treatment regimen is treatment at day 0, about week 2, about week 6 and every 4 or 8 weeks thereafter. In one embodiment, the maintenance regimen includes a dose every 8 weeks. In an embodiment, wherein a patient on a one dose every eight weeks maintenance regimen experiences a return of one or more disease symptoms, e.g., has a relapse, the dosing frequency can be increased, e.g., to once every 4 weeks.

The dose can be administered to the patient in about 20 minutes, about 25 minutes, about 30 minutes, about 35 minutes, or about 40 minutes.

The dosing regimen can be optimized to induce a clinical response and clinical remission in the inflammatory bowel disease of the patient. In some embodiments, the dosing regimen does not alter the ratio of CD4 to CD8 in cerebrospinal fluid of patients receiving treatment.

In some aspects, a durable clinical remission, for example, a clinical remission which is sustained through at least two, at least three, at least four visits with a caretaking physician within a six month or one year period after beginning treatment, may be achieved with an optimized dosing regimen.

In some aspects, a durable clinical response, for example, a clinical response which is sustained for at least 6 months, at least 9 months, at least a year, after the start of treatment, may be achieved with an optimized dosing regimen.

In one embodiment, the dosing regimen comprises an initial dose of 300 mg, a second subsequent dose of 300 mg about two weeks after the initial dose, a third subsequent dose of 300 mg at about six weeks after the initial dose, followed by a fourth and subsequent doses of 300 mg every four weeks or every eight weeks after the third subsequent dose.

In some embodiments, the method of treatment, dose or dosing regimen reduces the likelihood that a patient will develop a HAHA response to the anti-α4β7 antibody. The development of HAHA, e.g., as measured by antibodies reactive to the anti-α4β7 antibody, can increase the clearance of the anti-α4β7 antibody, e.g., reduce the serum concentration of the anti-α4β7 antibody, e.g., lowering the number of anti-α4β7 antibody bound to α4β7 integrin, thus making the treatment less effective. In some embodiments, to prevent HAHA, the patient can be treated with an induction regimen followed by a maintenance regimen. In some embodiments, there is no break between the induction regimen and the maintenance regimen. In some embodiments, the induction regimen comprises administering a plurality of doses of anti-α4β7 antibody to the patient. To prevent HAHA, the patient can be treated with a high initial dose, e.g., at least 1.5 mg/kg, at least 2 mg/kg, at least 2.5 mg/kg, at least 3 mg/kg, at least 5 mg/kg, at least 8 mg/kg, at least 10 mg/kg or about 2 to about 6 mg/kg, or frequent initial administrations, e.g., about once per week, about once every two weeks or about once every three weeks, of the standard dose when beginning therapy with an anti-α4β7 antibody. In some embodiments, the method of treatment maintains at least 30%, at least 40%, at least 50%, at least 60%, at least 70%, at least 80%, at least 90% or at least 95% of patients as HAHA-negative. In other embodiments, the method of treatment maintains patients as HAHA-negative for at least 6 weeks, at least 10 weeks at least 15 weeks, at least six months, at least 1 year, at least 2 years, or for the duration of therapy. In some embodiments, the patients, or at least 30%, at least 40%, at least 50% or at least 60% of patients who develop HAHA maintain a low titer, e.g., ≤125, of anti-α4β7 antibody. In an embodiment, the method of treatment maintains at least 70% of patients as HAHA-negative for at least 12 weeks after beginning therapy with an anti-α4β7 antibody.

The formulation may be administered to an individual (e.g., a human) alone or in conjunction with another agent. A formulation of the invention can be administered before, along with or subsequent to administration of the additional agent. In one embodiment, more than one formulation which inhibits the binding of α4β7 integrin to its ligands is administered. In such an embodiment, an agent, e.g., a monoclonal antibody, such as an anti-MAdCAM (e.g., anti-MAdCAM-1) or an anti-VCAM-1 monoclonal antibody can be administered. In another embodiment, the additional agent inhibits the binding of leukocytes to an endothelial ligand in a pathway different from the α4β7 pathway. Such an agent can inhibit the binding, e.g. of chemokine (C—C motif) receptor 9 (CCR9)-expressing lymphocytes to thymus expressed chemokine (TECK or CCL25) or an agent which prevents the binding of LFA-1 to intercellular adhesion molecule (ICAM). For example, an anti-TECK or anti-CCR9 antibody or a small molecule CCR9 inhibitor, such as inhibitors disclosed in PCT publication WO03/099773 or WO04/046092, or anti-ICAM-1 antibody or an oligonucleotide which prevents expression of ICAM, is administered in addition to a formulation of the present invention. In yet another embodiment, an additional active ingredient (e.g., an anti-inflammatory compound, such as sulfasalazine, azathioprine, 6-mercaptopurine, 5-aminosalicylic acid containing anti-inflammatories, another non-steroidal anti-inflammatory compound, a steroidal anti-inflammatory compound, or antibiotics commonly administered for control of IBD (e.g. ciprofloxacin, metronidazole), or another biologic agent (e.g. TNF alpha antagonists) can be administered in conjunction with a formulation of the present invention.

In an embodiment, the dose of the co-administered medication can be decreased over time during the period of treatment by the formulation comprising the anti-α4β7 antibody. For example, a patient being treated with a steroid (e.g. prednisone, prednisolone) at the beginning, or prior to, treating with the anti-α4β7 antibody formulation would undergo a regimen of decreasing doses of steroid beginning as early as 6 weeks of treatment with the anti-α4β7 antibody formulation. The steroid dose will be reduced by about 25% within 4-8 weeks of initiating tapering, by 50% at about 8-12 weeks and 75% at about 12-16 weeks of tapering during treatment with the anti-α4β7 antibody formulation. In one aspect, by about 16-24 weeks of treatment with the anti-α4β7 antibody formulation, the steroid dose can be eliminated. In another example, a patient being treated with an anti-inflammatory compound, such as 6-mercaptopurine at the beginning, or prior to, treating with the anti-α4β7 antibody formulation would undergo a regimen of decreasing doses of anti-inflammatory compound similar to the tapering regimen for steroid dosing as noted above.

In one embodiment, the method comprises administering an effective amount of a formulation of the invention to a patient. If the formulation is in a solid, e.g., dry state, the process of administration can comprise a step of converting the formulation to a liquid state. In one aspect, a dry formulation can be reconstituted, e.g., by a liquid as described above, for use in injection, e.g. intravenous, intramuscular or subcutaneous injection. In another aspect, a solid or dry formulation can be administered topically, e.g., in a patch, cream, aerosol or suppository.

The invention also relates to a method for treating a disease associated with leukocyte infiltration of tissues expressing the molecule MAdCAM (e.g., MAdCAM-1). The method comprises administering to a patient in need thereof an effective amount of an anti-α4β7 antibody formulation of the invention. In an embodiment, the disease is graft versus host disease. In some embodiments, the disease is a disease associated with leukocyte infiltration of tissues as a result of binding of leukocytes expressing α4β7 integrin to gut-associated endothelium expressing the molecule MAdCAM (e.g., MAdCAM-1). In other embodiments, the disease is gastritis (e.g., eosinophilic gastritis or autoimmune gastritis), pancreatitis, or insulin-dependent diabetes mellitus. In yet other embodiments, the disease is cholecystitis, cholangitis, or pericholangitis.

The invention also relates to a method for treating inflammatory bowel disease in a patient. In one embodiment, the method comprises administering to the patient an effective amount of an anti-α4β7 antibody formulation of the invention. In some embodiments, the inflammatory bowel disease is ulcerative colitis or Crohn's disease. In other embodiments, the inflammatory bowel disease is Celiac disease, enteropathy associated with seronegative arthropathies, microscopic or collagenous colitis, gastroenteritis (e.g., eosinophilic gastroenteritis), or pouchitis.

In some embodiments, treatment with an anti-α4β7 antibody does not alter the ratio of CD4:CD8 lymphocytes. CD4:CD8 ratios can be measured in blood, lymph node aspirate, and cerebro-spinal fluid (CSF). The CSF CD4+:

CD8+ lymphocyte ratios in healthy individuals are typically greater than or equal to about 1. (Svenningsson et al., *J Neuroimmunol.* 1995; 63:39-46; Svenningsson et al., *Ann Neurol.* 1993; 34:155-161). An immunomodulator can alter the CD4:CD8 ratio to less than 1.

Articles of Manufacture

In another aspect, the invention is an article of manufacture which contains the pharmaceutical formulation of the present invention and provides instructions for its use. The article of manufacture comprises a container. Suitable containers include, for example, bottles, vials (e.g., dual chamber vials, a vial of liquid formulation with or without a needle, a vial of solid formulation with or without a vial of reconstitution liquid with or without a needle), syringes (such as dual chamber syringes, preloaded syringes) and test tubes. The container may be formed from a variety of materials such as glass, metal or plastic. The container holds the formulation and a label on, or associated with, the container may indicate directions for use. In another embodiment, the formulation can be prepared for self-administration and/or contain instructions for self-administration. In one aspect, the container holding the formulation may be a single-use vial. In another aspect, the container holding the formulation may be a multi-use vial, which allows for repeat administration (e.g., from 2-6 administrations) of the formulation, e.g., using more than one portion of a reconstituted formulation. The article of manufacture may further include other materials desirable from a commercial and user standpoint, including other buffers, diluents, filters, needles, syringes and package inserts with instructions for use as noted in the previous section.

Clinical and Quality Analysis

In another aspect, the invention is a method for determining that a pharmaceutical formulation meets product quality standards. The method may comprise evaluation of a lyophilized pharmaceutical formulation (e.g., humanized anti-α4β7 antibody) comprising inspecting the formulation to assess appearance, determining reconstitution time, determining moisture content of lyophilized formulation, measuring aggregates in lyophilized formulation, measuring fragmentation, measuring oxidation/deamidation, and optionally assessing biological activity and potency, wherein achievement of pre-determined standards demonstrates product is indicated for clinical use.

Acceptable quality levels include ≤5.0% moisture, ≤40 minutes reconstitution time, pH 6.3±0.3 of reconstituted liquid, 54.0 to 66.0 mg/ml antibody concentration, ≥55.0% major isoform by CEX, ≥96.0% monomer by SEC, ≤2.5% high molecular weight (aggregates), ≥90% H+L chains by SDS-PAGE, 60-140% of the reference standard adhesion.

The invention will be more fully understood by reference to the following examples. They should not, however, be construed as limiting the scope of the invention. All literature and patent citations are incorporated herein by reference.

Development Protocol for Making Formulation

A. Anti-α4β7 Antibody Solution

Bottles of frozen, high concentration anti-α4β7 antibody preparation (vedolizumab, 50 mM histidine, 125 mM arginine, 0.06% polysorbate 80, pH 6.3) are thawed at room temperature for 16-24 hours. Thawed bottles are pooled into a stainless steel compounding vessel and mixed. The preparation is then diluted with Dilution Buffer A (50 mM histidine, 125 mM arginine, 0.06% polysorbate 80, pH 6.3) to 80 mg/mL of vedolizumab and mixed. Sucrose is then added by diluting the preparation with Dilution Buffer B which contains sucrose (50 mM histidine, 125 mM arginine, 40% sucrose, 0.06% polysorbate 80, pH 6.3). This step dilutes the anti-α4β7 antibody preparation to a liquid formulation of 60 mg/mL vedolizumab, 50 mM histidine, 125 mM arginine, 10% sucrose, 0.06% polysorbate 80, pH 6.3.

B. Lyophilization

Anti-α4β7 antibody liquid formulation at 60 mg/ml in 50 mM histidine, 125 mM arginine, 0.06% polysorbate 80, 10% sucrose, at pH6.3 is filled into 20 mL glass vials with 5.52 mL per vial and the stoppers are placed in the lyophilization position. Vials are loaded onto shelves set at about 20° C. in a lyophilizer. After loading all vials and closing the door, the shelf temperature is lowered to freeze the solution, about −45° C. After 3 hours at this temperature, the temperature of the shelves is raised to −20° C. for annealing. After annealing for four hours, the temperature of the shelves is lowered to re-freeze the solution, about −45° C. After equilibration of the vials to this temperature, the air is evacuated from the chamber. When the pressure is 150 mTorr, the shelf temperature is ramped to the primary drying temperature, about −24° C. Primary drying proceeds until the all of the crystalline ice has sublimed from the vials. Then the shelf temperature is raised to 27° C. for secondary drying for 16 hours, until the moisture is approximately less than 2.5% of the lyophilized formulation. When secondary drying is complete, nitrogen gas is backfilled into the chamber until ambient pressure is reached. The vials are stoppered and removed from the lyophilizer.

C. Storage and Use of Lyophilized Anti-α4β7 Antibody

Lyophilized vials of anti-α4β7 antibody are stored at −70° C., −20° C., 2-8° C. or 25° C. for desired periods of time. When ready for use, a vial is equilibrated to room temperature. Then the contents of the vial are reconstituted with a syringe containing water for injection ("WFI") using a 21 G needle. The amount of WFI is determined so the final volume of the reconstituted antibody solution is the same volume of the pre-lyophilized solution. For a 5.52 ml pre-lyophilization volume, 4.8 ml of WFI is added. The vial is gently swirled and then held for 10-30 minutes to allow the formulation to reconstitute, then the antibody solution is removed using a syringe and is added and added to an IV bag for IV infusion to a patient.

EXEMPLIFICATION

Example 1

Figure 6A:
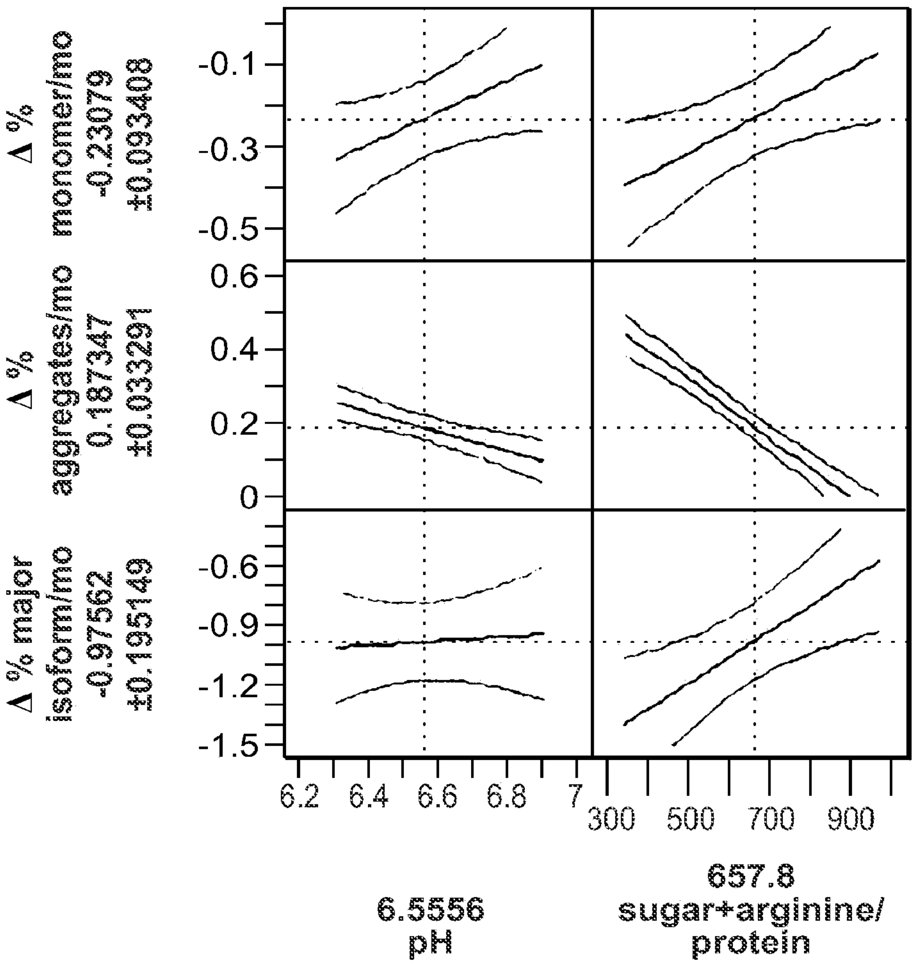
FIG. 6A shows the predicted models for change in percent monomer, change in percent aggregate, and change in percent major isoform of the anti-α4β7 lyophilized formulation. The models are based on statistical analysis of the data presented in Example 1. The center line shows the results for the predictive models and the outer lines show the 95% confidence limit for the predictive models.

Comparative Data for Varying % Sugar and Amino Acids in Lyophilized Formulations A design of experiments approach was performed to look at the effect of varying the molar ratio of sugar (sucrose and mannitol) to protein, the molar ratio of arginine to protein, and the molar amount of histidine buffer. Histidine and arginine are known not to crystallize during the lyophilization process, making them potential cryo or lyo protectants. 1.5 mL of formulation was filled into 5 mL vials lyophilized with Primary Drying at −30° C., 150 mT and Secondary Drying at 20° C., 150 mT. The stability of the lyophilized formulations reconstituted to 1.5 ml after different storage conditions is shown in Tables 1-3 (compiling 60 mg/ml results from two experiments). FIG. 6A shows the predictive models for changes in Percent Monomer, Percent Aggregates, and Percent Major Isoform when stored at 40° C. when pH and the molar ratio of sugar and arginine was varied. The stability of the formulation was best at low pH and high molar ratio of (sugar+arginine) to protein. At the histidine molar amounts examined, histidine did not affect the stability of the formulation. All formulations had 1-2% moisture during storage.

TABLE 1

Change in Percent Monomer when stored at 5° C., 25° C./60% RH, and 40° C./75% RH for 3 months. Percent Monomer was measured using Size Exclusion Chromatography (SEC).

| Formulation 60 mg/mL vedolizumab+ | % Monomer by SEC t = 0 | 5° C. 3 mo | 25° C. 60% RH 3 mo | 40° C. 75% RH 3 mo |
|---|---|---|---|---|
| 25 mM histidine, 75 mM arginine, 2% sucrose, 0.05% polysorbate 80, pH 6.3 | 98.1 | 98.1 | 97.8 | 96.5 |
| 25 mM histidine, 75 mM arginine, 4% sucrose, 0.05% polysorbate 80, pH 6.9 | 98.0 | 98.2 | 98.0 | 97.5 |
| 50 mM histidine, 125 mM arginine, 2% sucrose, 0.05% polysorbate 80, pH 6.7 | 98.0 | 98.3 | 98.1 | 97.4 |
| 50 mM histidine, 125 mM arginine, 4% sucrose, 0.05% polysorbate 80, pH 6.9 | 98.0 | 98.3 | 98.1 | 97.4 |
| 50 mM histidine, 125 mM arginine, 6% sucrose, 1.5% mannitol, 0.06% polysorbate 80, pH 6.3 | 98.7 | 98.4 | 98.4 | 98.1 |
| 50 mM histidine, 125 mM arginine, 9% sucrose, 0.06% polysorbate 80, pH 6.3 | 98.7 | 98.3 | 98.1 | 98.3 |

TABLE 2

Change in Percent Aggregates when stored 5° C., 25° C./60% RH, and 40° C./75% RH for 3 months. Percent Monomer was measured using Size Exclusion Chromatography (SEC).

| Formulation 60 mg/mL vedolizumab+ | % Aggregates by SEC t = 0 | 5° C. 3 mo | 25° C. 60% RH 3 mo | 40° C. 75% RH 3 mo |
|---|---|---|---|---|
| 25 mM histidine, 75 mM arginine, 2% sucrose, 0.05% polysorbate 80, pH 6.3 | 0.42 | 0.53 | 0.89 | 1.99 |
| 25 mM histidine, 75 mM arginine, 4% sucrose, 0.05% polysorbate 80, pH 6.9 | 0.41 | 0.51 | 0.62 | 1.15 |
| 50 mM histidine, 125 mM arginine, 2% sucrose, 0.05% polysorbate 80, pH 6.7 | 0.42 | 0.47 | 0.60 | 1.23 |
| 50 mM histidine, 125 mM arginine, 4% sucrose, 0.05% polysorbate 80, pH 6.9 | 0.36 | 0.44 | 0.52 | 0.82 |
| 50 mM histidine, 125 mM arginine, 6% sucrose, 1.5% mannitol, 0.06% polysorbate 80, pH 6.3 | 0.53 | 0.49 | 0.51 | 0.56 |
| 50 mM histidine, 125 mM arginine, 9% sucrose, 0.06% polysorbate 80, pH 6.3 | 0.51 | 0.51 | 0.59 | 0.56 |

TABLE 3

Change in Percent Major Isoform when stored at 5° C., 25° C./60% RH, and 40° C./75% RH for 3 months. Major Isoform was measured using Cation Exchange Chromatography (CEX).

| Formulation 60 mg/ml vedolizumab+ | % Major Isoform by CEX t = 0 | 5° C. 3 mo | 25° C. 60% RH 3 mo | 40° C. 75% RH 3 mo |
|---|---|---|---|---|
| 25 mM histidine, 75 mM arginine, 2% sucrose, 0.05% polysorbate 80, pH 6.3 | 70.5 | 68.8 | 67.4 | 66.3 |
| 25 mM histidine, 75 mM arginine, 4% sucrose, 0.05% polysorbate 80, pH 6.9 | 70 8 | 98.9 | 68.0 | 67.7 |
| 50 mM histidine, 125 mM arginine, 2% sucrose, 0.05% polysorbate 80, pH 6.7 | 70.5 | 68.9 | 67.8 | 66.5 |
| 50 mM histidine, 125 mM arginine, 4% sucrose, 0.05% polysorbate 80, pH 6.9 | 70.6 | 68.9 | 68.0 | 67.4 |
| 50 nM histidine, 125 mM arginine, 6% sucrose, 1.5% mannitol, 0.06% polysorbate 80, pH 6.3 | 69.6 | 69.5 | 69.3 | 67.4 |
| 50 mM histidine, 125 mM arginine, 9% sucrose, 0.06% polysorbate 80, pH 6.3 | 69.5 | 69.3 | 69.2 | 68 1 |

FIG. 6A shows the predicted models based on the statistical analysis of 40° C. data from Tables 1-3. The model for change in percent monomer per month at 40° C. by SEC analysis is −3.10+(0.386)*pH+0.0005160 ((moles of sugar+moles arginine)/moles of protein)). The model for change in percent aggregate per month at 40° C. by SEC analysis is 2.43−(0.263)*pH −0.000787*((moles of sugar+moles arginine)/moles of protein)). The model for change in percent major isoform per month at 40° C. by CLX analysis is −2.54+(0.109)*pH−0.00130e ((moles of sugar+moles arginine)/moles of protein)). The center line shows the results for the predictive models and the outer lines show the 95% confidence limit for the predictive models.

Figure 6B:
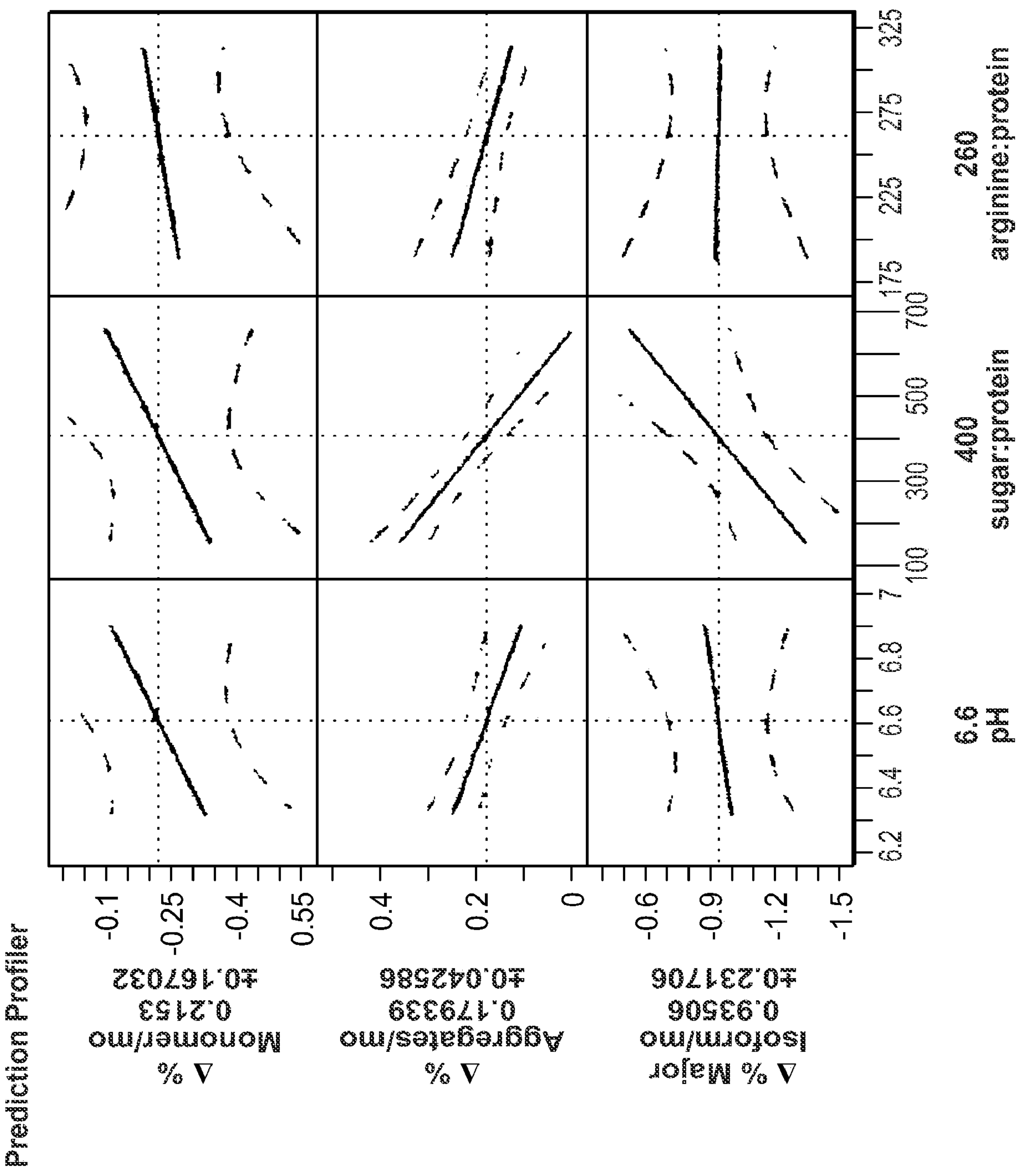
FIG. 6B shows alternative models based on the statistical analysis of 40° C. data from Tables 1-3 when the input factors are pH, sugar: protein molar ratio, and arginine:protein molar ratio. The center line shows the results for the predictive models and the outer lines show the 95% confidence limit for the predictive models.

FIG. 6B shows alternative models based on the statistical analysis of 40° C. data from Tables 1-3 when the input factors are pH, sugar:protein molar ratio, and arginine:protein molar ratio. The model for change in percent monomer per month at 40° C. by SEC analysis is −3.02+(0.370)*pH+0.000482*((moles of sugar)/(moles of protein)+0.000657*((moles of arginine/moles of protein). The model for change in percent aggregate per month at 40° C. by SEC analysis is 2.35−(0.244)*pH−0.000727*((moles of sugar)/(moles of protein)−0.00102*((moles of arginine)/(moles of protein)). The model for change in percent major isoform per month at 40° C. by CEX analysis is −2.92+(0.210)*pH+0.00164*((moles of sugar)/(moles of protein)−0.000220*((moles of arginine)/(moles of protein)). The center line shows the results for the predictive models and the outer lines show the 95% confidence limit for the predictive models.

Example 2

Stability Data

Three primary stability batches of the formulation (Batch A, B, and C) were tested for stability after storage at the prescribed storage condition (5 and 25° C./60% RH for up to 24 months). All three batches contain the same liquid formulation that was lyophilized: 60 mg/mL anti-α4β7 antibody, 50 mM histidine, 125 mM arginine, 10% sucrose, 0.06% polysorbate 80, pH 6.3. For Batch A, 3.5 mL of solution was filled into 20 mL vials and lyophilized, for Batches B and C, 5.52 mL of solution was filled into 20 mL vials and lyophilized.

In a separate study, a single drug formulation of 60 mg/ml anti-α4β7 antibody, 50 mM histidine, 125 mM arginine, 10% sucrose, 0.06% polysorbate 80, pH 6.3 was lyophilized in two volumes, 3.5 ml and 9.5 ml, respectively, to yield Batches R and S for stability samples, which were analyzed over 38 months. Blanks are NT (not tested).

The data (Tables 4-19) showed that the antibody formulations remained stable when stored for up to 38 months at 5° C. and up to 30 months at 25° C./60% RH. All product attributes remained within the specifications through the 38 month time point.

TABLE 4

Change in Percent Monomer by SEC when stored at 5° C.

| Time (months) | Batch A | Batch B | Batch C | Batch R | Batch S |
|---|---|---|---|---|---|
| 0 | 99.8 | 99.8 | 99.8 | 98.9 | 98.8 |
| 1 | 99.8 | 99.1 | 99.2 | 98.8 | 99.2 |
| 3 | 99.8 | 99.1 | 99.1 | 98.8 | 98.8 |
| 6 | 99.8 | 99.8 | 99.8 | 98.9 | 99.0 |
| 9 | 99.1 | 99.2 | 99.2 | 99.2 | 99.1 |
| 12 | 99.4 | 99.0 | 99.0 | 98.8 | 98.9 |
| 15 | 99.4 | 99.1 | 99.1 | | |
| 18 | 99.5 | 99.4 | 99.4 | 98.9 | 98.9 |
| 24 | 99.4 | 99.2 | 99.2 | 99.0 | 99.0 |
| 30 | | 99.2 | 99.2 | | |
| 38 | | | | 99.3 | 99.3 |

TABLE 5

Change in Percent Aggregates by SEC when stored at 5° C.

| Time (months) | Batch A | Batch B | Batch C | Batch R | Batch S |
|---|---|---|---|---|---|
| 0 | 0.1 | 0.1 | 0.1 | 0.2 | 0.2 |
| 1 | 0.1 | 0.2 | 0.2 | 0.2 | 0.1 |
| 3 | 0.1 | 0.2 | 0.2 | 0.2 | 0.2 |
| 6 | 0.2 | 0.2 | 0.2 | 0.2 | 0.2 |
| 9 | 0.1 | 0.2 | 0.2 | 0.2 | 0.2 |
| 12 | 0.2 | 0.2 | 0.2 | 0.2 | 0.2 |
| 15 | 0.2 | 0.2 | 0.2 | | |
| 18 | 0.2 | 0.2 | 0.2 | 0.2 | 0.2 |
| 24 | 0.2 | 0.2 | 0.2 | 0.2 | 0.2 |
| 30 | | 0.2 | 0.2 | | |
| 38 | | | | 0.2 | 0.2 |

TABLE 6

Change in Percent Major Isoform by CEX when stored at 5° C.

| Time (months) | Batch A | Batch B | Batch C | Batch R | Batch S |
|---|---|---|---|---|---|
| 0 | 68.6 | 69.9 | 69.5 | 71.7 | 71.6 |
| 1 | 67.5 | 68.9 | 68.8 | 71.2 | 72.0 |
| 3 | 68.7 | 68.8 | 68.7 | 70.4 | 70.3 |
| 6 | 67.7 | 68.2 | 68.2 | 71.9 | 71.9 |
| 9 | 70.0 | 68.3 | 67.8 | 69.2 | 69.7 |
| 12 | 67.8 | 68.3 | 68.1 | 70.8 | 70.9 |
| 15 | 66.9 | 67.5 | 67.5 | | |
| 18 | 67.4 | 67.0 | 66.7 | 71.0 | 70.8 |
| 24 | 68.1 | 69.6 | 69.1 | 71.3 | 70.9 |
| 30 | | 68.5 | 68.6 | | |
| 38 | | | | 73.6 | 73.1 |

TABLE 7

Change in Percent Acidic Isoforms by CEX when stored at 5° C.

| Time (months) | Batch A | Batch B | Batch C | Batch R | Batch S |
|---|---|---|---|---|---|
| 0 | 22.8 | 20.8 | 21.4 | 20.3 | 20.6 |
| 1 | 21.9 | 21.7 | 22.3 | 21.6 | 20.3 |
| 3 | 21.7 | 22.2 | 22.8 | 22.0 | 22.0 |
| 6 | 22.9 | 23.1 | 23.6 | 21.1 | 21.4 |
| 9 | 19.8 | 22.2 | 22.9 | 21.8 | 21.8 |
| 12 | 22.9 | 21.3 | 22.1 | 21.2 | 21.2 |
| 15 | 22.7 | 22.3 | 22.8 | | |
| 18 | 22.8 | 22.3 | 22.6 | 21.1 | 21.5 |
| 24 | 21.7 | 22.1 | 22.9 | 20.6 | 20.7 |
| 30 | | 22.8 | 23.2 | | |
| 38 | | | | 18.9 | 19.1 |

TABLE 8

Change in Percent Basic Isoforms by CEX when stored at 5° C.

| Time (months) | Batch A | Batch B | Batch C | Batch R | Batch S |
|---|---|---|---|---|---|
| 0 | 8.5 | 9.3 | 9.1 | 8.1 | 7.8 |
| 1 | 10.7 | 9.4 | 8.9 | 7.3 | 7.7 |
| 3 | 9.7 | 9.0 | 8.5 | 7.6 | 7.8 |
| 6 | 9.5 | 8.7 | 8.2 | 7.0 | 6.7 |
| 9 | 10.2 | 9.6 | 9.3 | 9.0 | 8.4 |
| 12 | 9.3 | 10.3 | 9.9 | 8.0 | 7.9 |
| 15 | 10.4 | 10.1 | 9.7 | | |
| 18 | 9.8 | 10.7 | 10.7 | 7.9 | 7.7 |
| 24 | 10.2 | 8.3 | 8.1 | 8.1 | 8.3 |
| 30 | | 8.7 | 8.2 | | |
| 38 | | | | 7.5 | 7.7 |

TABLE 9

Change in % (H + L) by Reduced-SDS Page when stored at 5° C.

| Time (months) | Batch A | Batch B | Batch C | Batch R | Batch S |
|---|---|---|---|---|---|
| 0 | 98 | 98 | 98 | 96 | 96 |
| 1 | 98 | 94 | 98 | 98 | 98 |
| 3 | 98 | 98 | 98 | 98 | 98 |
| 6 | 98 | 97 | 97 | 97 | 97 |
| 9 | 97 | 97 | 97 | 98 | 98 |
| 12 | 98 | 96 | 97 | 98 | 98 |
| 15 | 97 | 98 | 97 | | |
| 18 | 98 | 97 | 97 | 99 | 99 |
| 24 | 98 | 98 | 98 | 99 | 99 |
| 30 | | 97 | 97 | | |
| 38 | | | | 99 | 99 |

TABLE 10

Change in Binding Efficacy when stored at 5° C.

| Time (months) | Batch A | Batch B | Batch C | Batch R | Batch S |
|---|---|---|---|---|---|
| 0 | 107 | 106 | 105 | 93 | 102 |
| 1 | 106 | 106 | 103 | 103 | 111 |
| 3 | 101 | 109 | 108 | 91 | 98 |
| 6 | 97 | 106 | 105 | 114 | 121 |
| 9 | 100 | 93 | 88 | 102 | 102 |
| 12 | 103 | 101 | 87 | 119 | 116 |
| 15 | 105 | 90 | 94 | | |

TABLE 10-continued

| Change in Binding Efficacy when stored at 5° C. | | | | | |
|---|---|---|---|---|---|
| Time (months) | Batch A | Batch B | Batch C | Batch R | Batch S |
| 18 | 86 | 101 | 96 | 95 | 104 |
| 24 | 92 | 82 | 95 | 81 | 101 |
| 30 | | 87 | 94 | | |
| 38 | | | | 89 | 91 |

TABLE 11

| Change in % Moisture by KF when stored at 5° C. | | | | | |
|---|---|---|---|---|---|
| Time (months) | Batch A | Batch B | Batch C | Batch R | Batch S |
| 0 | 0.5 | 0.6 | 0.6 | 0.8 | 1.0 |
| 1 | 0.5 | 0.4 | 0.6 | | |
| 3 | 0.5 | 0.6 | 0.6 | | |
| 6 | 0.6 | 0.7 | 0.5 | 0.8 | 1.3 |
| 12 | 0.6 | 0.6 | 0.7 | 0.9 | 0.9 |
| 24 | 0.5 | 0.7 | 0.7 | 0.9 | 0.9 |
| 30 | | 0.7 | 0.7 | | |

TABLE 12

| Change in Percent Monomer by SEC when stored at 25° C./60% RH | | | | | |
|---|---|---|---|---|---|
| Time (months) | Batch A | Batch B | Batch C | Batch R | Batch S |
| 0 | 99.8 | 99.8 | 99.8 | 98.9 | 98.8 |
| 1 | 99.8 | 99.1 | 99.2 | 98.7 | 98.7 |
| 3 | 99.8 | 99.0 | 99.0 | 98.6 | 98.5 |
| 6 | 99.8 | 99.7 | 99.7 | 98.9 | 98.9 |
| 9 | 99.0 | 99.1 | 99.1 | 99.1 | 99.1 |
| 12 | 99.3 | 98.9 | 98.9 | 98.8 | 98.9 |
| 15 | 99.3 | 99.0 | 99.0 | | |
| 18 | 99.4 | 99.3 | 99.3 | 98.7 | 98.9 |
| 24 | 99.2 | 99.1 | 99.1 | 98.9 | 98.9 |
| 30 | | 99.0 | 99.0 | | |

TABLE 13

| Change in Percent Aggregates by SEC when stored at 25° C./60% RH | | | | | |
|---|---|---|---|---|---|
| Time (months) | Batch A | Batch B | Batch C | Batch R | Batch S |
| 0 | 0.1 | 0.1 | 0.1 | 0.2 | 0.2 |
| 1 | 0.2 | 0.2 | 0.2 | 0.2 | 0.2 |
| 3 | 0.2 | 0.3 | 0.2 | 0.3 | 0.3 |
| 6 | 0.2 | 0.3 | 0.3 | 0.2 | 0.2 |
| 9 | 0.2 | 0.3 | 0.3 | 0.2 | 0.2 |
| 12 | 0.2 | 0.2 | 0.2 | 0.3 | 0.3 |
| 15 | 0.3 | 0.3 | 0.3 | | |
| 18 | 0.3 | 0.3 | 0.3 | 0.3 | 0.2 |
| 24 | 0.3 | 0.3 | 0.3 | 0.3 | 0.2 |
| 30 | | 0.4 | 0.3 | | |

TABLE 14

| Change in Percent Major Isoform by CEX when stored at 25° C./60% RH | | | | | |
|---|---|---|---|---|---|
| Time (months) | Batch A | Batch B | Batch C | Batch R | Batch S |
| 0 | 68.6 | 69.9 | 69.5 | 71.7 | 71.6 |
| 1 | 67.2 | 68.4 | 68.6 | 71.2 | 71.0 |
| 3 | 68.1 | 68.6 | 68.2 | 70.3 | 70.3 |
| 6 | 65.9 | 67.8 | 67.8 | 71.5 | 71.1 |
| 9 | 69.3 | 67.5 | 66.3 | 68.6 | 69.0 |
| 12 | 66.7 | 67.5 | 67.4 | 70.1 | 70.2 |
| 15 | 66.2 | 66.6 | 66.8 | | |
| 18 | 66.1 | 65.8 | 64.9 | 70.0 | 70.3 |
| 24 | 66.7 | 68.4 | 68.2 | 70.6 | 70.1 |
| 30 | | 67.2 | 67.2 | | |

TABLE 15

| Change in Percent Acidic Isoforms by CEX when stored at 25° C./60% RH | | | | | |
|---|---|---|---|---|---|
| Time (months) | Batch A | Batch B | Batch C | Batch R | Batch S |
| 0 | 22.8 | 20.8 | 21.4 | 20.3 | 20.6 |
| 1 | 21.9 | 21.8 | 22.2 | 21.4 | 21.6 |
| 3 | 21.7 | 22.2 | 22.8 | 21.8 | 22.0 |
| 6 | 22.6 | 22.9 | 23.5 | 21.1 | 21.4 |
| 9 | 19.9 | 22.1 | 23.1 | 21.8 | 21.8 |
| 12 | 23.0 | 21.4 | 22.0 | 21.3 | 21.3 |
| 15 | 22.5 | 22.1 | 22.7 | | |
| 18 | 22.6 | 22.1 | 22.6 | 21.3 | 21.5 |
| 24 | 21.7 | 21.9 | 22.6 | 20.7 | 20.7 |
| 30 | | 22.7 | 23.2 | | |

TABLE 16

| Change in Percent Basic Isoforms by CEX when stored at 25° C./60% RH | | | | | |
|---|---|---|---|---|---|
| Time (months) | Batch A | Batch B | Batch C | Batch R | Batch S |
| 0 | 8.5 | 9.3 | 9.1 | 8.1 | 7.8 |
| 1 | 10.8 | 9.8 | 9.2 | 7.4 | 7.3 |
| 3 | 10.3 | 9.3 | 9.0 | 7.8 | 7.7 |
| 6 | 11.5 | 9.3 | 8.7 | 7.4 | 7.5 |
| 9 | 10.8 | 10.4 | 10.6 | 9.7 | 9.3 |
| 12 | 10.3 | 11.1 | 10.7 | 8.7 | 8.5 |
| 15 | 11.3 | 11.2 | 10.6 | | |
| 18 | 11.2 | 12.1 | 12.5 | 8.7 | 8.2 |
| 24 | 11.6 | 9.7 | 9.1 | 8.7 | 9.2 |
| 30 | | 10.2 | 9.6 | | |

TABLE 17

| Change in % (H + L) by Reduced-SDS Page when stored at 25° C./60% RH | | | | | |
|---|---|---|---|---|---|
| Time (months) | Batch A | Batch B | Batch C | Batch R | Batch S |
| 0 | 98 | 98 | 98 | 96 | 96 |
| 1 | 98 | 98 | 98 | 98 | 98 |
| 3 | 97 | 98 | 98 | 98 | 98 |
| 6 | 97 | 97 | 97 | 97 | 97 |
| 9 | 97 | 97 | 97 | 98 | 98 |
| 12 | 98 | 96 | 96 | 98 | 98 |
| 15 | 97 | 97 | 97 | | |

TABLE 17-continued

| Change in % (H + L) by Reduced-SDS Page when stored at 25° C./60% RH | | | | | |
|---|---|---|---|---|---|
| Time (months) | Batch A | Batch B | Batch C | Batch R | Batch S |
| 18 | 98 | 97 | 97 | 99 | 99 |
| 24 | 98 | 97 | 98 | 99 | 99 |
| 30 | | 97 | 98 | | |

TABLE 18

| Change in Binding Efficacy when stored at 25° C./60% RH | | | | | |
|---|---|---|---|---|---|
| Time (months) | Batch A | Batch B | Batch C | Batch R | Batch S |
| 0 | 107 | 106 | 105 | 93 | 102 |
| 1 | 115 | 103 | 109 | | |
| 3 | 92 | 113 | 100 | 96 | 94 |
| 6 | 109 | 89 | 97 | 101 | 114 |
| 9 | 97 | 89 | 85 | 97 | 102 |
| 12 | 83 | 91 | 123 | | |
| 15 | 96 | 91 | 96 | | |
| 18 | 106 | 123 | 87 | 92 | 102 |
| 24 | 103 | 82 | 90 | 98 | 94 |
| 30 | | 84 | 114 | | |

TABLE 19

| Change in % Moisture by KF when stored at 25° C./60% RH | | | | | |
|---|---|---|---|---|---|
| Time (months) | Batch A | Batch B | Batch C | Batch R | Batch S |
| 0 | 0.5 | 0.6 | 0.6 | 0.8 | 1.0 |
| 1 | 0.5 | 0.6 | 0.5 | | |
| 3 | 0.5 | 0.7 | 0.6 | | |
| 6 | 0.5 | 0.7 | 0.7 | 1.3 | 1.2 |
| 12 | 0.6 | 0.8 | 0.6 | 0.9 | 1.0 |
| 24 | 0.7 | 0.8 | 0.6 | 1.1 | 1.0 |
| 30 | | 0.8 | 0.7 | | |

Cation Exchange Chromatography (CEX)

A phosphate/sodium chloride gradient on a weak cation exchange column is used in a high performance liquid chromatography system to separate charged species in anti-α4β7 antibody formulations and determine the charge composition of the antibody species. Acidic Isoforms elute before the Major Isoform and Basic Isoforms elute after the Major Isoform.

Stability data for all vedolizumab batches generated using a CEX assay is presented in Tables 3, 6-8 and 14-16. The Tables show, that at these storage conditions, there was no trend of reducing the % Major Isoform below 55.0%.

Size Exclusion Chromatography (SEC)

SEC is performed using an analytical SEC column (Tosoh Bioscience, LLC, King of Prussia, PA). The mobile phase is a phosphate-buffered saline solution and the absorbance is monitored at 280 nm.

Stability data generated using an SEC assay is presented in Tables 1, 2, 4, 5, 12 and 13. The Tables show that none of the listed storage conditions resulted in lowering the % Monomer below 96.0%. Similarly, the % Aggregates remained ≤2.5% for all batches at all listed storage conditions.

SDS-PAGE Assay

SDS-PAGE is performed using an Invitrogen (Carlsbad, CA) Tris-Glycine gel, 4-20% for reducing condition and 4-12% for non-reducing condition. The reconstituted antibody formulation sample is diluted in liquid formulation buffer then diluted one to two with Tris-Glycine SDS Sample Buffer (2×, Invitrogen) either with 10% 2-mercaptoethanol (reducing sample buffer) or without 2-mercaptoethanol (non-reducing sample buffer). Samples are briefly heated and loaded in comparison with a molecular weight marker (Invitrogen). The gels are stained with colloidal coomassie blue (Invitrogen) according to the manufacturer's instruction. Protein bands are analyzed by densitometry to identify the % heavy and light chain for reduced gels and % IgG for non-reduced gels.

Stability data generated using a Reduced SDS-PAGE assay arc presented in Tables 9 and 17. No noticeable changes were observed for the % Heavy+Light (H+L) chains at all storage conditions listed for all stability lots. The banding pattern was similar to that of the reference standard and % (H+L) remained at a level ≥90%.

Binding Efficacy

HuT78 cells (human T cell lymphoma cells, American Type Culture Collection, Manassas, VA) suspended in 1% BSA in PBS, 0.01% sodium azide are contacted with serial dilutions of primary test antibody. After incubation on ice, the cells are washed and treated with fluorescently labeled secondary antibody. After a further wash, the cells are fixed and suspended in FACS reagent for analysis by flow cytometry (Becton Dickinson Franklin Lakes, NJ); also see U.S. Pat. No. 7,147,851.

Binding efficacy of vedolizumab was measured relative to the Reference Standard and reported as % Reference Standard and EC50. Stability data is presented in Tables 10 and 18. Data for the % Reference Standard showed variability but remained within the specification limits at all storage conditions. No evaluated lots of vedolizumab displayed a trend of diminished binding efficacy at the storage conditions listed.

Moisture by Karl Fischer

The formulation is titrated with methanol for a coulometric Karl Fischer moisture determination. Moisture data is presented in Tables 11 and 19. All evaluated lots of vedolizumab had less than 5% moisture at all listed storage conditions.

Capillary Isoelectric Focusing (cIEF)

cIEF is performed using an iCE280 whole column detection cIEF system (Convergent Biosciences, Toronto, Ontario). Choice of ampholyte can be as recommended by the manufacturer or can be a combination of commercially available ampholytes. A useful combination is a mixture of 3-10 and 5-8 PHARMALYTE™ (GE Healthcare, Piscataway, NJ).

Example 3: Modeling the Scale-Up of the Lyophilization Process

Figure 8:
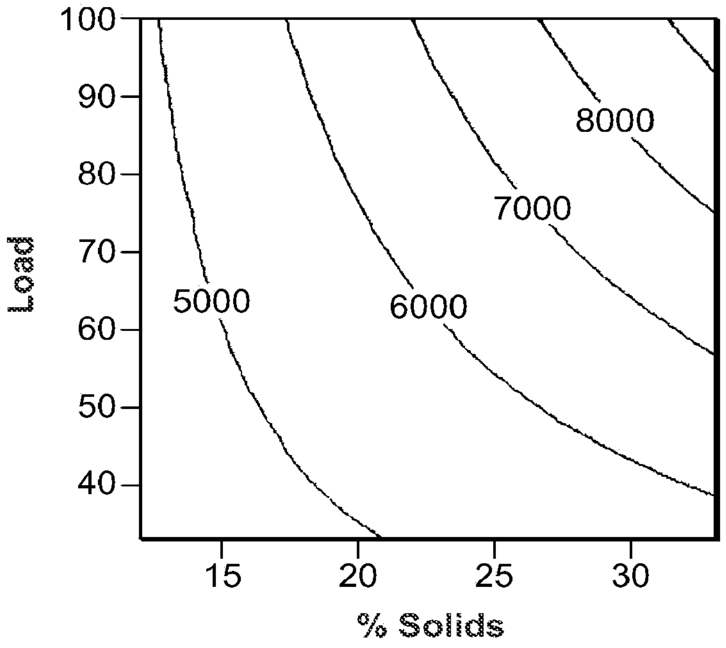
FIG. 8 is a graph showing that solids and load affect drying time (the numbers in the lines represent the number of minutes of drying time).

Quality by design was used while manipulating the load in the freeze dryer and the solids content of the formulation. The load was varied from 33 to 100%. The formulation solids content was varied from 9 to 27% by including in the loads a formulation which was 0.5×, 1.0× and 1.5× of the target formulation. These formulations had similar $T_{g'}$. With higher % solids, the primary drying time increased. In addition, at higher solids content, the product temperature increased due to larger $R_p$. The load also has an effect on both stages of drying (FIG. 8).

Example 4: Non-Clinical Safety Study

A study was designed to compare the effect of natalizumab and vedolizumab on immune surveillance of the CNS in Rhesus EAE. Eight animals were dosed with a placebo control, once weekly. Seven animals were dosed at 30 mg/kg, once weekly, with natalizumab. Seven animals were dosed at 30 mg/kg, once weekly, with vedolizumab. The clinical symptoms of EAE were observed; the frequency and ratio of leukocyte subsets in CSF were measured by flow cytometry; the total T2 lesion load in the brain was measured using MRI; and lesion load and demyelination of the brain was measured using histopathology.

Vedolizumab did not delay onset of clinical symptoms of EAE as compared to placebo control. It did not inhibit the incidence of EAE, nor the magnitude of clinical scores.

Figure 9:
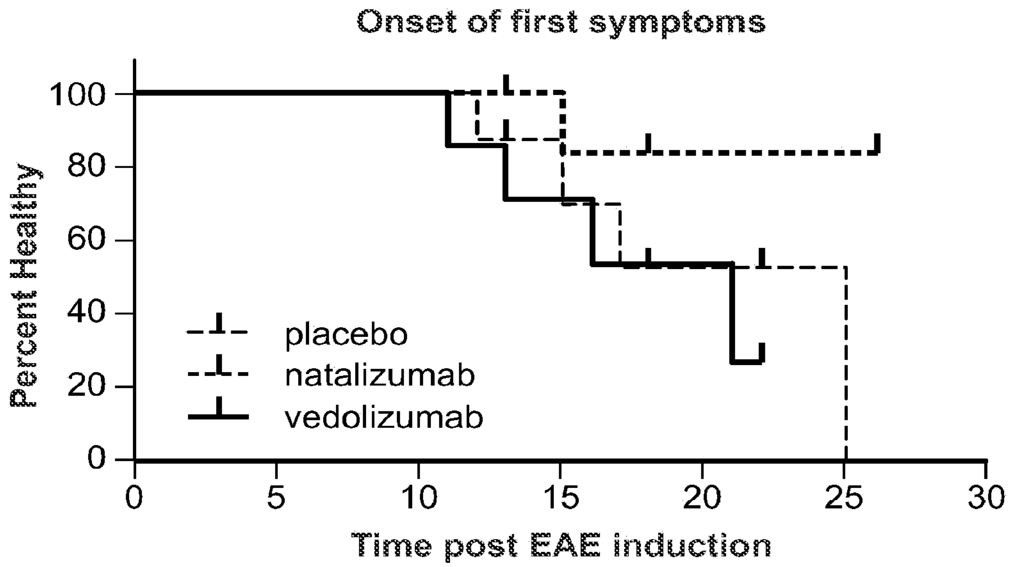
FIG. 9 is a graph showing vedolizumab did not did not delay onset of clinical symptoms of experimental autoimmune encephalomyelitis (EAE) as compared to placebo control. Natalizumab significantly ($p<0.05$) delayed onset of clinical symptoms of EAE as compared to placebo control.

Natalizumab significantly ($p<0.05$) delayed the onset of clinical symptoms of EAE as compared to placebo control. It inhibited the incidence of EAE and the magnitude of clinical scores. (FIG. 9)

Vedolizumab did not prevent infiltration of the CSF by leukocytes, T lymphocytes (helper T lymphocytes, cytotoxic T lymphocytes), B lymphocytes, natural killer cells, or monocytes. In contrast, natalizumab inhibited infiltration of the CSF Vedolizumab did not inhibit the accumulation of brain lesions, as detected by increased T2 and decreased MTR values via MRI. Natalizumab prevented lesion formation in all but one animal. Significant ($p<0.05$) inhibition in brain infiltrates and demyelination was measured by histology.

The α4β7 integrin was saturated by vedolizumab during the investigation, as shown by a competitive binding assay between vedolizumab dosed in vivo and an analytical anti-α4β7 monoclonal antibody added ex vivo. The analytical anti-α4β7 mAb does not bind to memory helper T lymphocytes in animals dosed with vedolizumab. The lack of effect of vedolizumab in the CNS is therefore due to the gastro-intestinal-tropic biology of the α4β7 integrin.

In summary, vedolizumab (an α4β7 antagonist) does not inhibit EAE. In contrast, natalizumab (α4β1 and α4β7 antagonist) does inhibit EAE. The α4β1 integrin mediates infiltration of the CNS in EAE. Thus, vedolizumab may have a lower risk of predisposing patients to PML than natalizumab because it does not antagonize the α4β1 integrin and impair immune surveillance of the CNS in Rhesus EAE.

Example 5: Phase I Clinical Study with Vedolizumab

Forty-nine healthy subjects were randomized and received a single dose of study medication: 39 subjects received vedolizumab (5 mg/mL antibody, 20 mM citrate/citric acid, 125 mM sodium chloride, 0.05% polysorbate 80, pH 6.0 (stored long term −70° C. and up to 3 months at −20° C.)) and 10 subjects received placebo. Of the 39 subjects who received vedolizumab, 8 subjects each received a dose at 0.2, 2.0, 6.0, and 10.0 mg/kg and 7 subjects received vedolizumab at 0.5 mg/kg. All 49 subjects completed the study.

There were no notable differences across vedolizumab cohorts for any demographic or baseline characteristic. Mean age ranged from 35.4 to 51.0 years; individual subject ages ranged from 21 to 63 years.

PK Results

Vedolizumab was administered as a 30-minute intravenous infusion of 0.2 to 10.0 mg/kg. The Cmax and area under the serum drug concentration-time curve of (AUC) values increased with increasing dose. The dose-corrected Cmax was approximately the same across cohorts, indicating dose proportionality for this parameter. The dose-normalized area under the serum drug concentration value from time zero to infinity ($AUC_{0\text{-}inf}$) increased with increasing dose up to 2.0 mg/kg, indicating there was a nonlinear increase in $AUC_{0\text{-}inf}$ with increasing dose over the lower range of doses administered in this study. Thereafter, $AUC_{0\text{-}inf}$ increased proportionally with dose, indicating linearity of $AUC_{0\text{-}inf}$ over the dose range 2.0 to 10.0 mg/kg. The increase in $AUC_{0\text{-}inf}$ was approximately 2.4-fold higher than expected at the 10.0 mg/kg dose compared with the 0.2 mg/kg dose.

Similarly, estimates of clearance, volume of distribution, and terminal half-life were dose-dependent over the dose range 0.2 to 2.0 mg/kg. As dose increased, clearance was reduced, distribution volume increased, and, consequently, the terminal elimination half-life was prolonged. However, from 2 to 10.0 mg/kg, there was no apparent change in these parameters, which suggests a saturation of a rapid elimination process for vedolizumab at low concentrations. Slower linear elimination processes likely account for a large fraction of clearance of vedolizumab at higher doses.

In some subjects who developed HAHA to vedolizumab, a faster clearance of vedolizumab was observed as compared to the HAHA-negative subjects within the respective dose level.

TABLE 20

Overview of Vedolizumab PK by Dose Cohort Following IV Administration of 0.2-10.0 mg/kg Vedolizumab in Healthy Subjects (PK Analysis Set)

| Parameter | VDZ dose | N | Mean | SD | Geometric Mean | % CV | Median | Min | Max |
|---|---|---|---|---|---|---|---|---|---|
| $C_{max}$ | 0.2 mg/kg | 4 | 5.65 | 0.629 | 5.62 | 11.1 | 5.45 | 5.13 | 6.56 |
| (μg/mL) | 0.5 mg/kg | 4 | 10.6 | 2.09 | 10.4 | 19.7 | 10.6 | 8.07 | 13.1 |
| | 2.0 mg/kg | 7 | 59.3 | 11.6 | 58.4 | 19.6 | 58.4 | 47.6 | 78.4 |
| | 6.0 mg/kg | 6 | 151 | 19.1 | 150 | 12.6 | 157 | 120 | 168 |
| | 10.0 mg/kg | 7 | 243 | 22.1 | 243 | 9.07 | 242 | 213 | 281 |
| $AUC_{0\text{-}tlast}$ | 0.2 mg/kg | 4 | 31.6 | 4.98 | 31.3 | 15.8 | 31.6 | 25.7 | 37.5 |
| (day*μg/mL) | 0.5 mg/kg | 4 | 127 | 48.0 | 119 | 37.9 | 129 | 70.9 | 178 |
| | 2.0 mg/kg | 7 | 964 | 147 | 955 | 15.2 | 972 | 772 | 1170 |
| | 6.0 mg/kg | 6 | 3090 | 749 | 3020 | 24.2 | 2830 | 2360 | 4100 |
| | 10.0 mg/kg | 7 | 4870 | 624 | 4840 | 12.8 | 4750 | 4120 | 5870 |
| $AUC_{0\text{-}inf}$ | 0.2 mg/kg | 4 | 39.5 | 5.79 | 39.1 | 14.7 | 40.2 | 31.7 | 45.7 |
| (day*μg/mL) | 0.5 mg/kg | 4 | 134 | 48.9 | 127 | 36.5 | 134 | 79.2 | 188 |
| | 2.0 mg/kg | 7 | 979 | 146 | 969 | 14.9 | 993 | 784 | 1180 |
| | 6.0 mg/kg | 6 | 3100 | 750 | 3030 | 24.2 | 2840 | 2390 | 4110 |
| | 10.0 mg/kg | 7 | 4880 | 637 | 4850 | 13.0 | 4750 | 4130 | 5920 |
| $V_z$(L) | 0.2 mg/kg | 4 | 4.02 | 0.151 | 4.02 | 3.76 | 4.03 | 3.83 | 4.18 |
| | 0.5 mg/kg | 4 | 4.92 | 0.620 | 4.89 | 12.6 | 4.66 | 4.52 | 5.84 |

TABLE 20-continued

Overview of Vedolizumab PK by Dose Cohort Following IV Administration of 0.2-10.0 mg/kg Vedolizumab in Healthy Subjects (PK Analysis Set)

| Parameter | VDZ dose | N | Mean | SD | Geometric Mean | % CV | Median | Min | Max |
|---|---|---|---|---|---|---|---|---|---|
| | 2.0 mg/kg | 7 | 3.34 | 0.665 | 3.28 | 19.9 | 3.23 | 2.29 | 4.27 |
| | 6.0 mg/kg | 6 | 2.98 | 0.644 | 2.92 | 21.6 | 2.98 | 2.06 | 3.98 |
| | 10.0 mg/kg | 7 | 2.89 | 1.02 | 2.73 | 35.2 | 2.98 | 1.49 | 4.58 |
| CL (L/day) | 0.2 mg/kg | 4 | 0.413 | 0.042 | 0.412 | 10.1 | 0.395 | 0.388 | 0.476 |
| | 0.5 mg/kg | 4 | 0.310 | 0.106 | 0.297 | 34.3 | 0.291 | 0.212 | 0.446 |
| | 2.0 mg/kg | 7 | 0.165 | 0.018 | 0.164 | 10.7 | 0.162 | 0.145 | 0.194 |
| | 6.0 mg/kg | 6 | 0.140 | 0.031 | 0.136 | 22.0 | 0.145 | 0.083 | 0.166 |
| | 10.0 mg/kg | 7 | 0.140 | 0.024 | 0.139 | 16.9 | 0.135 | 0.103 | 0.171 |
| $t_{1/2}$ (day | 0.2 mg/kg | 4 | 6.79 | 0.736 | 6.76 | 10.8 | 6.95 | 5.79 | 7.47 |
| | 0.5 mg/kg | 4 | 11.7 | 2.83 | 11.4 | 24.2 | 11.4 | 9.09 | 14.8 |
| | 2.0 mg/kg | 7 | 14.1 | 2.67 | 13.9 | 18.9 | 14.3 | 10.6 | 17.5 |
| | 6.0 mg/kg | 6 | 15.1 | 3.15 | 14.8 | 20.9 | 14.0 | 11.9 | 20.3 |
| | 10.0 mg/kg | 7 | 14.8 | 7.38 | 13.7 | 49.8 | 12.5 | 8.26 | 30.7 |

Abbreviations: $AUC_{0\text{-}inf}$ = area under the drug concentration-time curve, extrapolated to infinity; $AUC_{0\text{-}tlast}$ = area under the drug concentration-time curve from administration time to the last measurement time point at which the concentration is above the lower limit of quantification; CL = total clearance; $C_{max}$ = maximum drug concentration; $t_{1/2}$ = terminal half-life; $V_z$ = volume of distribution based on the terminal phase.

After reaching $C_{max}$, serum concentrations of Vedolizumab fell in a generally monoexponential fashion until concentrations reached approximately 1 to 10 mg/L. Thereafter, concentrations appeared to fall in a nonlinear fashion.

The $C_{max}$ and AUC values increased with increasing dose. For the available data, the dose-corrected $C_{max}$ was approximately the same across cohorts, indicating dose proportionality for this parameter. The dose-normalized $AUC_{0\text{-}inf}$ increased with increasing dose up to 2.0 mg/kg, indicating there was a nonlinear increase in $AUC_{0\text{-}inf}$ with increasing dose over the lower range of doses administered in this study. Thereafter, $AUC_{0\text{-}inf}$ increased proportionally with dose, indicating linearity of $AUC_{0\text{-}inf}$ over the dose range 2.0 to 10.0 mg/kg. The increase in $AUC_{0\text{-}inf}$ was approximately 2.4-fold higher than expected at the 10.0 mg/kg dose compared with the 0.2 mg/kg dose.

PD Results

The PD parameters of Vedolizumab following a 30-minute intravenous infusion of 0.2 to 10.0 mg/kg vedolizumab by cohort are summarized in Table 21 and Table 22 for Act-1 and MAdCAM respectively.

TABLE 21

Overview of Vedolizumab Pharmacodynamics, Percent Inhibition of % Act-$1^+$ [$CD4^+$ $CD45RO^{high}$], by Dose Cohort Following IV Administration of 0.2-10.0 mg/kg Vedolizumab in Healthy Subjects (PD Analysis Set)

| Parameter | VDZ dose | N | Mean | SD | Geometric Mean | % CV | Median | Min | Max |
|---|---|---|---|---|---|---|---|---|---|
| $E_{max}$ | 0.2 mg/kg | 4 | 99.6 | 0.387 | 99.6 | 0.388 | 99.6 | 99.1 | 100 |
| (% Inhibition) | 0.5 mg/kg | 4 | 99.5 | 0.599 | 99.5 | 0.602 | 99.5 | 98.9 | 100 |
| | 2.0 mg/kg | 6 | 99.9 | 0.172 | 99.9 | 0.172 | 100 | 99.6 | 100 |
| | 6.0 mg/kg | 6 | 100 | 0.000 | 100 | 0.000 | 100 | 100 | 100 |
| | 10.0 mg/kg | 6 | 99.7 | 0.326 | 99.7 | 0.327 | 99.8 | 99.3 | 100 |
| $AUEC_{0\text{-}inf}$ | 0.2 mg/kg | 4 | 4030 | 1010 | 3920 | 25.2 | 4090 | 2760 | 5160 |
| (% Inhibition*d) | 0.5 mg/kg | 4 | 6430 | 1450 | 6300 | 22.6 | 6530 | 4860 | 7810 |
| | 2.0 mg/kg | 6 | 13200 | 623 | 13200 | 4.72 | 12900 | 12800 | 14500 |
| | 6.0 mg/kg | 6 | 16700 | 3030 | 16500 | 18.1 | 16300 | 13300 | 20100 |
| | 10.0 mg/kg | 6 | 19300 | 644 | 19300 | 3.33 | 19600 | 18200 | 19900 |

$AUEC_{0\text{-}inf}$ = area under the drug effect versus time curve from time 0 to the time of the last non-zero concentration;
$E_{max}$ = maximum drug effect

TABLE 22

Overview of Vedolizumab Pharmacodynamics, Percent Inhibition of % $MADCAM^+$ [$CD4^+$ $CD45RO^{high}$], by Dose Cohort Following IV Administration of 0.2-10.0 mg/kg Vedolizumab in Healthy Subjects (PD Analysis Set)

| Parameter | VDZ dose | N | Mean | SD | Geometric Mean | % CV | Median | Min | Max |
|---|---|---|---|---|---|---|---|---|---|
| $E_{max}$ | 0.2 mg/kg | 4 | 99.2 | 0.537 | 99.2 | 0.542 | 99.4 | 98.4 | 99.6 |
| (% Inhibition) | 0.5 mg/kg | 4 | 99.6 | 0.323 | 99.6 | 0.324 | 99.5 | 99.3 | 100 |
| | 2.0 mg/kg | 6 | 99.7 | 0.365 | 99.7 | 0.366 | 99.7 | 99.2 | 100 |
| | 6.0 mg/kg | 6 | 99.8 | 0.279 | 99.8 | 0.280 | 100 | 99.4 | 100 |
| | 10.0 mg/kg | 6 | 100 | 0.000 | 100 | 0.000 | 100 | 100 | 100 |

TABLE 22-continued

Overview of Vedolizumab Pharmacodynamics, Percent Inhibition of % MADCAM+ [CD4+ CD45RO$^{high}$], by Dose Cohort Following IV Administration of 0.2-10.0 mg/kg Vedolizumab in Healthy Subjects (PD Analysis Set)

| Parameter | VDZ dose | N | Mean | SD | Geometric Mean | % CV | Median | Min | Max |
|---|---|---|---|---|---|---|---|---|---|
| $AUEC_{0\text{-}inf}$ (% Inhibition*d) | 0.2 mg/kg | 4 | 4000 | 576 | 3970 | 14.4 | 4210 | 3160 | 4440 |
| | 0.5 mg/kg | 4 | 6770 | 1400 | 6660 | 20.6 | 6840 | 5170 | 8230 |
| | 2.0 mg/kg | 6 | 13000 | 796 | 13000 | 6.12 | 13000 | 11700 | 13900 |
| | 6.0 mg/kg | 6 | 16200 | 3320 | 15900 | 20.5 | 15800 | 11800 | 20000 |
| | 10.0 mg/kg | 6 | 17700 | 1330 | 17700 | 7.5 | 17700 | 16500 | 19000 |

$AUEC_{0\text{-}inf}$ = area under the drug effect versus time curve from time 0 to the time of the last non-zero concentration;
$E_{max}$ = maximum drug effect Vedolizumab inhibited the PD parameters, Act-1 and MAdCAM-1-Fc, nearly maximally at all time points where vedolizumab was measurable in serum. Once vedolizumab concentrations decreased below the limit of detection of the assay, the inhibition of Act-1 and MAdCAM-1-Fc returned to approximately the baseline level.

In some subjects who developed HAHA to vedolizumab, a faster loss of α4β7 receptor saturation was observed as compared to the HAHA-negative subjects in the respective dose level.

Safety Results

Vedolizumab was generally safe and well tolerated at single IV doses up to 10.0 mg/kg. No deaths, serious adverse events (SAEs) or AEs leading to study discontinuation occurred during the study.

Immunogenicity/Human Antihuman Antibody (HAHA) Formation

One (10%) subject in the placebo group and 21 (54%) subjects in the combined vedolizumab dose groups had a positive HAHA at some point during the study. Although positive HAHA samples were observed in all dose cohorts, HAHA titers >125 were found only in the 2 lowest vedolizumab dose groups. Dose-dependent suppression of HAHA formation has been observed previously with vedolizumab. Nineteen of the 22 vedolizumab-treated subjects who were HAHA-positive had neutralizing HAHA present.

TABLE 23

Overview of Human Antihuman Antibodies Findings: Safety Population

| | Placebo N = 10 | 0.2 mg/kg VDZ N = 8 | 0.5 mg/kg VDZ N = 7 | 2.0 mg/kg VDZ N = 8 | 6.0 mg/kg VDZ N = 8 | 10.0 mg/kg VDZ N = 8 | Combined VDZ N = 39 |
|---|---|---|---|---|---|---|---|
| Subjects Tested | 10 | 8 | 7 | 8 | 8 | 8 | 39 |
| Any HAHA Positive, n (%) | 1 (10) | 6 (75) | 4 (57) | 2 (25) | 3 (38) | 6 (75) | 21 (54) |
| Highest HAHA Titer <125, n(%) | 1 (10) | 4 (50) | 2 (29) | 2 (25) | 3 (38) | 6 (75) | 17 (44) |
| Highest HAHA Titer ≥125, n(%) | 0 | 2 (25) | 2 (29) | 0 | 0 | 0 | 4 (10) |
| Any Neutralizing HAHA Positive, n(%) | 0 | 5 (63) | 4 (57) | 2 (25) | 3 (38) | 5 (63) | 19 (49) |
| Highest Neutralizing HAHA Titer <125, n(%) | 0 | 3 (38) | 2 (29) | 2 (25) | 3 (38) | 5 (63) | 15 (38) |
| Highest Neutralizing HAHA Titer ≥125, n(%) | 0 | 2 (25) | 2 (29) | 0 | 0 | 0 | 4 (10) |

One subject in the placebo group and 11 subjects in the vedolizumab group were persistently HAHA-positive.

TABLE 24

Overall Human Antihuman Antibody Status (Safety Population)

| | Placebo N = 10 | 0.2 mg/kg VDZ N = 8 | 0.5 mg/kg VDZ N = 7 | 2.0 mg/kg VDZ N = 8 | 6.0 mg/kg VDZ N = 8 | 10.0 mg/kg VDZ N = 8 | Combined VDZ N = 39 |
|---|---|---|---|---|---|---|---|
| HAHA negative[a] n(%) | 9 (90) | 2 (25) | 3 (43) | 6 (75) | 5 (63) | 2 (25) | 18 (46) |
| Isolated HAHA[b] n(%) | 0 | 2 (25) | 1 (14) | 1 (13) | 1 (13) | 5 (63) | 10 (26) |
| Persistent HAHA[c] n(%) | 1 (10)_ | 4 (50) | 3 (43) | 1 (13) | 2 (25) | 1 (13) | 11 (28) |

[a]HAHA Negative: Subjects with no positive HAHA results
[b]Isolated HAHA: Subjects with only 1 positive HAHA sample with titer <25
[c]Persistent HAHA: Subjects with 2 or more positive HAHA samples, or 1 positive sample with titer ≥25

Conclusions

This phase 1 study characterized the PK/PD and initial safety profiles of vedolizumab derived from CHO cells. The results of this study were used to support dose selection for phase 3 pivotal trials in inflammatory bowel disease.

Vedolizumab demonstrated dose proportionality over the tested dose range for the Cmax parameter; however, dose-dependent changes in $AUC_{0-inf}$, CL, Vz, and t1/2 were observed from 0.2 to 2.0 mg/kg, suggesting nonlinear PK behavior of vedolizumab. At dose levels greater than 2.0 mg/kg, no further changes in these parameters were observed, which suggests a saturation of a rapid elimination process for vedolizumab at low concentrations. Slower linear elimination processes likely account for a large fraction of clearance of vedolizumab at higher doses.

Vedolizumab inhibited the PD parameters, Act-1 and MAdCAM-1-Fc, at or near maximal levels at all time points when vedolizumab was measurable in serum. Once vedolizumab concentrations decreased below the limit of detection of the assay, the inhibition of Act-1 and MAdCAM-1-Fc returned to approximately the baseline level.

In some subjects who developed HAHA to vedolizumab, a faster clearance of vedolizumab and loss of α4β7 receptor saturation was observed as compared to the HAHA-negative subjects within the respective dose level.

Vedolizumab was well-tolerated. No deaths, SAEs, or AEs leading to discontinuation of study drug administration occurred during the study, nor were any dose-toxicity relationships observed. No systemic opportunistic infections (including PML) or neoplasms were reported.

Unlike nonspecific α4 antagonists, vedolizumab was not associated with lymphocytosis or mean increases in circulating eosinophils, basophils, or monocytes, nor was there any evidence of depletion of lymphocytes.

Vedolizumab did elicit the formation of HAHA, but the highest titers (>125) were observed only in the 2 lowest dose groups, a finding that supports previous observations of a dose-dependent reduction in immunogenicity. These data show that the administration of higher doses of vedolizumab may minimize clinically significant HAHA formation.

In conclusion, vedolizumab was generally safe and well tolerated when administered in single doses of 0.2 to 10.0 mg/kg to healthy subjects.

Example 6: Determination of the Effect of Vedolizumab on the CD4:CD8 Ratio

Healthy subjects ages 18-45 were treated with a single 450 mg dose of vedolizumab reconstituted from a lyophilized formulation of 10% sucrose and diluted into an infusion system of 0.9% saline. Cerebrospinal fluid (CSF) was collected by lumbar puncture before (baseline) and 5 weeks after the single 450-mg dose of vedolizumab. Each subject served as his/her own control.

A 5-week time point was selected based on a previous study that showed patients with MS treated with natalizumab demonstrated effects on CSF CD4+:CD8+ lymphocyte ratio and reduction in number of brain lesions after only one dose (Stuve et al. *Arch Neurol.* 2006; 63:1383-1387; Stuve et al. *Ann Neural.* 2006; 59:743-747. Miller et al. *N Engl J Med.* 2003; 348(1):15-23); and also because at 5 weeks, a 450-mg dose of vedolizumab is sufficient to saturate the target and provides serum concentrations that exceed estimated steady-state trough levels associated with the phase 3 dose regimen of 300 mg every 4 weeks.

Approximately 15 mL CSF was obtained from each subject for immunophenotyping. CSF samples were included for analyses if they met the following criteria: ≤10 RBCs/μL per sample (to minimize peripheral blood contamination); negative CSF culture result; adequate T-lymphocyte numbers in each flow cytometry sample; and no detection of serum antibodies to vedolizumab.

Week 5 median (34.80 μg/mL) and individual subject serum vedolizumab concentrations (range 24.9-47.9 μg/mL) were higher than projected steady-state trough concentration (~24 μg/mL) for the phase 3 dose regimen. A high degree (>90%) of α4β7 receptor saturation was observed at week 5 as measured by MAdCAM-1-Fc, indicating vedolizumab's saturation of its target at the time of endpoint assessment.

Vedolizumab was not detected in any CSF sample (detection limit=0.125 μg/mL).

Effect on CD4+ and CD8+T Lymphocyte Numbers and Ratio

Vedolizumab did not significantly reduce CD4+:CD8+ ratio (Table 25). None of the subjects had a postdose CD4+:CD8+ ratio <1 (p<0.0001 (1-sided t-test)). Vedolizumab did not significantly reduce the number of CD4+ or CD8+T lymphocytes in CSF. In addition, there were no significant changes in CSF % CD4+ and % CD8+T lymphocytes (Table 26). Also, no significant changes in peripheral blood WBC, CD4+ and CD8+ memory T lymphocytes (Table 27) were observed.

TABLE 25

Effect of Treatment on CSF CD4+:CD8+ Ratio (Evaluable Population, n = 13)

| | Baseline | Week 5 | CD4+:CD8+ Ratio Difference† |
|---|---|---|---|
| CD4+:CD8+ ratio | 3.59 (0.273) | 3.60 (0.265)* | 0.01 (0.197) |
| Mean (SE) Range | 1.53-5.67 | 1.42-5.15 | |
| 90% 2-sided CI for ratio | 3.00-4.19 | 3.132, 4.077 | |
| 90% 2-sided CI for difference | | | −0.337, 0.363 |

CI = confidence interval

*p < 0.0001 (one sided one sample t-test for H0: μ < 1 vs H1: μ >= 1).

†Difference is defined as week 5 ratio minus baseline ratio

TABLE 26

Treatment Effect on CSF CD4+ and CD8+ Lymphocyte Count (Evaluable Population, n = 13)

| | Baseline | Week 5 |
|---|---|---|
| CD4+ as % of Lymphocytes, mean (SD) | 75.160 (7.3831) | 74.215 (6.3732) |
| CD8+ as % of Lymphocytes, mean (SD) | 22.272 (5.4320) | 22.007 (6.1624) |

TABLE 27

Peripheral Blood Memory T Lymphocytes (RO+) Counts (Evaluable Population, n = 13)

| | Baseline Mean (SD) | Week 5 Mean (SD) |
|---|---|---|
| CD4+ CD45RO+ | 27.85 (4.98) | 27.06 (5.02) |
| CD8+ CD45RO+ (%) | 11.24 (3.40) | 10.78 (2.98) |

Summary

Vedolizumab did not affect CSF CD4+ and CD8+ cell counts or CD4+:CD8+ ratio in healthy volunteers after a single 450 mg dose. None of the subjects had a reduction in the post-dose CSF CD4+:CD8+ ratio to less than 1. Vedolizumab was not detected in CSF. In addition, there was no change observed in the total WBCs or memory T lymphocyte CD4+ and CD8+ subsets in peripheral blood. Saturation of the target (α4β7) in blood occurred in all subjects at the time of endpoint assessment. The CSF CD4+ and CD8+ lymphocyte levels and ratio were similar to those previously reported in the literature.

These results are consistent with vedolizumab's lack of effect on both physiologic CNS immune surveillance and pathologic CNS inflammation of monkeys (See Example 4).

Example 7: Long-Term Clinical Experience with Vedolizumab for the Treatment of IBD A phase 2 open-label safety extension study was completed to assess the long-term pharmacokinetics (PK), pharmacodynamics (PD), safety, and efficacy of vedolizumab. Patients were aged 18 to 75 years old, and had either previously participated in an earlier PK/PD/safety study in ulcerative colitis patients or had IBD symptoms for at least 2 months confirmed endoscopically and/or histopathologically and/or radiologically within 36 months of screening.

All patients received an intravenous dosing regimen of either 2 mg/kg or 6 mg/kg of vedolizumab (5 mg/mL antibody, 20 mM citrate/citric acid, 125 mM sodium chloride, 0.05% polysorbate 80, pH 6.0 (stored long term −70° C. and up to 3 mo −20° C.)) on days 1, 15 and 43, followed by a dose every 8 weeks for up to a total of 78 weeks. Patients were either treatment-naive ulcerative colitis or Crohn's disease patients, or ulcerative colitis patients that had participated in an earlier clinical trial.

Efficacy/quality of life (QoL); partial Mayo score (PMS), Crohn's disease activity index (CDAI), and Inflammatory Bowel Disease Questionnaire (IBDQ) were used to assess the results of the study.

PK Results

Mean pre-infusion vedolizumab concentrations were dose proportional, and remained steady and detectable throughout the study.

PD Results

Receptors (% ACT-1+[CD4+CD45RO HIGH] and % MADCAM+[CD4+CD45RO HIGH] were almost fully inhibited throughout the study period at all dose levels.

Partial Mayo Score

Baseline mean PMS was higher for treatment-naïve ulcerative colitis patients (5.4) than for ulcerative colitis rollover patients (2.3). By day 43, mean PMS showed a pronounced decrease for both rollover and treatment-naïve ulcerative colitis patients. By day 155, mean scores of the two groups were similar. Mean PMS continued to decrease through day 267, and leveled off thereafter.

Crohn's Disease Activity Index

CD patients' mean CDAI decreased from 294.6 at baseline to 237.7 at Day 43, and continued to decrease through day 155 (156.1).

IBDQ

Ulcerative colitis rollover patients had the highest mean IBDQ scores at baseline. By day 43, mean IBDQ scores had increased in all three disease groups. Mean IBDQ scores continued to increase over time in all 3 disease groups, reaching a maximum at day 155 for Crohn's Disease patients, and at day 491 for treatment-naïve ulcerative colitis patients and ulcerative colitis rollover patients.

C-reactive protein

Both ulcerative colitis rollover and Crohn's disease patients showed decreased mean CRP levels through day 155 and then leveled off. Treatment-naïve ulcerative colitis patients had a lower mean CRP level at baseline than ulcerative colitis rollover patients (2.28 v. 7.09). Mean CRP levels of the treatment-naïve ulcerative colitis patients remained relatively constant at all time points assessed.

Other Safety Results

No systematic opportunistic infections (including PML) were reported during the study. One patient tested positive for JC viremia at a single time point, though was negative for JCV at all other time points. Three of 72 patients (4%) had positive HAHA results (two of these were transiently positive). The study showed no evidence of liver toxicity, lymphocytosis, or lymphopenia, or any other drug-associated laboratory changes.

Conclusions

Vedolizumab administered at 2.0 or 6.0 mg/kg once every 8 weeks for up to 78 weeks achieved target receptor saturations, was associated with durable mean decreases in disease activity and improved IBDQ scores, was generally safe and well tolerated, and demonstrated acceptable immunogenicity.

Example 8: Induction of Response and Remission in Patients with Moderate to Severely Active Crohn's Disease A randomized, double blind, placebo controlled multicenter study was completed to evaluate the induction effect of vedolizumab at 300 mg doses (reconstituted from a formulation of 60 mg/ml antibody in 50 mM histidine, 125 mM arginine, 0.06% polysorbate 80, 10% sucrose, at pH6.3 which was lyophilized), in TNFα antagonist failure patients at week 6 (after 2 doses—0 and 2 weeks) and at week 10 (after 3 doses). The study consisted of 416 patients, 75% of whom were TNFα antagonist failures, and 25% of whom were TNFα naïve. Demographics and concomitant IBD medication were balanced across treatment groups. Baseline disease characteristics were also balanced across treatment groups, except for baseline disease activity.

The primary endpoint designated for the study was week 6 remission (%) in anti-TNF-α antagonist failure population. The key secondary endpoints that were evaluated (sequential testing procedure) were: week 6 remission (%) in overall population, week 10 remission (%) in anti-TNF-α antagonist failure and overall population (using Hochberg procedure), week 6 and 10 sustained remission (%) in anti-TNF-α antagonist failure and overall population (using Hochberg procedure), and week 6 enhanced response (%) in anti-TNF-α antagonist failure population.

TABLE 28

| Baseline CDAI: | | | |
|---|---|---|---|
| | Placebo | Vedolizumab | p-value |
| TNF ITT: Mean (Std Dev) | 306.1 (55.43 | 316.1 (52.63) | 0.0945 |
| Overall ITT: Mean (Std Dev) | 301.3 (54.97) | 313.9 (53.17) | 0.0153 |

TABLE 29

Induction Study Results: Primary and Key Secondary Endpoints

| | TNF ITT (N = 315) | | | | Overall ITT (N = 416) | | | |
|---|---|---|---|---|---|---|---|---|
| Endpoints | PLA N = 157 | VDZ V = 158 | Diff (RR) | P-value | PLA N = 207 | VDZ N = 209 | Diff (RR) | P-value |
| Primary Wk 6 Remission | 12.1% | 15.2% | 3.0% (1.2) | 0.4332 | | | | |
| 1st Secondary Wk 6 Remission | | | | | 12.1% | 19.1% | 6.9% (1.6) | 0.0478 |
| 2nd Secondary Wk 10 Remission | 12.1% | 26.6% | 14.4% (2.2) | 0.0012 | 13% | 28.7% | 15.5% (2.2) | <0.0001 |
| Sustained Remission (both Wk 6&10) | 8.3% | 12.0% | 3.7% (1.4) | 0.2755 | 8.2% | 15.3% | 7% (1.9) | 0.0249 |
| Enhanced Response (CDAI100) | 22.3% | 39.2% | 16.9% (1.8) | 0.0011 | | | | |

TABLE 30

Results in Anti-TNF-α Antagonist Naïve Patients (n = 101, 24% of overall)

| | Placebo % | Vedolizumab % | Difference % | 95% CI |
|---|---|---|---|---|
| Remission Week 6 | 12 | 31.4 | 19.1 | (3.3, 35.0) |
| Remission Week 10 | 16 | 35.3 | 19.2 | (2.4, 35.8) |

TABLE 31

Study Results: Clinical Remission at Weeks 6 and 10, Key Subgroup--Previous Tx Failures, ITT Overall

| Subgroup | Variable | Placebo | VDZ | Diff | 95% CI |
|---|---|---|---|---|---|
| Any prior anti-TNF failure (75% of ITT) | N | 156 | 155 | | |
| | Wk 6 Rem (%) | 12.8 | 14.8 | 2 | (−5.7, 9.7) |
| | Wk 10 Rem (%) | 12.8 | 26.5 | 13.6 | (4.9, 22.3) |
| Prior immunomodulator failure but not anti-TNF failure (21% ITT) | N | 45 | 44 | | |
| | Wk 6 Rem (%) | 11.1 | 31.8 | 20.7 | (−0.5, 39.7) |
| | Wk 10 Rem (%) | 15.6 | 31.8 | 16.3 | (−1.1, 33.6) |
| Prior corticosteroid failure only (3% ITT) | N | 5 | 9 | | |
| | Wk 6 Rem (%) | 0 | 33.3 | 33.3 | (−23.9, 75.7) |
| | Wk 10 Rem (%) | 0 | 44.4 | 44.4 | (−13.4, 85.3) |

The study showed that TNF-antagonist failure patients required 3 doses for induction of remission. Remission rates in TNF-αL antagonist failure patients increased between week 6 and week 10, but only for the vedolizumab group (not placebo). Remission rates for TNF-αL antagonist naïve patients did not increase substantially between week 6 and 10. Of the TNF-αL antagonist failure population with a high degree of disease severity, 43% never responded to a TNF-α antagonist, and 45% lost response.

Example 9: Induction and Maintenance of Response and Remission in Patients with Moderately to Severely Active Ulcerative Colitis A single trial comprising two randomized, double blind, multi-center studies designed to evaluate induction and maintenance of response and remission in patients with moderately to severely active ulcerative colitis. Demographic and baseline disease characteristics were comparable across all treatment groups.

The induction study, using intravenous administration, compared placebo against vedolizumab, at a 300 mg dose reconstituted from a lyophilized formulation of 60 mg/ml antibody in 50 mM histidine, 125 mM arginine, 0.06% polysorbate 80, 10% sucrose, at pH 6.3, with an endpoint at 6 weeks after 2 doses of vedolizumab.

The maintenance study, using the same formulation and route of administration as the induction study, compared placebo against vedolizumab dosed every four weeks, and placebo against vedolizumab dosed every eight weeks. Each patient was age 18-80, diagnosed with moderately to severely active ulcerative colitis; demonstrated, over the previous 5 year period, an inadequate response to, loss of response to, or intolerance of at least one conventional therapy (e.g. corticosteroids); and may be receiving a therapeutic dose of conventional therapies for IBD. The endpoint of this study was at 52 weeks, analyzing the induction responder population. Both phases of the trial met their primary endpoints, namely, clinical response in induction and clinical remission in maintenance.

Blood samples were collected to measure concentrations of vedolizumab during the study. The mean serum concentration of vedolizumab at the end of the induction phase was 20 to 30 μg/mL. The mean vedolizumab trough serum concentrations at steady state after 30 min IV infusion of 300 mg dose administration were between 9 to 13 μg/mL for the q8 wks regimen and between 35 to 40 μg/mL for the q4 wks regimen. At the end of infusion, the vedolizumab median plasma concentrations were between 98 and 101 μg/mL for the q8ks (8 weeks) regimen and around 129 and 137 μg/mL for the q4 wks (4 weeks).

Summaries of the responses of the induction and maintenance studies are provided in Tables 32-35. A significantly greater proportion of vedolizumab-treated patients achieved clinical response, remission, and mucosal healing at 6 weeks, compared with placebo (Table 32). 39% of the induction phase intent-to-treat population had prior anti-TNFα failure. Clinical response and remission rates were higher in vedolizumab than placebo patients among both those with prior anti-TNF failure and those with no prior anti-TNF exposure. In preliminary analyses through week 6, rates of adverse events (AEs), serious AEs, and adverse events leading to study discontinuation were higher in the placebo group than vedolizumab group. A significantly greater proportion of vedolizumab patients than placebo patients achieved clinical remission, mucosal healing, and corticosteroid-free remission at 52 wks and durable response and remission (Table 33). 32% of the maintenance study population had prior anti-TNFα failure. Clinical remission and durable clinical response rates were greater with vedolizumab than placebo in both TNF failure and TNF naïve patients. In the safety population (N=895) for wks 0-52, rates of adverse events (AEs), serious AEs, and serious infections were similar between vedolizumab and placebo groups. No increase in rates of opportunistic or enteric infections was observed in the vedolizumab group.

TABLE 32

Induction Study Results-Primary and Key Secondary Endpoints

| Efficacy Endpoints | Placebo | Vedolizumab | Difference/RR | P value |
|---|---|---|---|---|
| Clinical Response (%) | 25.5% | 47.1% | 21.7%/1.8 | <0.0001 |
| Clinical Remission(%) | 5.4% | 16.9% | 11.5%/3.1 | 0.0010 |
| Mucosal Healing(%) | 24.8% | 40.9 | 16.1%/1.6 | 0.0013 |

TABLE 33

Maintenance Study Results-Primary and Key Secondary Endpoints

| Efficacy Endpoint | Placebo N = 126 | VDZ Q8 N = 122 | VDZ Q4 N = 125 | Difference/RR Q8 vs. Pb Q4 vs. Pb | P value |
|---|---|---|---|---|---|
| Clinical Remission (%) | 15.9 | 41.8 | 44.8 | 26.1/2.7<br>29.1/2.8 | <0.0001<br><0.0001 |
| Durable Response (%) | 23.8 | 56.6 | 52.0 | 32.8/2.4<br>28.5/2.2 | <0.0001<br><0.0001 |
| Mucosal Healing (%) | 19.8 | 51.6 | 56.0 | 32.0/2.6<br>36.3/2.8 | <0.0001<br><0.0001 |
| Durable Remission (%) | 8.7 | 20.5 | 24.0 | 11.8/2.4<br>15.3/2.8 | 0.0090<br>0.0011 |
| Corticosteroid-free Remission (%) | 13.9<br>n = 72 | 31.4<br>n = 70 | 45.2<br>N = 73 | 17.6/2.3<br>31.4/3.3 | 0.0133<br><0.0001 |

TABLE 34

Induction Study: Clinical Response and Remission at 6 Weeks in Patients with Prior Anti-TNF-α Antagonist Failure and Without Anti-TNF Exposure, ITT Population

| Patients with Prior Anti-TNF-α Antagonist Failure (39%) | | | | |
|---|---|---|---|---|
| Endpoint | Placebo N = 63 | Vedolizumab N = 82 | Difference | 95% CI |
| Clinical Response (%) | 20.6 | 39.0 | 18.4 | 3.9, 32.9 |
| Clinical Remission (%) | 3.2 | 9.8 | 6.6 | −9.8, 22.8 |
| **Patients Without Anti-TNF-α Antagonist Exposure (55%)** | | | | |
| | Placebo N = 76 | Vedolizumab N = 130 | Difference | 95% CI |
| Clinical Response (%) | 26.3 | 53.1 | 26.8 | 13.7, 39.9 |
| Clinical Remission (%) | 6.6 | 23.1 | 16.5 | 2.4, 30.2 |

TABLE 35

Clinical Remission and Durable Clinical Response at 52 Weeks: Patients with Prior Anti-TNF-α Antagonist Failure or Without Anti-TNF-α Antagonist Exposure ITT Population

| Patients with Prior Anti-TNF-α Antagonist Failure (32%) | | | | | |
|---|---|---|---|---|---|
| Endpoint | Placebo N = 38 | VDZ Q8 Wks N = 43 | VDZ Q4 Wks N = 40 | Difference Q8 wks vs. Placebo Q4 wks vs. Placebo | 95% CI |
| Clinical remission (%) | 5.3 | 37.2 | 35.0 | 31.9<br>29.7 | 10.3, 51.4<br>7.4, 49.4 |
| Durable Clinical Response (%) | 15.8 | 46.5 | 42.5 | 30.7<br>26.7 | 11.8, 49.6<br>7.5, 45.9 |
| **Patients Without Anti-TNF-α Antagonist Exposure (60%)** | | | | | |
| | Placebo N = 79 | VDZ Q8 wks N = 72 | VDZ Q4 wks N = 73 | Difference Q8 wks vs. Placebo Q4 wks vs. Placebo | 95% CI |
| Clinical remission (%) | 19.0 | 45.8 | 47.9 | 26.8<br>29.0 | 12.4, 41.2<br>14.6, 43.3 |
| Durable Clinical Response (%) | 26.6 | 65.3 | 56.2 | 38.7<br>29.6 | 24.0, 53.4<br>14.6, 44.6 |

Example 10: Induction and Maintenance of Response and Remission in Patients with Moderately to Severely Active Crohn's Disease A single trial comprising two randomized, double blind, multi-center studies designed to evaluate induction and maintenance of response and remission in patients with moderately to severely active Crohn's Disease. Demographic and baseline disease characteristics were comparable across all treatment groups.

The induction study, using intravenous administration, compared placebo against vedolizumab, at a 300 mg dose reconstituted from a lyophilized formulation of 60 mg/ml antibody in 50 mM histidine, 125 mM arginine, 0.06% polysorbate 80, 10% sucrose, at pH 6.3, with an endpoint at 6 weeks after 2 doses of vedolizumab.

The maintenance study, using the same formulation and route of administration as the induction study, compared placebo against vedolizumab dosed every four weeks, and placebo against vedolizumab dosed every eight weeks. The endpoint of this study was at 52 weeks, analyzing the induction responder population.

Surprisingly, this study showed that Q4 and Q8 week groups yielded very similar results. Summaries of the responses of the induction and maintenance studies are provided in Tables 36-39. A significantly greater proportion of vedolizumab-treated patients achieved clinical remission and enhanced response, compared with placebo (Table 36). Clinical remission and enhanced response rates were higher in vedolizumab than placebo patients among both those with prior anti-TNF failure and those with no prior anti-TNF exposure. Rates of adverse events (AEs), serious AEs, and serious infections were similar between vedolizumab and placebo groups. No increase in rates of opportunistic or enteric infections was observed in the vedolizumab group.

TABLE 36

| Induction Study Results-Primary and Secondary Endpoints | | | | |
|---|---|---|---|---|
| Endpoints | Placebo N = 148 | Vedolizumab N = 220 | Adjusted Difference/RR | P value |
| Clinical Remission (%) | 6.8% | 14.5% | 7.8%/2.1 | 0.0206 |
| Enhanced Response (%) | 25.7% | 31.4% | 5.7%/1.2 | 0.2322 |
| Mean CRP Change (μg/mL) | −3.6 N = 147 | −2.9 N = 220 | | 0.9288 |

TABLE 37

| Maintenance Study Results-Primary and Key Secondary Endpoints | | | | | |
|---|---|---|---|---|---|
| Efficacy Endpoint | Placebo N = 153 | VDZ Q8 N = 154 | VDZ Q4 N = 154 | Adj. Difference/RR Q8 vs. Pb Q4 vs. Pb | P Value |
| Clinical Remission (%) | 21.6 | 39.0 | 36.4 | 17.4/1.8<br>14.7/1.7 | 0.0007<br>0.0042 |
| Enhanced Response (%) | 30.1 | 43.5 | 45.5 | 13.4/1.4<br>15.3/1.5 | 0.0132<br>0.0053 |
| Corticosteroid-free Remission (%) | 15.9 N = 82 | 31.7 N = 82 | 28.8 N = 80 | 15.9/2.0<br>12.9/1.8 | 0.0154<br>0.0450 |
| Durable Remission (%) | 14.4 | 21.4 | 16.2 | 7.2/1.5<br>2.0/1.1 | 0.1036<br>0.6413 |

TABLE 38

Clinical Remission and Enhanced Response at 6 Weeks in Patients with Prior Anti-TNF-α Antagonist Failure and Without Anti-TNF Exposure, ITT Population

| Patients with Prior Anti-TNF-α Antagonist Failure (48%) | | | | |
|---|---|---|---|---|
| Endpoint | Placebo N = 70 | Vedolizumab N = 105 | Difference | 95% CI |
| Clinical Remission (%) | 4.3 | 10.5 | 6.2 | (−9.1, 21.3) |
| Enhanced Response (%) | 22.9 | 23.8 | 1.0 | (−11.8, 13.7) |
| **Patients Without Anti-TNF-α Antagonist Exposure (50%)** | | | | |
| | Placebo N = 76 | Vedolizumab N = 130109 | Difference | 95% CI |
| Clinical Remission (%) | 9.2 | 17.4 | 8.2 | (−1.4, 17.9) |
| Enhanced Response (%) | 30.3 | 42.2 | 11.9 | (−1.9, 25.8) |

TABLE 39

Clinical Remission and Enhanced Response at 52 Weeks: Patients with Prior Anti-TNF-α Antagonist Failure or Without Anti-TNF-α Antagonist Exposure ITT Population

| Patients with Prior Anti-TNF-α Antagonist Failure (51%) | | | | | |
|---|---|---|---|---|---|
| Endpoint | Placebo N = 78 | VDZ Q8 Wks N = 82 | VDZ Q4 Wks N = 77 | Difference Q8 wks vs. Placebo Q4 wks vs. Placebo | 95% CI |
| Clinical remission (%) | 12.8 | 28.0 | 27.3 | 15.2<br>14.5 | (3.0, 27.5)<br>(2.0, 26.9) |

TABLE 39-continued

Clinical Remission and Enhanced Response at 52 Weeks: Patients with Prior Anti-TNF-α Antagonist Failure or Without Anti-TNF-α Antagonist Exposure ITT Population

| | | | | | |
|---|---|---|---|---|---|
| Enhanced Response (%) | 20.5 | 29.3 | 37.7 | 8.8<br>17.1 | (−4.6, 22.1)<br>(3.1, 31.2) |
| **Patients Without Anti-TNF-α Antagonist Exposure (45%)** | | | | | |
| | Placebo N = 71 | VDZ Q8 wks N = 66 | VDZ Q4 wks N = 71 | Difference Q8 wks vs. Placebo Q4 wks vs. Placebo | 95% CI |
| Clinical remission (%) | 26.8 | 51.1 | 46.5 | 24.8<br>19.7 | (8.9, 40.6)<br>(4.2, 35.2) |
| Enhanced Response (%) | 38.0 | 60.6 | 53.5 | 22.6<br>15.5 | (6.3, 38.9)<br>(−0.7, 31.7) |

TABLE 40

Summary of Sequences

| SEQ ID NO: | Sequence Shown | Description |
|---|---|---|
| 1 | FIG. 1 | DNA encoding heavy chain of humanized anti-α4β7 immunoglobulin |
| 2 | FIG. 1 | Amino acid sequence of heavy chain of humanized anti-α4β7 immunoglobulin |
| 3 | FIG. 2 | DNA encoding the light chain of humanized anti-α4β7 immunoglobulin |
| 4 | FIG. 2 | Amino acid sequence of light chain of humanized anti-α4β7 immunoglobulin |
| 5 | FIG. 3 | Mature humanized light chain of LDP-02 |
| 6 | FIG. 4 | Generic human kappa light chain constant region |
| 7 | FIG. 4 | Generic murine kappa light chain constant region |
| 8 | Referenced on page 34 SYWMH (SEQ ID NO: 8) | CDR1 of heavy chain mouse ACT-1 antibody |
| 9 | Referenced on page 34 EIDPSES NTNYNQKFKG (SEQ ID NO: 9) | CDR2 of heavy chain mouse ACT-1 antibody |
| 10 | Referenced on page 34 GGYDGWD YAIDY (SEQ ID NO: 10) | CDR3 of heavy chain mouse ACT-1 antibody |
| 11 | Referenced on page 34 RSSQSLA KSYGNTYLS (SEQ ID NO: 11) | CDR1 of light chain mouse ACT-1 antibody |
| 12 | Referenced on page 34 GISNRFS (SEQ ID NO: 12) | CDR2 of light chain mouse ACT-1 antibody |

TABLE 40-continued

Summary of Sequences

| SEQ ID NO: | Sequence Shown | Description |
|---|---|---|
| 13 | Referenced on page 34 LQGTHQP YT (SEQ ID NO: 13) | CDR3 of light chain mouse ACT-1 antibody |
| 14 | FIG. 7 | human GM607 CL antibody kappa light chain variable region |
| 15 | FIG. 7 | Human 21/28 CL antibody heavy chain variable region |

While this invention has been particularly shown and described with references to preferred embodiments thereof: it will be understood by those skilled in the art that various changes in form and details may be made therein without departing from the scope of the invention encompassed by the appended claims.

What is claimed is:

1. A method for treating a human patient having Crohn's disease, wherein the method comprises administering an anti-α4β7 antibody to a human patient having Crohn's disease, wherein the anti-α4β7 antibody is administered to the human patient according to a dosing regimen comprising:

a. an initial dose of 300 mg of the anti-α4β7 antibody as an intravenous infusion;

b. followed by a second subsequent dose of 300 mg of anti-α4β7 antibody as an intravenous infusion at about two weeks after the initial dose;

c. followed by a third subsequent dose of 300 mg of the anti-α4β7 antibody as an intravenous infusion at about six weeks after the initial dose;

d. followed by a fourth and subsequent doses of 300 mg of the anti-α4β7 antibody as an intravenous infusion every four weeks or every eight weeks after the third subsequent dose of the anti-α4β7 antibody;

wherein the method induces a clinical response and clinical remission in the Crohn's disease of the human patient;

wherein the dosing regimen induces tolerance for the anti-α4β7 antibody in the human patient, and the human patient has a human anti-human antibody (HAHA) titer of ≤125; and wherein the anti-α4β7 antibody is a humanized antibody and is an IgG1 isotype, and wherein the anti-α4β7 antibody comprises a light chain variable region comprising a CDR1 as set forth in SEQ ID NO:11; a CDR2 as set forth in SEQ ID NO: 12, and a CDR3 as set forth in SEQ ID NO: 13; and comprises a heavy chain variable region comprising a CDR1 as set forth in SEQ ID NO: 8; a CDR2 as set forth in SEQ ID NO: 9, and a CDR3 as set forth in SEQ ID NO: 10.

2. The method of claim 1, wherein the patient had a lack of an adequate response with, loss response to, or was intolerant to treatment with at least one of an immunomodulator, a tumor necrosis factor-alpha antagonist or combinations thereof.

3. The method of claim 1, wherein the Crohn's disease is moderately to severely active Crohn's disease.

4. The method of claim 1, wherein the method results in a reduction, elimination or reduction and elimination of corticosteroids use by the patient.

5. The method of claim 1, where the patient previously received treatment with at least one corticosteroid for the Crohn's disease.

6. The method of claim 1, wherein the anti-α4β7 antibody comprises a light chain variable region sequence that is 95% identical to amino acids 20 to 131 of SEQ ID NO: 4 or amino acids 21 to 132 of SEQ ID NO: 5, and comprises a heavy chain variable region sequence that is 95% identical to amino acids 20 to 140 of SEQ ID NO: 2.

7. The method of claim 1, wherein the anti-α4β7 antibody is administered to the human patient every eight weeks after the third subsequent dose.

8. The method of claim 7, wherein administration of the anti-α4β7 antibody is increased to every four weeks if the human patient experiences a return of one or more disease symptoms.

9. The method of claim 1, wherein clinical remission is achieved by week 52 following the initial dose.

10. A method of treating a human patient having Crohn's disease, the method comprising-administering an anti-α4β7 antibody to a human patient having Crohn's disease, wherein the anti-α4β7 antibody is administered to the human patient according to a dosing regimen comprising:

a. an initial dose of 300 mg of the anti-α4β7 antibody as an intravenous infusion;

b. followed by a second subsequent dose of 300 mg of the anti-α4β7 antibody as an intravenous infusion at about two weeks after the initial dose;

c. followed by a third subsequent dose of 300 mg of the anti-α4β7 antibody as an intravenous infusion at about six weeks after the initial dose;

d. followed by a fourth and subsequent doses of 300 mg of the anti-α4β7 antibody as an intravenous infusion every four weeks or every eight weeks after the third subsequent dose of the humanized immunoglobulin;

wherein the method induces a clinical response and clinical remission in the Crohn's disease of the human patient;

wherein the dosing regimen induces tolerance for the anti-α4β7 antibody in the human patient, and the human patient has a HAHA titer of ≤125; and wherein the anti-α4β7 antibody is humanized antibody and is an IgG1 isotype, wherein the anti-α4β7 antibody comprises a light chain variable region comprising amino acids 20 to 131 of SEQ ID NO: 4 or 21 to 132 of SEQ ID NO: 5, and comprises a heavy chain variable region comprising amino acids 20 to 140 of SEQ ID NO: 2.

11. The method of claim 10, wherein the patient had a lack of an adequate response with, loss response to, or was intolerant to treatment with at least one of an immunomodulator, a tumor necrosis factor-alpha antagonist or combinations thereof.

12. The method of claim 10, wherein the Crohn's disease is moderately to severely active Crohn's disease.

13. The method of claim 10, wherein the method results in a reduction, elimination or reduction and elimination of corticosteroids use by the patient.

14. The method of claim 10, where the patient previously received treatment with at least one corticosteroid for the Crohn's disease.

15. The method of claim 10, wherein the anti-α4β7 antibody is administered to the human patient every eight weeks after the third subsequent dose.

16. The method of claim 15, wherein administration of the anti-α4β7 antibody is increased to every four weeks if the human patient experiences a return of one or more disease symptoms.

17. The method of claim 10, wherein clinical remission is achieved by week 52 following the initial dose.

18. A method for treating Crohn's disease in a human patient, the method comprising administering vedolizumab to a human patient having Crohn's disease according to a dosing regimen comprising a. an initial dose of 300 mg of vedolizumab as an intravenous infusion;

b. followed by a second subsequent dose of 300 mg of vedolizumab as an intravenous infusion at about two weeks after the initial dose;

c. followed by a third subsequent dose of 300 mg of vedolizumab as an intravenous infusion at about six weeks after the initial dose;

d. followed by a fourth and subsequent doses of 300 mg of vedolizumab as an intravenous infusion every four weeks or every eight weeks after the third subsequent dose of vedolizumab;

wherein the method induces a clinical response and clinical remission in the Crohn's disease of the human patient, and wherein the dosing regimen induces tolerance for vedolizumab in the human patient, and the human patient has a HAHA titer of ≤125.

19. The method of claim 18, wherein the patient had a lack of an adequate response with, loss response to, or was intolerant to treatment with at least one of an immunomodulator, a tumor necrosis factor-alpha antagonist or combinations thereof.

20. The method of claim 18, wherein the method results in a reduction, elimination or reduction and elimination of corticosteroids use by the patient.

21. The method of claim 18, where the patient previously received treatment with at least one corticosteroid for the Crohn's disease.

22. The method of claim 18, wherein vedolizumab is administered to the human patient every eight weeks after the third subsequent dose.

23. The method of claim 22, wherein administration of vedolizumab is increased to every four weeks if the human patient experiences a return of one or more disease symptoms.

24. The method of claim 18, wherein the Crohn's disease is moderately to severely active Crohn's disease.

25. The method of claim 18, wherein clinical remission is achieved by week 52 following the initial dose.

26. A method for treating moderately to severely active Crohn's disease and minimizing human antihuman antibody (HAHA) formation in a human patient, the method comprising administering an anti-α4β7 antibody to a human patient having moderately to severely active Crohn's disease, according to a dosing regimen comprising:

a. an initial dose of 300 mg of the anti-α4β7 antibody as an intravenous infusion;

b. followed by a second subsequent dose of 300 mg of the anti-α4β7 antibody as an intravenous infusion two weeks after the initial dose;

c. followed by a third subsequent dose of 300 mg of the anti-α4β7 antibody as an intravenous infusion six weeks after the initial dose;

d. followed by a fourth and subsequent doses of 300 mg of the anti-α4β7 antibody as an intravenous infusion every eight weeks after the third subsequent dose of the anti-α4β7 antibody;

wherein the human patient achieves clinical response and clinical remission of the Crohn's disease;

wherein HAHA formation is minimized in the human patient, and the human patient has a HAHA titer of ≤125; and wherein the anti-α4β7 antibody is a humanized antibody and is an IgG1 isotype, and wherein the anti-α4β7 antibody comprises a light chain variable region comprising a CDR1 as set forth in SEQ ID NO:11; a CDR2 as set forth in SEQ ID NO: 12, and a CDR3 as set forth in SEQ ID NO: 13; and comprises a heavy chain variable region comprising a CDR1 as set forth in SEQ ID NO: 8; a CDR2 as set forth in SEQ ID NO: 9, and a CDR3 as set forth in SEQ ID NO: 10.

27. The method of claim 26, wherein the anti-α4β7 antibody comprises a light chain variable region sequence that is 95% identical to amino acids 20 to 131 of SEQ ID NO: 4 or amino acids 21 to 132 of SEQ ID NO: 5, and comprises a heavy chain variable region sequence that is 95% identical to amino acids 20 to 140 of SEQ ID NO: 2.

28. The method of claim 26, wherein the anti-α4β7 antibody comprises a light chain variable region sequence comprising amino acids 20 to 131 of SEQ ID NO: 4 or amino acids 21 to 132 of SEQ ID NO: 5, and comprises a heavy chain variable region sequence comprising amino acids 20 to 140 of SEQ ID NO: 2.

29. The method of claim 26, wherein the anti-α4β7 antibody is vedolizumab.

30. The method of claim 26, wherein clinical remission is achieved by week 52 following the initial dose.

* * * * *